(12) United States Patent
Shin et al.

(10) Patent No.: US 7,435,872 B2
(45) Date of Patent: Oct. 14, 2008

(54) ROLE OF P62 IN AGING-RELATED DISEASE

(75) Inventors: Jaekyoon Shin, LG Village 206-604, Keumkok-Dong, Kwanson-Ku, Suwon-Si, Kyonggi-Do (KR); Han-Woong Lee, Seongnam (KR); Goo Taeg Oh, Daejeon (KR)

(73) Assignees: Jaekyoon Shin, Suwon-si, Gyeonggi-do (KR); Samsung Electronics, Co., Ltd., Suwon-si, Gyeonggi-do (KR)

( * ) Notice: Subject to any disclaimer, the term of this patent is extended or adjusted under 35 U.S.C. 154(b) by 367 days.

(21) Appl. No.: 10/438,516

(22) Filed: May 14, 2003

(65) Prior Publication Data

US 2003/0235558 A1 Dec. 25, 2003

Related U.S. Application Data

(60) Provisional application No. 60/378,159, filed on May 14, 2002.

(51) Int. Cl.
| | |
|---|---|
| A01K 67/00 | (2006.01) |
| A01K 67/027 | (2006.01) |
| A01N 63/00 | (2006.01) |
| C12N 15/00 | (2006.01) |
| C12N 15/63 | (2006.01) |

(52) U.S. Cl. .............................. 800/18; 800/13; 800/14; 424/93.21; 435/320.1; 435/455

(58) Field of Classification Search .................... 800/13, 800/18, 14; 435/320.1, 455; 424/93.21
See application file for complete search history.

(56) References Cited

U.S. PATENT DOCUMENTS 5,962,224 A 10/1999 Shin et al.

6,291,645 B1 9/2001 Shin et al.

FOREIGN PATENT DOCUMENTS

WO WO 03/012134 A2 2/2003

OTHER PUBLICATIONS

Olsen et al., 2000, GABA in the Nervous System: the View at Fifty Years/ Editors, David I. Martin, Richard W. Olsen, Chapter 6: Function of GABA Receptors, Insight from Mutant and Knockout Mice, p. 81-95, Lippincott Williams & Wilkins, Philadelphia.*
Rescher et al., 2004, Journal of Cell Science, vol. 117, p. 2631-2639.*
Mogil et al., 1999, Pain, vol. 80, pp. 67-82.*
Sigmund, C., Jun. 2000, Arterioscler. Thromb. Vasc. Biol., p. 1425-1429.*
Leonard et al., 1995, Immunological Reviews, vol. 148, pp. 97-114.*
Wolfer et al., 2002, Trends in Neurosciences, vol. 25, No. 7, p. 336-340.*
Geetha, Thangiah et al. "Structural and functional properties of the ubiquitin binding protein p62", FEBS Letters 512 (2002) pp. 19-24.
Zatloukal, Kurt et al. "p62 is a common component of cytoplasmic inclusions in protein aggregation diseases", American Journal of Pathology 160(1) (Jan. 2002) pp. 255-263.
Shin and Moon, "P62 sequesters multi-ubiquitin conjugated proteins from the cytoplasm," Molecular Biology of the Cell, 10: 297a (1999).
Geetha and Wooten, "Association of the Atypical Protein Kinase C-interacting Protein p62/ZIP with Nerve Growth Factor Receptor TrkA Regulates Receptor Trafficking and Erk5 Signaling," Journal of Biological Chemistry, 278(7): 4730-4739 (2003).

* cited by examiner

*Primary Examiner*—Shin-Lin Chen
(74) *Attorney, Agent, or Firm*—Joseph Hyosuk Kim; JHK Law

(57) ABSTRACT

The application discloses a role of p62 in aging-related disease, such as development of obesity, type 2 diabetes mellitus, non-alcoholic fatty liver, various tumors, increased male mortality, intracellular inclusion named sequestosome, and redox regulation. In particular the application discloses a method of detecting the formation of inclusion bodies in neurodegenerative diseases. The invention further relates to a method of screening for therapeutic agents that disperse the inclusions. Further, transgenic mice containing a mutation in the p62 gene and having a functionally disrupted p62 gene locus are also disclosed.

2 Claims, 49 Drawing Sheets p62−/− p62+/+

A. 364 - PSSLDPSQEG PTGLKEAALY PHLPPEADPR LIESLSQMLS
MGFSDEGGWL TRLLQTKNYD IGAALDTIQY SKHPPPL - 440   SEQ ID NO:1

SEQUENCE LISTING

```
<160> NUMBER OF SEQ ID NOS: 2

<210> SEQ ID NO 1
<211> LENGTH: 77
<212> TYPE: PRT
<213> ORGANISM: Homo sapiens

<400> SEQUENCE: 1

Pro Ser Ser Leu Asp Pro Ser Gln Glu Gly Pro Thr Gly Leu Lys Glu
1               5                   10                  15

Ala Ala Leu Tyr Pro His Leu Pro Pro Glu Ala Asp Pro Arg Leu Ile
            20                  25                  30

Glu Ser Leu Ser Gln Met Leu Ser Met Gly Phe Ser Asp Glu Gly Gly
```

```
                35                  40                  45
Trp Leu Thr Arg Leu Leu Gln Thr Lys Asn Tyr Asp Ile Gly Ala Ala
    50                  55                  60

Leu Asp Thr Ile Gln Tyr Ser Lys His Pro Pro Pro Leu
65                  70                  75

<210> SEQ ID NO 2
<211> LENGTH: 4
<212> TYPE: PRT
<213> ORGANISM: Artificial Sequence
<220> FEATURE:
<223> OTHER INFORMATION: Fluorogenic peptides

<400> SEQUENCE: 2

Leu Leu Val Tyr
1
```

ROLE OF P62 IN AGING-RELATED DISEASE

CROSS-REFERENCE TO RELATED APPLICATIONS

The present invention claims priority to U.S. provisional application No. 60/378,159, field May 14, 2002, which is incorporated herein by reference in its entirety.

BACKGROUND OF THE INVENTION

1. Field of the Invention

The invention relates to a method of detecting the formation of inclusion bodies such as sequestosomes. The invention also relates to a method of detecting inclusion bodies in neurodegenerative diseases. The invention further relates to a method of screening for therapeutic agents that disperse the inclusions.

The invention relates to transgenic non-human animals and transgenic non-human animal cells harboring a transgene containing a mutation in the p62 gene and having a functionally disrupted p62 gene locus. The invention further relates to transgenes and targeting constructs used to produce such transgenic animals and cells, methods of using such animals for modeling aging related disorders, and methods for using such animals to produce transgenic nonhuman animals and cells including at least one further transgene. The invention further relates to functions of p62 first revealed by phenotypes generated in such transgenic animals and cells such as in development of obesity, type 2 diabetes mellitus, non-alcoholic fatty liver, various tumors, increased male mortality, intracellular inclusion named sequestosome, and redox regulation.

The invention further relates to methods of diagnosing early stage of, predisposition to or susceptibility of a mammalian subject to an aging related disorder or disease.

2. General Background and State of the Art

Cloning and sequencing of human p62 gene is described in U.S. Pat. Nos. 6,291,645B1 and 5,962,224, which are incorporated by reference herein in their entirety. The gene product, protein, in human is p62 and the gene name is SQSTM localized at the human chromosome 5q35. The same gene products of mouse and rat are named differently as A170 and ZIP, respectively, and the gene encoding A170 is localized at the mouse chromosome 11, sqstm 1. For convenience, these genes and proteins of human and mouse will be named p62 gene and p62, respectively, in this manuscript.

Aging is associated with the degeneration of cells, tissues, and organs, resulting in diseases such as cancer, cardiovascular failure, obesity, type 2 diabetes mellitus, non-alcoholic fatty liver, and a number of neurodegenerative diseases, as well as the decline of most measures of physiological performance. It has become evident that the redox status of the cell is importantly involved in several basic cellular processes, such as signal transduction, gene expression and thereby cell proliferation and apoptotic cell death. The accumulation of somatic damage is considered a main cause of the aging process. Among the various sources of somatic damage, reactive oxygen species (ROS), the natural by-products of oxidative energy metabolism, are often considered as the ultimate cause of aging.

Obesity causes many health problems. Obesity is the presence of excessive amount of adipose tissue and has become a significant human health problem in the modern world. Excessive adipose tissue causes, both independently and in association with the development of type 2 diabetes mellitus, coronary heart disease (CHD), an increased incidence of certain forms of cancer, respiratory complications and osteoarthritis. Obesity can result from a derangement in one or more of the three components of energy balance: energy intake, energy expenditure, and energy partitioning. Coordinated regulation among these three components is achieved through neuronal network and neuro-endocrine system, and any defect in these components is sufficient to cause obesity.

Diabetes is defined as a state in which carbohydrate and lipid metabolism are improperly regulated by insulin. This results in elevated fasting and postprandial serum glucose that leads to complications if left untreated. There are two major categories of the disease, Types 1 and 2. Type 2 diabetes is far more common and results from a combination of defects in insulin secretion and action. Type 2 diabetes is characterized by a progressive decrease in insulin action, followed by an inability of the $\beta$ cell to compensate for insulin resistance. Insulin resistance is the first lesion, due to interactions among genes, aging, and metabolic changes produced by obesity. Insulin resistance in visceral fat leads to increased fatty acid production, which exacerbates insulin resistance in liver and muscle. The $\beta$ cell compensates for insulin resistance by secreting more insulin. Ultimately, the $\beta$ cell can no longer compensate, leading to impaired glucose tolerance, and diabetes.

A majority of individuals suffering from type 2 diabetes are obese, with central visceral adiposity, and an imbalance in energy intake and expenditure that leads to numerous metabolic abnormalities. Insulin resistance might be the result of obesity, but might also contribute to its development. Recent insights into the biology of the adipocyte as an endocrine organ have supported this latter idea. It is now known that this cell type is more than a storage site for lipids; it also secretes a number of important circulating factors, including leptin, TNF$\alpha$, angiotensin, and PAI-1, and is the major source for endogenous production of nonesterified fatty acids (NEFA) via lipolysis. Indeed, the dynamic interactions between the adipocyte, certain nuclei of the ventromedial hypothalamus and the organs of insulin synthesis and action insure the coordinated regulation of insulin sensitivity, as well as energy intake and expenditure.

Non-alcoholic fatty liver disease (NAFLD) encompasses two histological lesions: fatty liver and steatohepatitis. Insulin resistance is suggested to be a key pathophysiological abnormality in patients with NAFLD. Insulin resistance results from a complex interplay between the major targets of insulin action, i.e. muscle, adipose tissue and liver, versus the ability of the pancreatic islet beta cells. The metabolic and clinical profile associated with insulin resistance is thus defined by the factors that produce and maintain insulin resistance and the effects of decreased insulin sensitivity on various insulin-dependent pathways. The major metabolic defects associated with insulin resistance are increased peripheral lipolysis, increased hepatic glucose output due to increased gluconeogenesis and increased lipid oxidation. This is associated with an oxidative stress in the liver that may be compounded by additional pathophysiological abnormalities. Increased fatty acid beta oxidation as well as peroxisomal fatty acid oxidation can both lead to increased reactive oxygen species generation and subsequent lipid peroxidation. The oxidative stress produced by increased fatty acid oxidation may also produce additional harmful effects that amplify the disease process in the liver.

Increased oxidative stress and resulting changes in cellular redox status is also known to be an important factor in development of a number of neurodegenerative diseases such as Alzheimer's disease, Parkinson's disease, and amyotrophic lateral sclerosis. Intracellular inclusion (ubiquitin positive and/or negative) is an ultrastructural hallmark of such neurodegenerative disorders. The fact that proteasome immunoreactivity is augmented in most dystrophic neuritis in a variety of diseases, suggesting that ubiquitin-proteasome pathway is critically involved in this pathologic insoluble matter formation. In general, ubiquitinated or oxidized proteins do not accumulate in normall cells, and are rapidly degraded at the proteasome. Ubiquitinated or oxidized protein inclusions in the cell must result from a malfunction or overload of the proteasome pathway or from structural changes in the protein substrates, halting their degradation. However, the questions of what determines the fate of a protein in relation to the formation of such abnormal inclusion bodies and what would be the pathologic impact of inclusion bodies in neuro-degeneration process remain unclear. Thus, clues to these questions would lead to better understanding of neurodegenerative process and thereby would provide diagnostic and therapeutic tools.

Aging-related disorders, such as formation of intracellular inclusions, obesity, diabetes, cancer, in particular, liver cancer, fatty liver, Paget Disease of Bone, and early mortality for male continue to pose significant health problems. What is needed is a live animal model, which may be used for the study of these diseases and other age-related disorders for screening and evaluation of potential therapeutic agents as well as potential diagnostic/prognostic probes useful in the treatment of these disorders. These and other needs in the art are addressed by the present invention.

SUMMARY OF THE INVENTION

Accordingly, it is an object of the invention to provide nonhuman animals in which expression of the p62 gene has been suppressed.

It is an object of the invention to provide nonhuman cells and nonhuman animals containing a heterozygous or homozygous null mutation of the p62 gene locus.

It is an object of the invention to provide constructs and vectors for producing such cells and animals containing a p62 heterozygous or homozygous null mutation.

In accordance with the foregoing objects, the invention in one aspect is a targeting construct for functionally disrupting a p62 gene. The targeting construct comprises a polynucleotide containing at least one portion having a sequence that is substantially homologous to a sequence present in or flanking a p62 gene locus and which, when integrated at the corresponding p62 gene locus, functionally disrupts expression of p62 protein from the gene locus. Such targeting constructs, or portions thereof, integrate at the p62 gene locus by homologous recombination between the endogenous gene locus and the targeting construct.

In one embodiment, the p62 gene is functionally disrupted by a targeting construct which inserts a sequence, typically into a coding sequence (i.e., exon), wherein the resultant disrupted p62 gene is substantially incapable of expressing a functional p62 protein. In one such embodiment, the targeting construct comprises an upstream homology region having a sequence with substantial identity to a first endogenous p62 gene sequence, a nonhomologous replacement portion, a downstream homology region having a sequence with substantial identity to a second endogenous p62 gene sequence located downstream from said first endogenous p62 sequence, wherein the upstream homology region and downstream homology region flank the nonhomologous replacement portion.

The nonhomologous replacement portion of the targeting construct advantageously comprises a positive selection expression cassette, such as neo. The targeting construct further advantageously comprises a negative selection cassette distal to either the upstream homology region or the downstream homology region. The negative selection cassette may comprise, for example, a tk gene.

According to another embodiment, the invention provides a method for generating stem cells having a functionally disrupted endogenous p62 gene comprising transferring the aforesaid targeting construct into pluripotent stem cells, and selecting for stem cells having a correctly targeted homologous recombination between the targeting construct and an endogenous p62 gene sequence.

According to yet another embodiment, the invention provides a method for generating nonhuman animals having a functionally disrupted endogenous p62 gene, comprising the steps of transferring, into a nonhuman blastocyst, stem cells having a correctly targeted homologous recombination between the aforesaid targeting construct and an endogenous p62 gene sequence; implanting the resultant blastocyst into a pseudopregnant female; and collecting offspring harboring an endogenous p62 allele having the correctly targeted homologous recombination.

According to another embodiment, the invention provides transgenic nonhuman animals and stem cells having a genome comprising at least one functionally disrupted p62 gene. The animal or stem cell is preferably homozygous for the functionally disrupted p62 gene. Such a homozygous transgenic animal or stem cell is substantially incapable of directing the efficient expression of endogenous p62. For example, in a preferred embodiment, a transgenic mouse is homozygous for an inactivated endogenous (i.e., naturally occurring) p62 gene.

According to one embodiment, the transgenic nonhuman animal or stem cell homozygous for a functionally disrupted p62 gene comprise a p62 gene disrupted by an integrated targeting construct, e.g., an integrated targeting construct comprising a neo gene.

According to a preferred embodiment of the invention, the transgenic animal is a mouse comprising a genome having a functionally disrupted murine p62 allele. Preferably, the mouse is homozygous for the functionally disrupted p62 allele. Such mice do not produce functional p62 protein.

According to another embodiment of the invention, mammalian cells and cell lines obtained and derived from the transgenic animal may be used to screen for agents that modulate aging related disorder.

The present invention also provides for the treatment of aging-related diseases or disorders in those occurrences of the disease which arise from a defect in the p62 locus. Treatment comprises the transfer of therapeutically effective DNA encoding functional p62 polypeptide to the treatment effective site, or by administration of functional p62 polypeptide directly to the treatment effective site. The present invention also provides for the treatment and detection of aging-related disorders.

Usage of p62-induced inclusion body formation either by proteasomal inhibition, by oxidative stress or by increasing cellular p62 level in the cell line or in the animal for the purpose of development of diagnostic tools or therapeutic molecules is another embodiment of the invention.

Polypeptides containing the ubiquitin chain binding region of p62 with specific hydrophobic residue(s) can be used to detect intracellular ubiquitin-positive inclusions. When these hydrophobic residues are mutated to small amino acids, such mutants may be used as negative controls in the binding of p62 with ubiquitin, which may be useful in inclusion detection assays in which labeled p62 are contacted with a sample suspected of containing inclusion bodies, and where the presence of the label is indicative of the presence of the inclusion body. Mutants may serve as negative controls. Also in such an assay, other unlabeled p62 polypeptide may be used as a competitive inhibitor. See Table 1.

The present invention is directed to a method of screening for a compound which inhibits p62/ubiquitin binding, comprising:

(a) contacting a compound with a sample containing p62 and ubiquitin;

(b) determining level of p62 and ubiquitin binding under conditions in which p62 and ubiquitin normally specifically bind to each other;

(c) determining level of p62 and ubiquitin binding, in the presence of said compound; and comparing the level of p62 and ubiquitin binding described in parts (a) and (b), wherein if said level is lower in (c) than in (b), then said compound is an inhibitor of p62 ubiquitin binding.

The present invention is also directed to a method of preventing binding between ubiquitin and p62, preferably with no or non-toxic side effect, comprising:

(a) generating a recombinant viral or plasmid vector comprising a DNA sequence encoding a ubiquitin binding fragment of p62 polypeptide operatively linked to a promoter; and (b) administering the viral or plasmid vector to a patient in need thereof; such that expression of said DNA sequence within a brain results in binding between the ubiquitin binding fragment of p62 and ubiquitin.

Further, the present inventions is directed to a method of detecting inclusion body, comprising:

(a) contacting a labeled p62 polypeptide to a sample that is suspected of containing inclusion body; and (b) assaying for the presence of the label, which indicates presence of the inclusion body.

The present invention is directed to a transgenic mouse whose somatic and germ cells comprise a functionally disrupted p62 gene, wherein said disrupted gene is introduced into the mouse or an ancestor of the mouse at an embryonic stage, wherein if homozygous for the disrupted gene exhibits an aging related disorder. In the transgenic mouse the aging related disorder may be obesity, diabetes, liver cancer, fatty liver, Paget Disease of Bone, or early mortality for male. In the transgenic mouse, the disrupted p62 gene is disrupted by an integrated targeting construct. In one aspect, the transgenic mouse does not produce p62 protein.

The invention is also directed to a mouse embryonic stem cell having a genome comprising a heterozygous or homozygous functionally disrupted p62 gene, wherein the embryonic stem cell is capable of becoming the transgenic mouse described above. The mouse embryonic stem cell may have a disrupted p62 gene by an integrated targeting construct.

The invention is further directed to a mouse somatic cell having a genome comprising a heterozygous or homozygous functionally disrupted p62 gene, which is isolated from the transgenic mouse described above, and the p62 gene may be disrupted by an integrated targeting construct. The invention is also directed to a mouse somatic cell line comprising the cells described above.

The invention is also directed to using the transgenic mouse as a tester animal, and as such includes a method of screening for a compound that counters aging-related disorder or disease of a mammal, comprising:

(a) administering a test compound to the transgenic mouse according to claim 4;

(b) measuring the level of disorder after the compound is administered; and (c) comparing the level of disorder measured in (b) with the level of disorder in a p62 deficient mouse, wherein reduction in the level of aging-related disorder in (b) compared with the p62 deficient mouse indicates that the compound counters aging-related disorder.

The invention may also include a method to assist in the diagnosis of aging-related disease in a mammalian subject, comprising the step of assaying for a mutation in the subject's gene encoding p62, wherein detection of the mutation is indicative that the subject is at risk for aging-related disease. The aging-related disease may be obesity, diabetes, liver cancer, fatty liver, Paget Disease of Bone, or early mortality for male. The mutation may be without limitation a single nucleotide polymorphism mutation, or functional disruption so that a functional p62 is not expressed. Other types of mutations are also possible, so long as p62 is mutated and its expression is deficient. In one aspect of the invention, the mammalian subject may be an infant human so that its future susceptibility to an aging-related disease may be anticipated.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings, which are given by way of illustration only, and thus are not limitative of the present invention, and wherein.

DETAILED DESCRIPTION OF THE PREFERRED EMBODIMENTS

Figure 1:
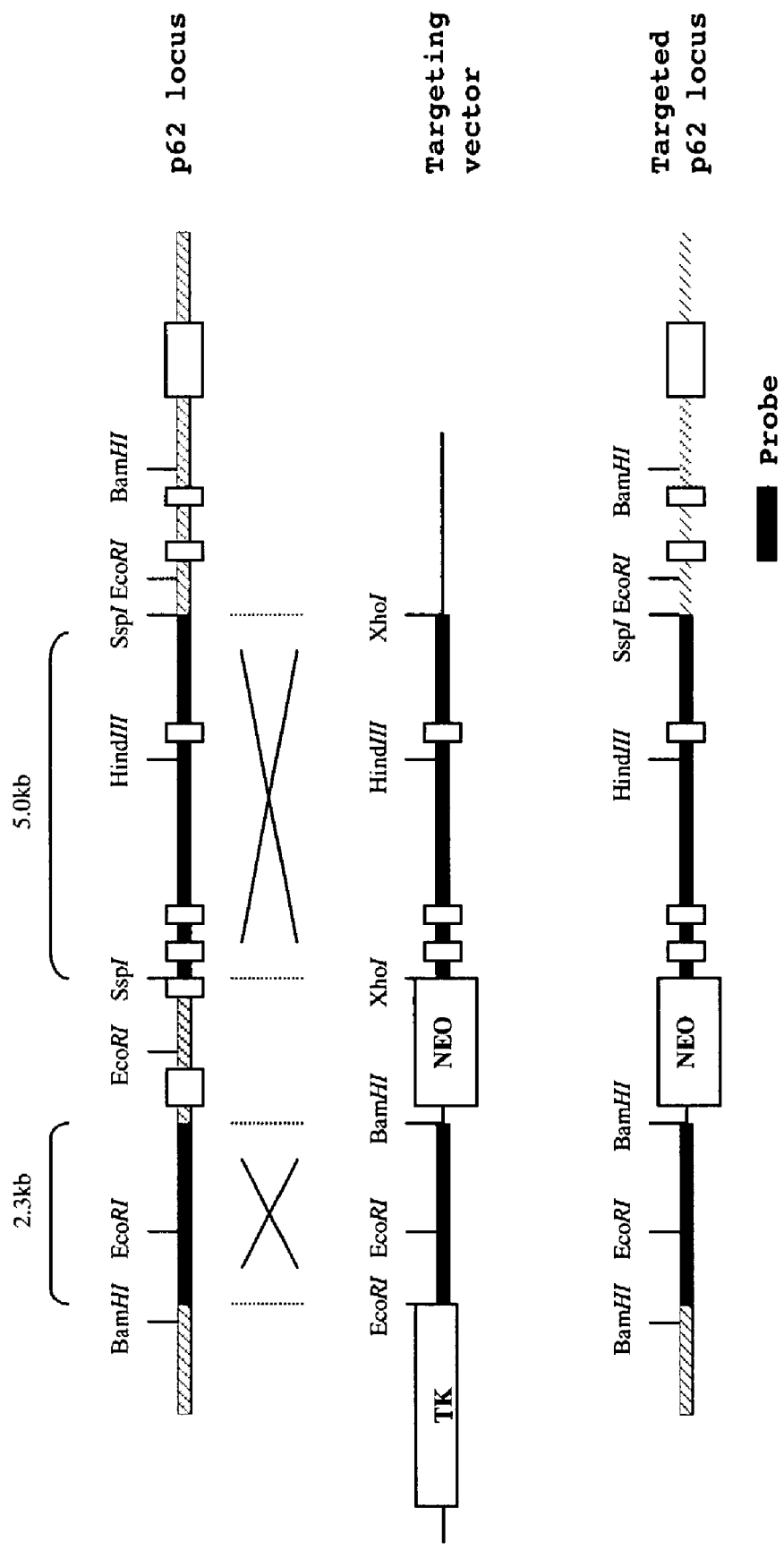
FIG. 1 shows targeted disruption of p62 gene structure of the mouse p62 gene, targeting construct, and after homologous recombination.

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, the term "agent" describes any molecule, e.g. protein, nucleic acid, or pharmaceutical compound, with the capability of affecting the molecular and clinical phenomena associated with aging related disorder. Generally a plurality of assay mixtures are run in parallel with different agent concentrations to obtain a differential response to the various concentrations. Typically, one of these concentrations serves as a negative control, i.e. at zero concentration or below the level of detection.

As used herein, "aging-related" disorder or disease refers to degeneration of cells, tissues, and organs, resulting in diseases such as cancer, cardiovascular failure, obesity, type 2 diabetes mellitus, non-alcoholic fatty liver, and a number of neurodegenerative diseases, as well as the decline of most measures of physiological performance.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

As used herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. "High stringency conditions" for the annealing process may involve, for example, high temperature and/or low salt content, which disfavor hydrogen-bonding contacts among mismatched base pairs. "Low stringency conditions" would involve lower temperature, and/or higher salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in Current Protocols in Molecular Biology, John Wiley & Sons, N.Y. (1989), 6.31-6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 75° C. Other stringency parameters are described in Maniatis, T., et al., Molecular Cloning: A Laboratory Manual, Cold Spring Harbor Laboratory Press, Cold Spring N.Y., (1982), at pp. 387-389; see also Sambrook J. et al., Molecular Cloning: A Laboratory Manual, Second Edition, Volume 2, Cold Spring Harbor Laboratory Press, Cold Spring, N.Y. at pp. 8.46-8.47 (1989).

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "covalent derivatives" include modifications of a native polypeptide or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the β-amyloid or VEGF binding polypeptides of the present invention. Other post-translational modifications include hydroxylation of proline and lysine, phosphorylation of hydroxyl groups of seryl, tyrosine or threonyl residues, methylation of the α-amino groups of lysine, arginine, and histidine side chains (T. E. Creighton, Proteins: Structure and Molecular Properties, W. H. Freeman & Co., San Francisco, pp. 79-86 (1983)).

As used herein, "corresponds to" means that a polynucleotide sequence is homologous (i.e., is identical, not stricly evolutionarily related) to all or a portion of a reference polynucleotide sequence, or that a polypeptide sequence is identical to a reference polypeptide sequence.

As used herein, the term "crossover target sequences" or "endogenous target sequences" refers to p62 gene sequences that substantially correspond to, or are substantially complementary to, a transgene homology region.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state.

As used herein, "fragment" refers to a part of a polypeptide, which retains usable and functional characteristics. For example, in one aspect, as used within the context of the present invention, the polypeptide fragment may have the function of binding to p62 or ubiquitin.

As used herein, the term "functional disruption" or "functionally disrupted" mean that a gene locus comprises at least one mutation or structural alteration such that the functionally disrupted gene is substantially incapable of directing the efficient expression of functional gene product. By way of example but not limitation, an endogenous p62 gene that has a neo gene cassette integrated into an exon of a p62 gene is not capable of encoding a functional p62 protein and is therefore a functionally disrupted p62 gene locus. Deletion or interruption of essential transcriptional regulatory elements, polyadenylation signals(s), splicing site sequences will also yield a functionally disrupted gene. Functional disruption of an endogenous p62 gene, may also be produced by other methods (e.g., antisense polynucleotide gene suppression). The term "structurally disrupted" refers to a targeted gene wherein at least one structural (i.e., exon) sequence has been altered by homologous gene targeting (e.g., by insertion, deletion, point mutation(s), and/or rearrangement). Typically, alleles that are structurally disrupted are consequently functionally disrupted. However, p62 alleles may also be functionally disrupted without concomitantly being structurally disrupted, i.e., by targeted alteration of a non-exon sequence such as ablation of a promoter. An allele comprising a targeted alteration that interferes with the efficient expression of a functional gene product from the allele is referred to as a "null allele".

As used herein, the expression "functional p62 polypeptide" means a polypeptide which, upon expression in or administration to p62−/− individuals, is sufficient to substantially restore or counter the effects of p62 null mutations in such individuals. Also included in the scope of "functional p62" polypeptide is a fusion product comprising the naturally occurring p62 polypeptide or analog thereof and one or more attached amino acid sequences which enhance the cellular uptake or penetration of the p62 polypeptide into various cells. Such fusion products may be prepared with resort to commercially available expression vectors, which provide for incorporation of DNA sequences of interest downstream from a DNA segment encoding an amino acid sequence having desirable transport properties. The resulting p62 fusion protein may be used as the exogenously sourced functional p62 protein in treating various individuals.

As used herein, the terms "homology region" and "homology clamp" refer to a segment (i.e., a portion) of a targeting construct having a sequence that substantially corresponds to, or is substantially complementary to, a predetermined p62 gene sequence, which can include sequences flanking said p62. A homology region is generally at least about 100 nucleotides long, preferably at least about 250 to 500 nucleotides long, typically at least about 1000 nucleotides long or longer.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

A "knock-out" of a gene means an alteration in the sequence of the gene that results in a decrease of function of the target gene, preferably such that target gene expression is undetectable or insignificant. A knock-out of an endogenous p62 gene means that function of the p62 gene has been substantially decreased so that expression is not detectable or only present at insignificant levels. "Knock-out" transgenics can be transgenic animals having a heterozygous knock-out of the p62 gene or a homozygous knock-out of the p62 gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

As used herein, "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

As used herein, the term "nonhomologous sequence" has both a general and a specific meaning. It refers generally to a sequence that is not substantially identical to a specified reference sequence, and where no particular reference sequence is explicitly identified, it refers specifically to a sequence that is not substantially identical to a sequence of at least about 50 contiguous bases at an endogenous p62 gene.

As used herein, "normal expression" is defined as the level of expression which is present in a wild-type animal or cell line. Accordingly, as used herein a mouse or cell line is said to be "deficient in normal expression" if the mouse or cell line expresses lower levels (including the total absence thereof) of a functional p62 when compared to that which is present in a wild-type animal or cell line. A variety of techniques known in the art can be used to quantitate the level at which a given protein is expressed. These include, but are not limited to immunological techniques such as ELISA, RIA, western blot or flow cytometry/FACS, or quantitative analytical techniques such as spectroscopy or chromatographic methods including HPLC, FPLC, affinity or flame chromatography.

As used herein, the term "p62 gene" or "p62 gene locus" refers to a region of a chromosome spanning all of the exons which potentially encode the p62 polypeptide and extending through flanking sequences (e.g., including promoters, enhancers, etc.) that participate in p62 protein expression. Thus, a p62 gene locus includes the region spanning from the first exon through the last exon and also includes adjacent flanking sequences (e.g., polyadenylation signals) that may participate in p62 gene expression.

As used herein, "p62 polypeptide" or "ubiquitin polypeptide" refers to a polypeptide that specifically binds to ubiquitin and p62, respectively. The DNA encoding the p62 polypeptide may hybridize to the wild-type p62 encoding DNA under stringent hybridization conditions. Likewise, the DNA encoding the ubiquitin polypeptide may hybridize to the wild-type ubiquitin encoding DNA under stringent hybridization conditions.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

The term "phenotype" refers to the physical, biochemical, and physiological makeup of an animal as determined both genetically and environmentally. In particular, the phrase "resulting phenotype" refers to a wild-type animal or an animal having a disease state associated with an aging related disorder.

As used herein, an agent is said to be "rationally designed" if it is selected based on a computer model of ligand binding site of the p62 protein.

As used herein, the term "replacement region" refers to a portion of a targeting construct flanked by homology regions. Upon double-crossover homologous recombination between flanking homology regions and their corresponding endogenous p62 gene crossover target sequences, the replacement region is integrated into the host cell chromosome between the endogenous crossover target sequences. Replacement regions can be homologous (e.g., have a sequence similar to the endogenous p62 gene sequence but having a point mutation or missense mutation), nonhomologous (e.g., a neo gene expression cassette), or a combination of homologous and nonhomologous regions.

As used herein, "sample" or "biological sample" is referred to in its broadest sense, and includes any biological sample obtained from an individual, body fluid, cell line, tissue culture, or other source, depending on the type of assay that is to be performed. As indicated, biological samples include body fluids, such as semen, lymph, sera, plasma, urine, synovial fluid, spinal fluid and so on. Methods for obtaining tissue biopsies and body fluids from mammals are well known in the art. A tissue biopsy of the brain is a preferred source.

In the biological sample, certain polypeptides may also be detected in vivo by imaging. Labels or markers for in vivo imaging of proteins include those detected by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the polypeptide by labeling using conventional techniques.

As used herein, "sequence identity", is further defined as the percentage of amino acid or nucleic acid residues in a candidate sequence that are identical with the amino acid residues in a native polypeptide sequence after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", Nucleic Acids Res., 25:3389-3402. The parameters are set to default values, with the exception of the Penalty for mismatch, which is set to −1.

As used herein, the term "specifically binds" refers to a non-random, non-covalent binding reaction between two molecules, for example between an antibody molecule immunoreacting with an antigen, or a non-antibody ligand reacting with another polypeptide such as p62 polypeptide and ubiquitin. Moreover, specific binding may also occur between a chemical compound or a small peptide and p62 or ubiquitin.

As used herein, "subject" is a vertebrate, preferably a mammal, more preferably a human.

As used herein, "substantially complementary" refers to a sequence that is complementary to a sequence that substantially corresponds to a reference sequence. In general, targeting efficiency increases with the length of the targeting transgene portion (i.e., homology region) that is substantially complementary to a reference sequence present in the target DNA (i.e., crossover target sequence). In general, targeting efficiency is optimized with the use of isogeneic DNA homology clamps, although it is recognized that the presence of various recombinases may reduce the degree of sequence identity required for efficient recombination.

As used herein, the term "substantially corresponds to", "substantially homologous", or "substantial identity" denotes a characteristic of a nucleic acid sequence, wherein a nucleic acid sequence has at least about 70%, 75%, 80%, 85%, 90%, 95%, 96%, 97%, 98%, 99% or 100% identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long.

As used herein, the term "targeting construct" refers to a polynucleotide which comprises: (1) at least one homology region having a sequence that is substantially identical to or substantially complementary to a sequence present in a host cell p62 gene locus, and (2) a targeting region which becomes integrated into a host cell p62 gene locus by homologous recombination between a targeting construct homology region and said p62 gene locus sequence. If the targeting construct is a "hit-and-run" or "in-and-out" type construct (Valancius and Smithies (1991) Mol. Cell. Biol. 11: 1402; Donehower et al. (1992) Nature 356: 215; (1991) J. NIH Res. 3: 59; which are incorporated herein by reference), the targeting region is only transiently incorporated into the endogenous p62 gene locus and is eliminated from the host genome by selection. A targeting region may comprise a sequence that is substantially homologous to the endogenous p62 gene sequence and/or may comprise a nonhomologous sequence, such as a selectable marker (i.e., neo, tk, gkt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene".

As used herein, the term "targeting region" refers to a portion of a targeting construct which becomes integrated into an endogenous chromosomal location following homologous recombination between a homology clamp and an endogenous p62 gene sequence. Typically, a targeting region is flanked on each side by a homology clamp, such that a double-crossover recombination between each of the homology clamps and their corresponding endogenous p62 gene sequences results in replacement of the portion of the endogenous p62 gene locus by the targeting region; in such double-crossover gene replacement targeting constructs the targeting region can be referred to as a "replacement region". However, some targeting constructs may employ only a single homology clamp (e.g., some "hit-and-run"-type vectors, see, Bradley et al. (1992) Bio/Technology 10: 534, incorporated herein by reference).

As used herein, "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc. Preferably, the transgenic animals are mice.

As used herein, "wild-type" refers to an animal or cell line that has not been genetically altered.

p62/Ubiquitin Co-Accumulation

The presence of intracellular inclusion bodies is the hallmark of various neurodegenerative disorders including without limitation, Pick's Disease (Pick's body), Amyotrophic Lateral Sclerosis (ALS) spinal cord, Huntington's Disease, Parkinson's Disease, Alzheimer's Disease neurofibrillar tangle, among others. p62 co-accumulates and co-localizes heavily with ubiquitin to form inclusion bodies in the brain and spinal cord of patients with neurodegenerative diseases. p62 binds directly to ubiquitin with specificity. In vitro experiments showed that p62 bound to ubiquitin with specificity and Applicants have discovered that inclusion bodies resulting from sequestosomes associated with these diseases are p62 positive and ubiquitin positive. Applicants have also discovered that p62 binds to ubiquiin with specificity and that certain regions on p62 bind ubiquitin. Moreover, mutations of certain hydrophobic amino acids residues in p62 enhance binding to ubiquitin.

In one aspect of the invention, the p62 polypeptide and ubiquitin polypeptide retain the capability of specifically binding to ubiquitin and p62, respectively. The length of the p62 polypeptide and ubiquitin polypeptide may vary and may include other sequences attached thereto, as well as variant sequences, which may retain the capability of specifically binding to ubiquitin and p62, respectively.

In one aspect of the invention, the p62 polypeptide may be used as a trap to immobilize ubiquitin areas where there is undesired activity of ubiquitin. The p62 polypeptide may be full length or longer or shorter or variant or derivatized, so long as the polypeptide retains the capability of specifically binding to ubiquitin.

Inhibitor of p62/Ubiquitin Binding

In one embodiment, the invention is directed to screening for a compound such as a polypeptide or chemical compound that inhibits binding of p62 to ubiquitin. It is expected that the inhibitor compound will treat persons suffering from diseases that are at least in part associated with the presence of inclusion bodies. If an inhibitor is used, ubiquinated p62 would not accumulate in the inclusion bodies, and may prevent the formation of inclusion bodies.

In this regard, in one aspect, the invention is directed to any inhibitor molecule that is capable of interacting with p62 to block the binding of p62 to ubiquitin. And alternatively, the molecule may bind to ubiquitin thus disrupting the p62/ubiquitin binding.

One such inhibitor may be modified p62 polypeptide, which retains the ubiquitin binding function but lacks or has decreased level of some or all of the other features associated with p62 function, such as capability of forming aggregates.

It is understood that the inhibitor compound may impair the interaction between the p62 polypeptide and ubiquitin by any number of biochemical or enzymatic inhibition kinetics, such as competitive, non-competitive, or uncompetitive inhibition, so long as the compound impairs the binding of p62 polypeptide to ubiquitin.

Thus, in one particular aspect, the invention is directed to using any polymer or monomer compound that is capable of inhibiting binding between p62 and ubiquitin. In another embodiment of the invention, extracts of natural foods or 'functional foods' are contemplated as comprising inhibitors of p62/ubiquitin complex.

Nucleic Acid Encoding Polypeptide that Binds to Ubiquitin or p62

By "isolated" polynucleotide sequence, it is intended to encompass a nucleic acid molecule, DNA or RNA, which has been removed from its native environment. This includes segments of DNA encoding p62 polypeptide or ubiquitin polypeptide of the present invention, and may further comprise heterologous sequences such as vector sequences or other foreign DNA. For example, recombinant DNA molecules contained in a vector are considered isolated for the purposes of the present invention, which may be partially or substantially purified.

In addition, isolated nucleic acid molecules of the invention include DNA molecules, which comprise a sequence substantially different from those described above but which, either due to the degeneracy of the genetic code or other variability, still encode p62 polypeptide or ubiquitin polypeptide and their peptides. Thus, it would be routine for one skilled in the art to generate the variants described above, for instance, to optimize codon expression or general function for a particular host.

In another aspect, the invention provides an isolated nucleic acid molecule comprising a polynucleotide which hybridizes under stringent hybridization conditions to a portion of a polynucleotide in a nucleic acid molecule of the invention described above. Hybridizing polynucleotides are useful as diagnostic probes and primers as discussed above. Portions of a polynucleotide which hybridizes to the p62 polypeptide, which can be used as probes and primers, may be precisely specified by 5' and 3' base positions or by size in nucleotide bases as described above or precisely excluded in the same manner. Similarly, portions of a polynucleotide which hybridize to the ubiquitin polypeptide may be used as probes and primers as well. Preferred hybridizing polynucleotides of the present invention are those that, when labeled and used in a hybridization assay known in the art (e.g. Southern and Northern blot analysis), display the greatest signal strength regardless of other heterologous sequences present in equimolar amounts.

Variant and Mutant Polynucleotides

The present invention further relates to variants of the nucleic acid molecules, which encode portions, analogs or derivatives of p62 polypeptide or ubiquitin polypeptide, which retain the capability of specifically binding to p62 and ubiquitin, respectively, which is also optionally non-functional in at least one other aspect, so long as the variant competitively or non-competitively disrupts p62/ubiquitin binding, without causing toxic side effects. Non-naturally occurring variants may be produced using art-known mutagenesis techniques.

Such nucleic acid variants include those produced by nucleotide substitutions, deletions, or additions. The substitutions, deletions, or additions may involve one or more nucleotides. Alterations in the amino acid sequence may produce conservative or non-conservative amino acid substitutions, deletions or additions. Especially preferred among these are silent substitutions, additions and deletions, which do not alter the properties and activities of the polypeptides of the present invention or portions thereof. Also preferred in this regard are conservative substitutions.

The invention allows for the use of sequences in expression vectors, as well as to transfect host cells and cell lines, be these prokaryotic or eukaryotic cells. The invention also allows for purification of the polypeptides expressed from the expression vector. The expression vector may contain various molecular tags for easy purification. Subsequently obtained expression construct may be transformed into any host cell of choice. Cell lysates from the host cell is isolated by established methods well known in the field. GFP- or GST-containing expression vector may be used to localize p62 polypeptide or ubiquitin polypeptide in the host cell. The expression vector may contain an inducible or constitutive promoter.

Variant and Mutant Polypeptides

To improve or alter the characteristics of p62 polypeptide or ubiquitin polypeptide of the present invention, amino acid engineering may be employed. Recombinant DNA technology known to those skilled in the art can be used to create novel mutant polypeptides including single or multiple amino acid substitutions, deletions, additions, or fusion proteins. Such modified polypeptides can show, e.g., increased/decreased binding activity or increased/decreased stability. In addition, they may be purified in higher yields and show better binding activity than the corresponding natural polypeptide, at least under certain purification and storage conditions.

Of special interest are substitutions of charged amino acids with other charged or neutral amino acids which may produce proteins with highly desirable improved characteristics, such as less aggregation of the produced polypeptides. Aggregation may not only reduce activity but may also be problematic when preparing pharmaceutical formulations, because aggregates can be immunogenic.

Antibodies

In one embodiment, the present invention is directed to detecting inclusion body or sequestosome formation using a variety of detection methods. One way to detect binding of p62 polypeptide to ubiquitin is to label the p62 polypeptide directly and assay for its binding using labeling and separation techniques that are routine to a person of skill in the art. Other methods include using a labeled ligand that specifically binds to either the p62 polypeptide, ubiquitin or p62 polypeptide/ubiquitin complex. Such a ligand may be an antibody.

Purified p62 polypeptide, ubiquitin or p62 polypeptide/ubiquitin complex can be used to produce monoclonal or polyclonal antibody. Fragments of p62 polypeptide also can be used to produce monoclonal or polyclonal antibody. Subsequently obtained monoclonal or polyclonal antibody can be used to determine the binding of p62 polypeptide to ubiquitin and the formation of a p62 polypeptide, ubiquitin or p62 polypeptide/ubiquitin complex in various samples including cells, tissues, and body fluids such as but not limited to serum, plasma, and urine. p62 polypeptide, ubiquitin or p62 polypeptide/ubiquitin complex may be assayed using a variety of molecular biological methods, which include but are not limited to in situ hybridization, immunoprecipitation, immunofluorescence staining, Western blot analysis and so on. One can carry out ELISA by using monoclonal antibody against p62 polypeptide, ubiquitin or p62 polypeptide/ ubiquitin complex, to determine the amount of inclusion body in the brain tissue or other parts of the body, including body fluids of human subjects believed to have an indicated disorder in which p62 and ubiquitin is aggregated and is accumulated and form inclusion bodies.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material.

Antibodies of the present invention may be described or specified in terms of the epitope(s) or portion(s) of a polypeptide of the present invention, which they recognize or specifically bind. The epitope(s) or polypeptide portion(s) may be specified as described herein, e.g., by N-terminal and C-terminal positions, by size in contiguous amino acid residues.

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of p62 polypeptide, ubiquitin or p62 polypeptide/ubiquitin complex of the present invention in biological samples.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins.

The antibodies of the present invention may be generated by any suitable method known in the art. Polyclonal antibodies to an antigen of interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with a p62 polypeptide, ubiquitin or p62 polypeptide/ubiquitin complex or a cell expressing such entity. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention or its complex with its binding partner. Ascites fluid, which generally contains high levels of antibodies, can be generated by immunizing mice with positive hybridoma clones.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Assays for Antibody Binding

The antibodies of the invention may be assayed for immunospecific binding by any method known in the art. The immunoassays which can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below but are not intended by way of limitation.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horse radish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, which may include a sample comprising p62 polypeptide, ubiquitin or p62 polypeptide/ubiquitin, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added simultaneously or following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Inclusion Body Diagnostic Assay

The invention also provides diagnostic methods for detecting the presence of inclusion body in a biological sample. This may be assayed either directly (e.g., by assaying polypeptide levels using antibodies elicited in response to p62 polypeptide or fragments thereof) or indirectly (e.g., by assaying for antibodies having specificity for p62 polypeptide or fragments thereof).

Where diagnosis of a diseased state has already been made, the present invention is useful for monitoring progression or regression of the disease state by measuring the amount of ubiquitin/p62 complex present in a patient or whereby patients exhibiting enhanced inclusion body production will experience a worse clinical outcome relative to patients producing inclusion body at a lower level.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography, as well as electron paramagnetic resonance (EPR) and nuclear magnetic resonance (NMR).

In a specific embodiment, a molecule such as a polypeptide that specifically binds to ubiquitin is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

In one aspect, the iii vivo diagnosis may be made by using a label that is detectable by the above described methods or some other mechanism, which is non-toxic to the subject, injecting the labeled polypeptide into a subject such that the polypeptide travels and binds to its binding target, such as an aggregated region, whereby the presence of the target mass, such as ubiquitin or inclusion body aggregate is detected.

Labels

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Further suitable labels for the p62 polypeptide-, ubiquitin- or p62 polypeptide/ubiquitin complex-specific antibodies of the present invention are provided below. Examples of suitable enzyme labels include malate dehydrogenase, δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include 3H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is preferred isotope where in vivo imaging is used since its avoids the problem of dehalogenation of the $^{125}$I or $^{131}$I-labeled polypeptide by the liver. In addition, this radionucleotide has a more favorable gamma emission energy for imaging. For example, $^{111}$In coupled to monoclonal antibodies with 1-(P-isothiocyanatobenzyl)-DPTA has shown little uptake in non-tumors tissues, particularly the liver, and therefore enhances specificity of tumor localization.

Examples of suitable non-radioactive isotopic labels include $^{157}$Gd, $^{55}$Mn, $^{162}$Dy, $52^{Tr}$, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, Pseudomonas toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron. Deuterium may also be used. Other contrasting agents also exist for EPR, PET or other imaging mechanisms, which are known to persons of skill in the art.

Typical techniques for binding the above-described labels to polypeptides are provided by Kennedy et al. (1976) Clin. Chim. Acta 70:1-31, and Schurs et al. (1977) Clin. Chim. Acta 81:1-40. Coupling techniques include the glutaraldehyde method, the periodate method, the dimaleimide method, the m-maleimidobenzyl-N-hydroxy-succinimide ester method, all of which methods are incorporated by reference herein.

The polypeptides and antibodies of the present invention, including fragments thereof, may be used to detect p62 polypeptide, ubiquitin or p62 polypeptide/ubiquitin complex using biochip and biosensor technology. Biochip and biosensors of the present invention may comprise the polypeptides of the present invention to detect antibodies, which specifically recognize p62 polypeptide/ubiquitin complex. Bio chip and biosensors of the present invention may also comprise antibodies which specifically recognize the polypeptides of the present invention to detect p62 polypeptide/ubiquitin complex. In addition, the invention also contemplates an array, such as a microarray or macroarray chip, which comprises p62 nucleic acid, preferably oligonucleotides, and preferably antisense oligonucleotides that may be used to detect or hybridize to wild-type or mutant p62 transcript that may be present in an assayable sample such as a biological sample. Such array structures are well-known.

Inclusion Body Detection Kit

The invention also includes a kit for analyzing samples for the presence of p62 polypeptide/ubiquitin complex in a biological sample. In a general embodiment, the kit comprises ligand which binds specifically to p62 polypeptide, ubiquitin or p62 polypeptide/ubiquitin complex, which may be preferably a purified antibody to p62 polypeptide, or p62 polypeptide/ubiquitin complex, in one or more containers. In a specific embodiment, the kit of the present invention contains a substantially isolated polypeptide comprising an epitope which is specifically immunoreactive with an antibody included in the kit. Preferably, the kit of the present invention further comprises a control antibody which does not react with the polypeptide of interest. The kit further comprises instructions and labels on its use.

In another specific embodiment, the kit of the present invention contains a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate), and instructions and labels on its use. The kit may also contain labeled p62 polypeptide with instructions for its use as an inclusion body detector.

Transgenic Animals and Cell Lines

The present invention provides for various animals that have been produced with germ line foreign DNA, or with altered levels of expression of certain genes. These animals typically have a foreign or mutated gene incorporated into their genome. In one such class of transgenic animal, the so-called homozygous null or "knockout" mutants, expression of an endogenous gene has been suppressed through genetic manipulation.

Also provided in the present invention is a mammalian cell line, which is heterozygous or homozygous for a deficiency in the normal synthesis of p62. In one embodiment of the invention, the cell line does not synthesize detectable levels of p62. In another embodiment, the cell line does not synthesize functional p62. The invention further provides for a cell line that is deficient in the normal synthesis of p62. The cell line may be derived from a pluripotent cell line.

The transgenic animals may be either homozygous or heterozygous for the genetic alteration. The subject animals are useful for testing candidate agents for treatment of individuals diagnosed with aging related disorder, either prophylactically or after disease onset.

Transgenic animals generally harbor at least one copy of a transgene either homologously or nonhomologously integrated into an endogenous chromosomal location so as to encode a foreign or mutant protein. Such transgenic animals are usually produced by introducing the transgene or targeting construct into a fertilized egg, or into an embryonic stem (ES) cell which is then injected into an embryo. Introduction of the transgene into the fertilized egg or ES cell is typically performed by microinjection, retroviral infection, electroporation, lipofection, or biolistics. The fertilized egg or embryo is then transferred to an appropriate pseudopregnant female for the duration of gestation. Knockout mutants may be obtained according to this method where the non-native DNA which is introduced comprises a nucleic acid construct that will be used to suppress expression of a particular gene. Such knockout constructs are typically introduced into ES cells.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the genline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

Chimeric targeted mice may be derived according to Hogan, et al., Manipulating the Mouse Embryo: A Laboratory Manual, Cold Spring Harbor Laboratory (1988) and Teratocarcinomas and Embryonic Stem Cells: A Practical Approach, E. J. Robertson, ed., IRL Press, Washington, D.C., (1987) which are incorporated herein by reference.

Embryonic stem cells may be manipulated according to published procedures (Teratocarcinomas and Embryonic Stem Cells: A Practical Approach, E. J. Robertson, ed., IRL Press, Washington, D.C. (1987); Zjilstra et al., Nature 342: 435-438 (1989); and Schwartzberg et al., Science 246:799-803 (1989), each of which is incorporated herein by reference).

According to the practice of the invention, the endogenous p62 alleles of a cell line or nonhuman animal are functionally disrupted so that expression of endogenously encoded p62 gene is suppressed or eliminated.

For making transgenic non-human animals (which include homologously targeted non-human animals), embryonal stem cells (ES cells) are preferred. Murine ES cells, such as AB-1 line grown on mitotically inactive SNL76/7 cell feeder layers (McMahon and Bradley (1990) Cell 62: 1073) essentially as described (Robertson, E. J. (1987) in Teratocarcinomas and Embryonic Stein Cells: A Practical Approach. E. J. Robertson, ed. (Oxford: IRL Press), p. 71-112) may be used for homologous gene targeting. Other suitable ES lines include but are not limited to, the E14 line (Hooper et al. (1987) Nature 326: 292-295), the D3 line (Doetschman et al. (1985) J. Embryol. Exp. Morphi. 87: 27-45), and the CCE line (Robertson et al. (1986) Nature 323: 445-448). The practice of the present invention is specifically exemplified hereinafter using ES cells of mouse strain 129/J (Jackson Laboratories). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having an inactivated endogenous p62 locus and are back-crossed and screened for the presence of the correctly targeted transgene(s) by PCR or Southern blot analysis on tail biopsy DNA of offspring so as to identify transgenic mice-heterozygous for the inactivated p62. By performing the appropriate crosses, it is possible to produce a transgenic nonhuman animal homozygous for functionally disrupted p62 alleles. Such transgenic animals are substantially incapable of making an endogenous p62 gene product.

The functionally disrupted p62 homozygous null mutant transgenic animals will typically comprise rats or mice, but nonmurine species such as dogs, cattle, sheep, goats, pigs and nonhuman primates, for example, may be utilized.

The p62−/− mammals of the invention may be utilized as a model for studying aging related disorders or diseases. In addition, the p62−/− animals may be used in the screening of potential therapeutic synthetic p62 peptides. Such peptides could be screened for the ability to induce the anti-aging related disorder phenotype upon local administration to the p62−/− mice. The candidate peptide would be administered locally by injection into the p62−/− mice.

The practice of the present invention is exemplified herein using the neo gene as the transgene. It may be appreciated that it is possible to generate nonhuman animals which harbor any desired transgene, provided the transgene may be contained in a construct further including a wild type p62 gene.

Gene Targeting Construct

Gene targeting, which is a method of using homologous recombination to modify a mammalian genome, can be used to introduce genetic changes into cultured cells. By targeting a gene of interest in embryonic stem (ES) cells, these changes can be introduced into the germlines of laboratory animals to study the effects of the modifications on whole organisms, among other uses. The gene targeting procedure is accomplished by introducing into tissue culture cells a DNA targeting construct that has a segment homologous to a target locus and which also comprises an intended sequence modification (e.g., insertion, deletion, point mutation). The treated cells are then screened for accurate targeting to identify and isolate those which have been properly targeted. A common scheme to disrupt gene function by gene targeting in ES cells is to construct a targeting construct which is designed to undergo a homologous recombination with its cliromosomal counterpart in the ES cell genome. The targeting constructs are typically arranged so that they insert an additional sequence, such as a positive selection marker, into coding elements of the target gene, thereby functionally disrupting it. Targeting constructs usually are insertion-type or replacement-type constructs (Hasty et al. (1991) Mol. Cell. Biol. 11: 4509).

The invention encompasses production of stem cells and nonhuman animals that have the endogenous p62 gene inactivated by gene targeting with a homologous recombination targeting construct. The p62 gene sequence may be used as a basis for producing PCR primers that flank a region that will be used as a homology clamp in a targeting construct. The PCR primers are then used to amplify a genomic sequence from a genomic clone library or from a preparation of genomic DNA, preferably from the strain of nonhuman animal that is to be targeted with the targeting construct. The amplified DNA is then used as a homology clamp and/or targeting region. General principles regarding the construction of targeting constructs and selection methods are reviewed in Bradley et al. (1992) Bio/Technology 10: 534, incorporated herein by reference.

The isolation of p62 genomic DNA useful for this purpose is described herein. Appropriate probes may be designed based on known p62 cDNA nucleotide sequences. For example, the complete nucleotide sequence of human p62 cDNA and its deduced amino acid sequence are disclosed in U.S. Pat. Nos. 6,291,645B1 and 5,962,224, which are incorporated by reference herein in their entirety.

Targeting constructs can be transferred into pluripotent stem cells, such as ES cells, wherein the targeting constructs homologously recombine with a portion of the endogenous p62 gene locus and create mutation(s) (i.e., insertions, deletions, rearrangements, sequence replacements, and/or point mutations) which prevent the functional expression of the endogenous p62 gene.

One method is to delete, by targeted homologous recombination, essential structural elements of the endogenous p62 gene. For example, a targeting construct can homologously recombine with an endogenous p62 gene and delete a portion spanning substantially all of one or more exons to create an exon-depleted allele, typically by inserting a replacement region lacking the corresponding exon(s). Transgenic animals homozygous for the exon-depleted allele (e.g., by breeding of heterozygotes to each other) are essentially incapable of expressing a functional endogenous p62 polypeptide. Similarly, homologous gene targeting can be used, if desired, to functionally disrupt the p62 gene by deleting only a portion of an exon.

Targeting constructs can also be used to delete essential regulatory elements of the endogenous p62 gene, such as promoters, enhancers, splice sites, polyadenylation sites, and other regulatory sequences, including cis-acting sequences that may occur upstream or downstream of the p62 structural gene but which participate in endogenous p62 gene expression. Deletion of regulatory elements is typically accomplished by inserting, by homologous double-crossover recombination, a replacement region lacking the corresponding regulatory element(s).

A preferred method is to interrupt essential structural and/or regulatory elements of the endogenous p62 gene by targeted insertion of a polynucleotide sequence, and thereby functionally disrupt the endogenous p62 gene. For example, a targeting construct can homologously recombine with the endogenous p62 gene and insert a nonhomologous sequence, such as a neo expression cassette into a structural element (e.g., an exon) and/or regulatory element (e.g., enhancer, promoter, splice site, polyadenylation site) to yield a targeted p62 allele having an insertional interruption. The inserted sequence can range in size from about 1 nucleotide (e.g., to produce a frameshift in an exon sequence) to several kilobases or more, as limited by efficiency of homologous gene targeting with targeting constructs having a long nonhomologous replacement region.

Figure 2:
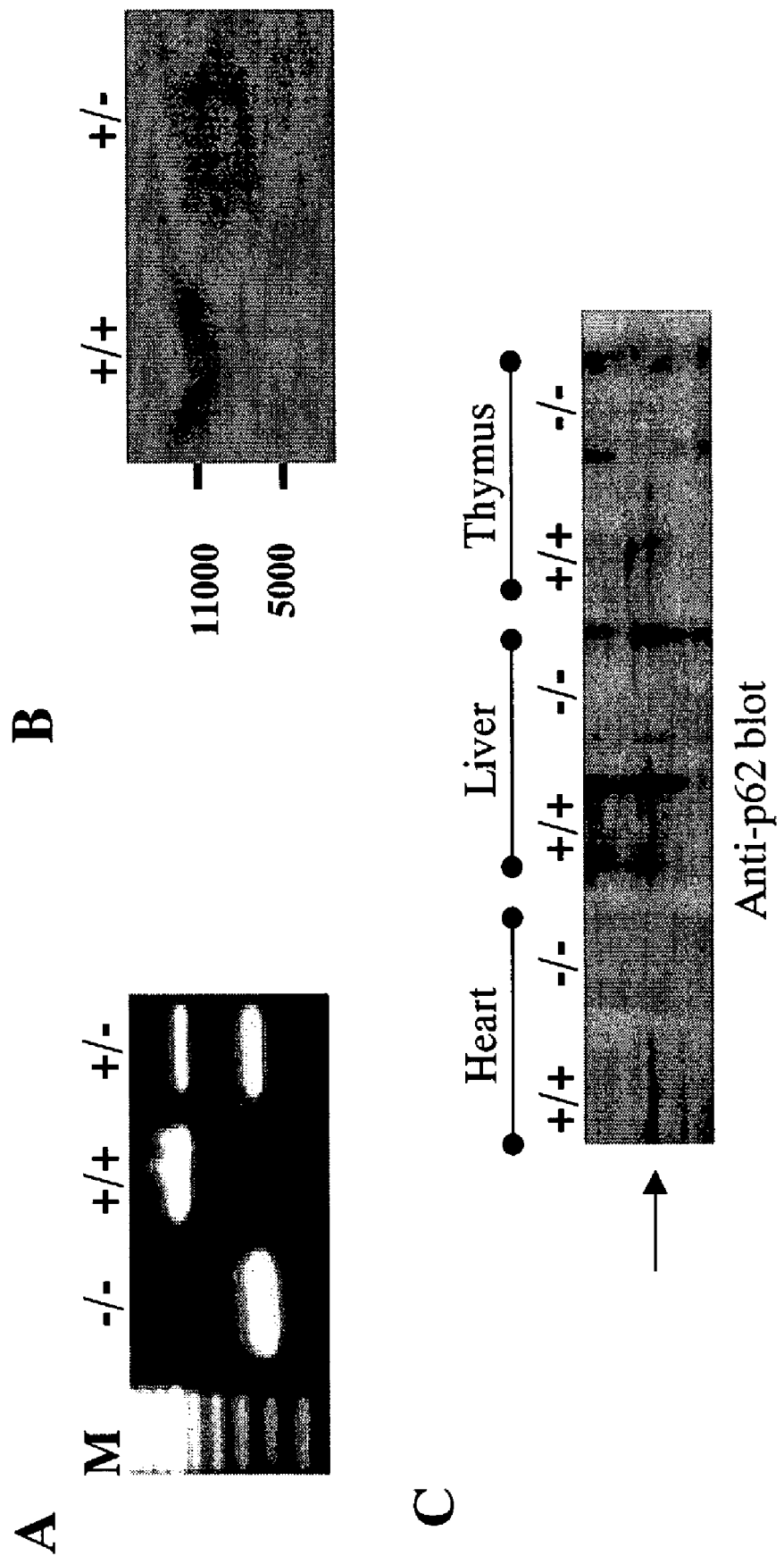
FIGS. 2A-2C show p62 genotypic analysis. (A) PCR analysis of litters derived heterozygotes intercross: +/+, wild-type; ±, heterozygous; −/−, homozygous. (B) Southern blot analysis. (C) Immunoblot analysis of extracts from wild or null p62 mice organs.

One preferred target site is as indicated in FIG. 1, and confirmed as shown in FIG. 2.

Targeting constructs can also be employed to replace a portion of the endogenous p62 gene with an exogenous sequence (i.e., a portion of a targeting transgene); for example, a first exon of a p62 gene may be replaced with a substantially identical portion that contains a nonsense or missense mutation.

A targeting construct may be transferred by electroporation of microinjection into a totipotent ES cell line. The targeting construct homologously recombines with endogenous sequences in or flanking of the p62 gene locus and functionally disrupts at least one allele of the p62 gene. Typically, homologous recombination of the targeting construct with endogenous p62 locus sequences will result in integration of a nonhomologous sequence encoding and expressing a selectable marker, such as neo, usually in the form of a positive selection cassette. ES cells having at least one such p62 null allele are selected for by propagating the cells in a medium that permits the preferential propagation of cells expressing the selectable marker. Selected ES cells are examined by PCR analysis and/or Southern blot analysis to verify the presence of a correctly targeted p62 allele. Breeding of nonhuman animals which are heterozygous for a null allele may be performed to produce nonhuman animals homozygous for said null allele, so-called "knockout" animals (Donehower et al. (1992) Nature 256: 215; Science 256: 1392, incorporated by reference). Alternatively, ES cells homozygous for a null allele having an integrated selectable marker can be produced in culture by selection in a medium containing high levels of the selection agent (e.g., G418 or hygromycin). Heterozygosity and/or homozygosity for a correctly targeted null allele can be verified with PCR analysis and/or Southern blot analysis of DNA isolated from an aliquot of a selected ES cell clone and/or from tail biopsies.

Gene targeting techniques which have been described, include but are not limited to: co-electroporation, "hit-and-run", single-crossover integration, and double-crossover recombination (Bradley et al. (1992) Bio/Technology 10: 534). The preparation of the homozygous p62 null mutants can be practiced using essentially any applicable homologous gene targeting strategy known in the art. The configuration of a targeting construct depends upon the specific targeting technique chosen. For example, a targeting construct for single-crossover integration or "hit-and-run" targeting need only have a single homology clamp linked to the targeting region, whereas a double-crossover replacement-type targeting construct requires two homology clamps, one flanking each side of the replacement region.

For example and not by way of limitation, a targeting construct may comprise: (1) a first homology clamp having a sequence substantially identical to a sequence within about 3 kilobases upstream (i.e., in the direction opposite to the translational reading frame of the exons) of an exon of an endogenous p62 gene, (2) a replacement region comprising a positive selection cassette having a pgk promoter driving transcription of a neo gene, (3) a second homology clamp having a sequence substantially identical to a sequence within about 3 kilobases downstream of said exon of said endogenous p62 gene, and (4) a negative selection cassette, comprising a pgk promoter driving transcription of an HSV tk gene. Such a targeting construct is suitable for double-crossover replacement recombination which deletes a portion of the endogenous p62 locus spanning the exon and replaces it with the replacement region having the positive selection cassette. The deleted exon is one which is essential for expression of a functional p62 gene product. Thus, the resultant exon-depleted allele is functionally disrupted and is termed a null allele.

Targeting constructs comprise at least one homology clamp linked in polynucleotide linkage (i.e., by phosphodiester bonds) to a targeting region. A homology clamp has a sequence which substantially corresponds to, or is substantially complementary to, an endogenous p62 gene sequence of a nonhuman host animal, and may comprise sequences flanking the p62 gene.

Although no lower or upper size boundaries for recombinogenic homology clamps for gene targeting have been conclusively determined in the art, the best mode for homology clamps is believed to be in the range between about 50 bp and several tens of kilobases. Consequently, targeting constructs are generally at least about 50 to 100 nucleotides long, preferably at least about 250 to 500 nucleotides long, more preferably at least about 1000 to 2000 nucleotides long, or longer. Construct homology regions (homology clamps) are generally at least about 50 to 100 bases long, preferably at least about 100 to 500 bases long, and more preferably at least about 750 to 2000 bases long. It is believed that homology regions of about 7 to 8 kilobases in length are preferred with one preferred embodiment having a first homology region of about 7 kilobases flanking one side of a replacement region and a second homology region of abut 1 kilobase flanking the other side of said replacement region. The length of homology (i.e., substantial identity) for a homology region may be selected at the discretion of the practitioner on the basis of the sequence composition and complexity of the endogenous p62 gene target sequence(s) and guidance provided in the art. Targeting constructs have at least one homology region having a sequence that substantially corresponds to, or is substantially complementary to, an endogenous p62 gene sequence (e.g., an exon sequence, an enhancer, a promoter, an intronic sequence, or a flanking sequence within about 3-20 kb of the p62 gene). Such a targeting construct homology region serves as a template for homologous pairing and recombination with substantially identical endogenous p62 gene sequence(s). In targeting constructs, such homology regions typically flank the replacement region, which is a region of the targeting construct that is to undergo replacement with the targeted endogenous p62 gene sequence. Thus, a segment of the targeting construct flanked by homology regions can replace a segment of an endogenous p62 gene sequence by double-crossover homologous recombination. Homology regions and targeting regions are linked together in conventional linear polynucleotide linkage (5' to 3' phosphodiester backbone). Targeting constructs are generally double-stranded DNA molecules, most usually linear.

Homology regions are generally used in the same orientation (i.e., the upstream direction is the same for each homology region of a transgene to avoid rearrangements). Double-crossover replacement recombination thus can be used to delete a portion of the endogenous p62 and concomitantly transfer a nonhomologous portion (i.e., a neo gene expression cassette) into the corresponding chromosomal location. Double-crossover recombination can also be used to add a nonhomologous portion into the endogenous p62 gene without deleting endogenous chromosomal portions. However, double-crossover recombination can also be employed simply to delete a portion of an endogenous gene sequence without transferring a nonhomologous portion into the endogenous p62 gene. Upstream and/or downstream from the nonhomologous portion may be a gene which provides for identification of whether a double-crossover homologous recombination has occurred; such a gene is typically the HSV tk gene which may be used for negative selection.

Typically, targeting constructs used for functionally disrupting endogenous p62 gene will comprise at least two homology regions separated by a nonhomologous sequence which contains an expression cassette encoding a selectable marker, such as neo (Smith and Berg (1984) Cold Spring Harbor Symp. Quant. Biol. 49: 171; Sedivy and Sharp (1989) Proc. Natl. Acad. Sci. (U.S.A.) 86: 227; Thomas and Capechi (1987), Cell 51: 503). However, some targeting transgenes may have the homology region(s) flanking only one side of a nonhomologous sequence. Targeting transgenes of the invention may also be of the type referred to in the art as "hit-and-run" or "in-and-out" transgenes (Valancius and Smithies (1991) Mol. Cell. Biol. 11: 1402; Donehower et al. (1992) Nature 356: 215; (1991) J.NIH Res. 3: 59; which are incorporated herein by reference).

The positive selection expression cassette encodes a selectable marker which affords a means for selecting cells which have integrated targeting transgene sequences spanning the positive selection expression cassette. The negative selection expression cassette encodes a selectable marker which affords a means for selecting cells which do not have an integrated copy of the negative selection expression cassette. Thus, by a combination positive-negative selection protocol, it is possible to select cells that have undergone homologous replacement recombination and incorporated the portion of the transgene between the homology regions (i.e., the replacement region) into a chromosomal location by selecting for the presence of the positive marker and for the absence of the negative marker (Valancius and Smithies, supra).

An expression cassette typically comprises a promoter which is operational in the targeted host cell (e.g., ES cell) linked to a structural sequence that encodes a protein or polypeptide that confers a selectable phenotype on the targeted host cell, and a polyadenylation signal. A promoter included in an expression cassette may be constitutive, cell type-specific, stage-specific, and/or modulatable (e., by hormones such as glucocorticoids; MMTV promoter), but is expressed prior to and/or during selection. An expression cassette can optionally include one or more enhancers, typically linked upstream of the promoter and within about 3-10 kilobases. However, when homologous recombination at the targeted endogenous site(s) places the nonhomologous sequence downstream of a functional endogenous promoter, it may be possible for the targeting construct replacement region to comprise only a structural sequence encoding the selectable marker, and rely upon the endogenous promoter to drive transcription (Doetschman et al. (1988) Proc. Natl. Acad. Sci. (U.S.A.) 85: 8583; incorporated herein by reference). Similarly, an endogenous enhancer located near the targeted endogenous site may be relied on to enhance transcription of transgene sequences in enhancerless transgene constructs.

Preferred expression cassettes for inclusion in the targeting constructs encode and express a selectable drug resistance marker and/or a HSV thymidine kinase (tk) enzyme. Suitable drug resistance genes include, for example: gpt (xanthine-guanine phosphoribosyltransferase), which can be selected for with mycophenolic acid; neo (neomycin phosphotransferase), which can be selected for with G418 or hygromycin; and DFHR (dihydrofolate reductase), which can be selected for with methotrexate (Nulligan and Berg (1981) Proc. Natl. Acad. Sci. (U.S.A.) 78: 2072; Southern and Berg (1982) J. Mol. Appl. Genet. 1: 327; which are incorporated herein by reference).

Selection for correctly targeted recombinants will generally employ at least positive selection, wherein a nonhomologous expression cassette encodes and expresses a functional protein (e.g., neo or gpt) that confers a selectable phenotype to targeted cells harboring the endogenously integrated expression cassette, so that, by addition of a selection agent (e.g., G418 or mycophenolic acid) such targeted cells have a growth or survival advantage over cells which do not have an integrated expression cassette.

It is preferable that selection for correctly targeted homologous recombinants also employ negative selection, so that cells bearing only nonhomologous integration of the transgene are selected against. Typically, such negative selection employs an expression cassette encoding the herpes simplex virus thymidine kinase gene (HSV tk) positioned in the transgene so that it should integrate only by nonhomologous recombination. Such positioning generally is accomplished by linking the HSV tk expression cassette (or other negative selection cassette) distal to the recombinogenic homology regions so that double-crossover replacement recombination of the homology regions transfers the positive selection expression cassette to a chromosomal location but does not transfer the HSV tk gene (or other negative selection cassette) to a chromosomal location. A nucleoside analog, ganciclovir, which is preferentially toxic to cells expressing HSV tk, can be used as the negative selection agent, as it selects for cells which do not have an integrated HSV tk expression cassette. FIAU may also be used as a selective agent to select for cells lacking HSV tk.

In order to reduce the background of cells having incorrectly integrated targeting construct sequences, a combination positive-negative selection scheme is typically used (Mansour et al., Nature 336: 348-352 (1988) incorporated herein by reference). Positive-negative selection involves the use of two active selection cassettes: (1) a positive one (e.g., the neo gene), that can be stably expressed following either random integration or homologous targeting, and (2) a negative one (e.g., the HSV tk gene), that can only be stably expressed following random integration, and cannot be expressed after correctly targeted double-crossover homologous recombination. By combining both positive and negative selection steps, host cells having the correctly targeted homologous recombination between the transgene and the endogenous p62 gene can be obtained.

Generally targeting constructs preferably include: (1) a positive selection expression cassette flanked by two homology regions that are substantially identical to host cell endogenous p62 gene sequences, and (2) a distal negative selection expression cassette. However, targeting constructs which include only a positive selection expression cassette can also be used. Typically, a targeting construct will contain a positive selection expression cassette which includes a neo gene linked downstream (i.e., towards the carboxy-terminus of the encoded polypeptide in translational reading frame orientation) of a promoter such as the HSV tk promoter or the pgk promoter. More typically, the targeting transgene will also contain a negative selection expression cassette which includes an HSV tk gene linked downstream of a pgk promoter.

Typically, targeting polynucleotides of the invention have at least one homology region that is at least about 50 nucleotides long, and it is preferable that homology regions are at least about 75 to 100 nucleotides long, and more preferably at least about 200-2000 nucleotides long, although the degree of sequence homology between the homology region and the targeted sequence and the base composition of the targeted sequence will determine the optimal and minimal homology region lengths (e., G—C rich sequences are typically more thermodynamically stable and will generally require shorter homology region length). Therefore, both homology region length and the degree of sequence homology can only be determined with reference to a particular predetermined sequence, but homology regions generally must be at least about 50 nucleotides long and must also substantially correspond or be substantially complementary to a predetermined endogenous target sequence. Preferably, a homology region is at least about 100 nucleotides long and is identical to or complementary to a predetermined target sequence in or flanking the p62 gene. If it is desired that correctly targeted homologous recombinants are generated at high efficiency, it is preferable that at least one homology region is isogeneic (i.e., has exact sequence identity with the crossover target sequence(s) of the endogenous p62 gene), and is more preferred that isogeneic homology regions flank the exogenous targeting construct sequence that is to replace the targeted endogenous p62 sequence.

The p62 sequence may be scanned for possible disruption sites. Plasmids are engineered to contain an appropriately sized construct replacement sequence with a deletion or insertion in the p62 gene and at least one flanking homology region which substantially corresponds or is substantially complementary to an endogenous target DNA sequence. Typically, two flanking homology regions are used, one on each side of the replacement region sequence.

The p62 gene is inactivated by homologous recombination in a pluripotent cell line that is capable of differentiating into germ cell tissue. A DNA construct, as discussed above, that contains an altered copy of a mouse p62 gene is introduced into the nuclei of ES cells. In a portion of the cells, the introduced DNA recombines with the endogenous copy of the mouse p62 gene, replacing it with the altered copy. Cells containing the newly engineered genetic lesion are injected into a host mouse embryo, which is reimplanted into a recipient female. Some of these embryos develop into chimeric mice that possess germ cells derived from the mutant cell line. Therefore, by breeding the chimeric mice it is possible to obtain a new line of mice containing the introduced genetic lesion.

Vectors containing a targeting construct are typically grown in *E. coli* and then isolated using standard molecular biology methods, or may be synthesized as oligonucleotides. Direct targeted inactivation which does not require prokaryotic or eukaryotic vectors may also be performed. Targeting constructs can be transferred to host cells by any suitable technique, including microinjection, electroporation, lipofection, biolistics, calcium phosphate precipitation, and viral-based vectors, among others. Other methods used to transform mammalian cells include the use of Polybrene, protoplast fusion, and others (e.g., generally, Sambrook et al. Molecular Cloning: A Laboratory Manual, 2d ed., 1989, Cold Spring Harbor Laboratory Press, Cold Spring Harbor, N.Y., which is incorporated herein by reference).

Screening Methods for p62 Interacting Factors

A number of methods for screening candidate factors that interact with the p62 gene or gene product are well-known in the art, and will allow one of ordinary skill to determine if a compound is useful in the present invention.

The agent can be selected and screened at random, or can be rationally selected or rationally designed using protein modeling techniques.

For random screening, agents such as, but not limited to, peptides, carbohydrates, steroids or vitamin derivatives are selected at random and are assayed, using direct or indirect methods that are routine in the art, for their ability to bind to p62 gene or gene product that is present in mice or cell lines described in the present invention. Alternatively, agents can be assayed for modulation of the aging related disorder.

Routine assays may be used to screen compounds for their effect on p62 gene expression and p62 protein function. For example, a transient expression/gel retardation system may be used to study the effects of agents such as synthetic steroids or natural herbal extracts.

In another screening assay, transgenic animals, e.g., mice, and cell lines, that are altered in their expression of one or more of p62 genes may be made, and may be used to identify factors, which modulate the expression and function of p62 gene product. In such an assay, the agent which is to be tested may be incubated with one or more of the transgenic cell lines or mice or tissues derived therefrom. The level of binding of the agent is then determined, or the effect the agent has on biological effect or gene expression is monitored, by techniques that are routine to those of ordinary skill. As used herein, the term "incubate" is defined as contacting the compound or agent under investigation with the appropriate cell or tissue, or administering the agent or compound to the appropriate animal, e.g., transgenic mouse, via any one of the well-known routes of administration including enteral, intravenous, subcutaneous, and intramuscular.

Other assays may include immunological techniques such as immunofluorescent or immunoelectron microscopy, using antibodies specific for p62 fusion proteins. p62 interacting may also be identified by their abilities to modulate the in vitro aging related phenotypes. The agents screened can be, but are not limited to peptides, carbohydrates, steroids, herbal extracts, and vitamin derivatives.

Molecules which can modulate (induce, enhance, reduce, or abolish) p62-positive inclusions can be screened in the cells or cell lines expressing p62 by treating cells with proteasomal inhibitors or oxidative stress including ROS generators or redox modifiers.

Detection of changes in the p62 locus of human genome including deletion, rearrangement, mutation or single nucleotide polymorphism may be used to predict susceptibility to or diagnose the p62-defect related diseases such as obesity, type-2 diabetes, various cancers and neurodegenerative diseases, and early death of male.

Drug Screening Assays for Treating Aging-Related Disease

The animals of the invention can be used as tester animals for materials of interest, e.g. antioxidants such as Vitamin E, thought to confer protection against the development of aging related disorders. An animal is treated with the material of interest, and a reduced incidence or delayed onset of aging related disease, as compared to untreated animals, is detected as an indication of protection. The indices used preferably are those which can be detected in a live animal. The effectiveness can be confirmed by effects on pathological changes when the animal dies or is sacrificed. The animals further can be used as tester animals for materials of interest thought to improve or cure aging related disorder or disease. For instance, an animal with a disease related to the red-ox state of the body may be treated with the material of interest, and a delayed death, or improvement in body weight, fat deposit or glucose uptake/utilization, as compared to untreated animals with aging related disease, is detected as an indication of amelioration or cure.

Through use of the subject transgenic animals or cells derived therefrom, one can identify ligands or substrates that modulate phenomena associated with aging related disorder. Of particular interest are screening assays for agents that have a low toxicity for human cells.

A wide variety of assays may be used for this purpose, including behavioral studies, determination of the localization of drugs after administration, immunoassays to detect amyloid deposition, and the like. Depending on the particular assay, whole animals may be used, or cells derived therefrom. Cells may be freshly isolated from an animal, or may be immortalized in culture. Cells of particular interest are derived from neural tissue.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: herbal extracts, peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art.

For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

A number of assays are known in the art for determining the effect of a drug on animal behavior and other phenomena associated with aging related disorders. Some examples are provided, although it will be understood by one of skill in the art that many other assays may also be used. The subject animals may be used by themselves, or in combination with control animals. The screen using the transgenic animals of the invention can employ any phenomena associated with aging related diseases that can be readily assessed in an animal model. Preferably, the screen will include control values.

Therapeutic Composition

In one embodiment, the present invention relates to treatment for various diseases that are characterized as aging related disease as defined in the present application. In this way, the inventive therapeutic compound may be administered to human patients who are either suffering from disorders, such as obesity, diabetes, cancer, in particular, liver cancer, fatty liver, and Paget Disease of Bone, and early mortality for males harboring p62 homozygous mutation.

The formulation of therapeutic compounds is generally known in the art and reference can conveniently be made to Remington's Pharmaceutical Sciences, 17th ed., Mack Publishing Co., Easton, Pa., USA. For example, from about 0.05 µg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and marmer of administration of the said ingredients.

Delivery Systems

Various delivery systems arc known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose.

Diagnosis of Aging Related Disease

The invention is also directed to a method to assist in the diagnosis of subsceptibility to aging-related disease such as obesity, Type II diabetes, hepatocarcinoma, early male mortality, in a mammalian subject, comprising comparing the wild-type gene encoding p62 with the subject's p62 gene. The detection of a point mutation, single nucleotide polymorphism, deletion, frameshift mutation, rearrangement, truncation or disruption of the gene such that its function is lost or decreased, indicates that the subject mammal is at risk for the aging related disorder or disease. Molecular biological methods for identifying and comparing sequences are well-known in the alt.

The invention is also directed to a method for identifying aging-related disease or disorder caused by or associated with a somatic mutation in a gene encoding p62. In one non-limiting example, the method may comprise:

i. providing the sequence of a p62 gene product;

ii. identifying the sequence of a mutant p62 protein;

iii. preparing a probe to the gene encoding the mutant protein or a fragment thereof; and iv. probing a biological sample from a subject having the above-cited disorder or disease and a biological sample from a patient not having the disease, wherein the presence of the mutant protein in a biological sample from a patient having the disease and the absence of the mutant protein in a biological sample from a mammalian subject not having the disease indicates that the disease or susceptibility to the disease is caused by or associated with the somatic mutation in the gene.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Preparation of p62 Knockout Mice

A. Isolation of a p62 Genomic Clone

The human p62 gene was isolated as shown in U.S. Pat. No. 6,291,645, which is incorporated by reference in its entirety for its disclosure of the cloning and sequencing of the p62 gene. Genomic DNA clones corresponding to p62 locus in mice were cloned from a RPCI 22 mouse BAC library prepared from mouse strain 129/svEvTACCfBr (Invitrogen).

B. Preparation of p62 Knockout Targeting Vector

To produce a null allele of p62, a gene targeting vector was prepared as shown in FIG. 1. p62 genotypic analysis of litters through PCR analysis of litters derived from heterozygote intercross, as well as through Southern blot and immunoblot analysis of extracts from wild or null p62 mice organs show that the targeted gene was disrupted. The targeting vector was constructed by inserting a 2.3 kb EcoRI-BamHI amplified from the 5' end of the p62 genomic clone into EcoRI-BamHI site of pPNT. A 4.0 kb SspI fragment derived form the 3' end of the p62 genomic clone was inserted into the vector at the XhoI site blunt-ended with Klenow enzyme. Potential recombinants were identified by a recombinant fragment assay for gene targeting that is based on PCR. Genomic DNA was prepared from ES cells, tissues of chimeras, and from their offspring. The digested DNA was electrophoresed in an agarose gel, a Southern blot of the gel was prepared and hybridized to a $^{32}$P-labeled probes specific for 5' or 3' flanking region of the p62 gene.

C. Incorporation of Target Vector in ES Cells

The resulting plasmid was linearized with SspI and electroporated into E14TG2a ES cells. Heterozygous ES cell clones were obtained by selection in the presence of G418 and gancyclovir. Genomic DNAs isolated from ES cells and mouse-tails were characterized by Southern blot analysis. The probe was prepared from the 3' region of the p62 genomic sequence. This probe hybridizes to an 11 kb fragment (endogenous p62 gene) and to a 8 kb fragment (disrupted allele). Electroporations were performed on the HPRT-deficient embryonic stem cell line E14TG2a. The cell lines maintained on irradiated mouse embryonic fibroblasts as described previously. Electroporation in the presence of the linearized targeting construct at a concentration of 2-5 nM used 1-sec discharge from a 250-uF capacitor charged to 300 V. Linearization of the both plasmid constructs was achieved with the restriction enzyme Not I. Selection was with G418 and ganciclovir.

D. Production of Homozygous p62−/− Null Mice

Blastocysts were collected from 6 to 7-week-old C57BL6/J mice. Freshly trypsinized embryonic stem (ES) cells, 2-3 days after passage, were resuspended in M2 medium and introduced into blastocysts by microinjection (10-15 cells per blastocyst) at room temperature. Injected blastocysts were returned, without further incubation, to the uteri of pseudopregnant females that had been mated to vasectomized males 2.5 days previously.

Pups derived from blastocysts injected with p62-4 cells were judged for coat color chimerism by inspection. Strain 129/Ola mice, from which the E14TG2a cell line 1 and thence the p62-4 cell line was derived, carry mutations at three loci known to affect coat color: A, c, and p. The 129/Ola mice are homozygous for the dominant allele Aw at the agouti locus, the recessive allele cch at the c locus, and the recessive allele p at the p locus; they are creamy-white colored with pink eyes. Strain C57BL6/J mice were the source of the recipient blastocysts; they are solid black in color with black eyes. Chimeras between these two strains are identified by the presence of lighter patches of fur on a black background. The color of the patches varies depending on which layers of epidermis are ES cell-derived and which are recipient blastocyst-derived. Agouti patches show the indirect inhibitory effects of the dominant Aw gene in ES cell-derived mesodermal cells on the production of black pigment by melanocytes. Sight yellow patches show the direct effects of the Cch and p genes on the production and packaging of the pigments themselves. Agouti and/or yellow patches can be seen in a given chimeric animal. Animals strongly chimeric for coat color can be almost uniformly yellowish brown or cream colored with black eyes. The proportion of resulting chimeras was 28% of surviving pups. Pups were scored for coat color chimerism and mated when mature to test for germ-line transmission of coat color markers from p62-4 to progeny.

E. Homozygous p62−/− Mouse Phenotype (i) Obesity

Figure 3:
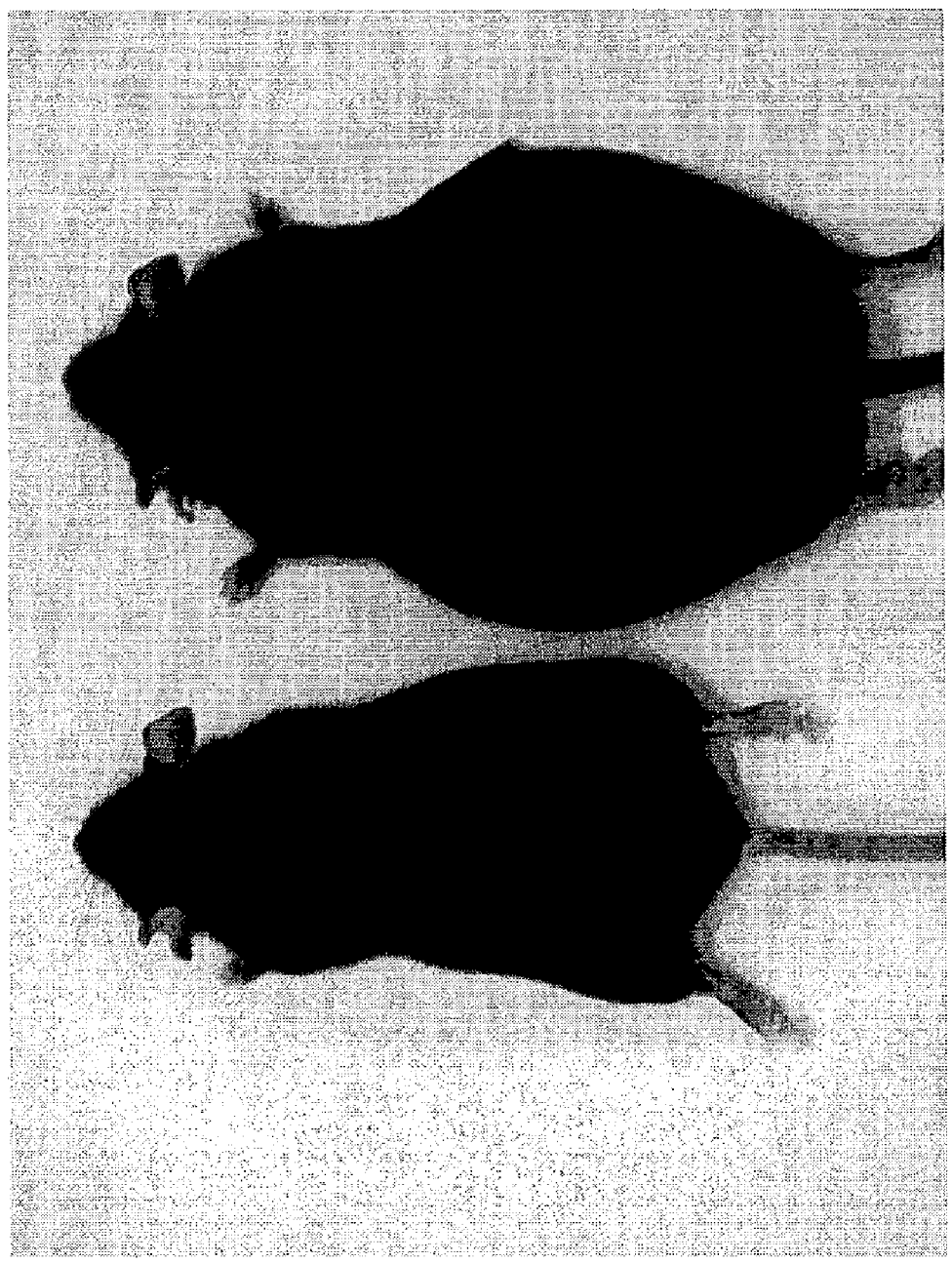
FIG. 3 shows photographs of representative wild-type and p62-null mice.
Figure 4:
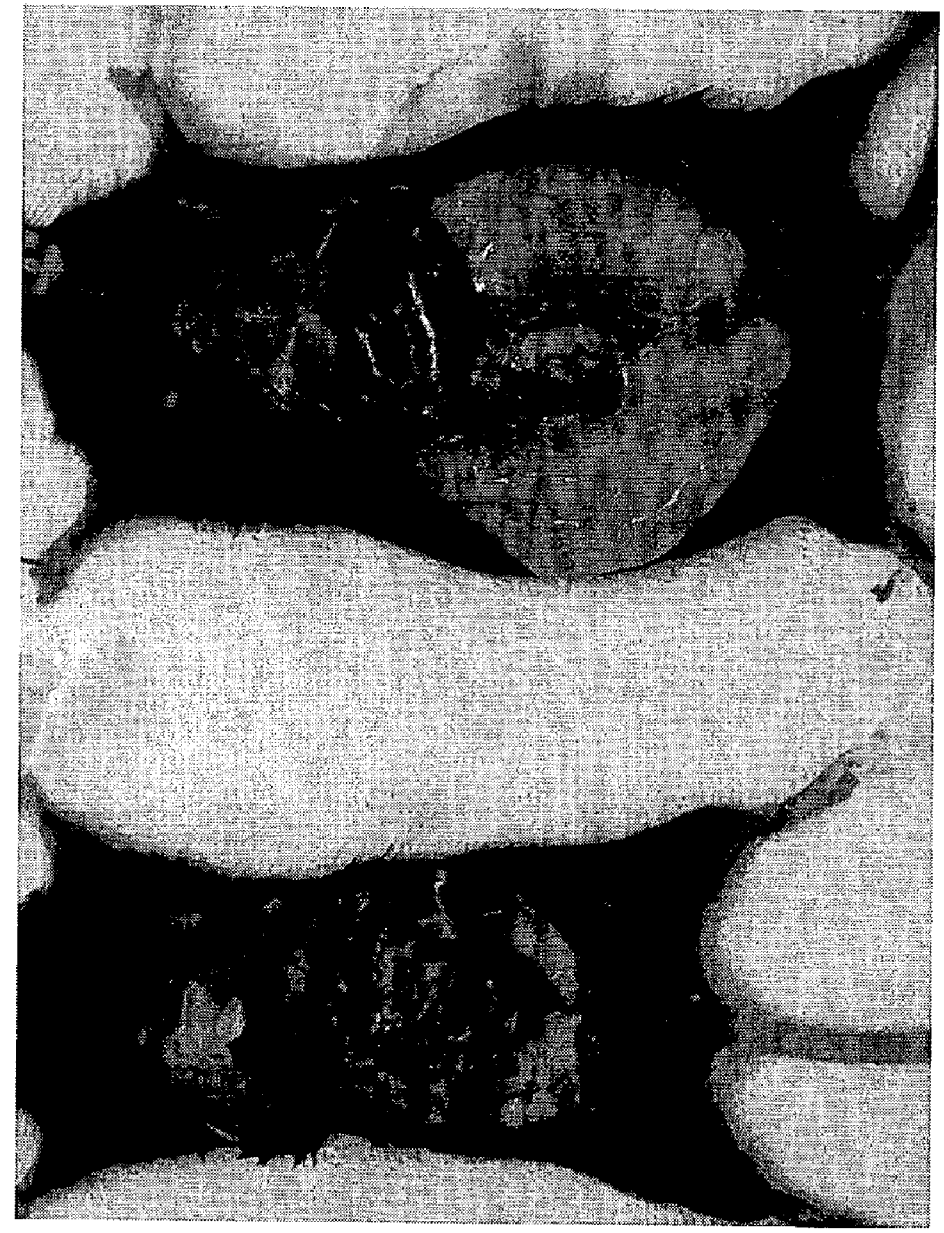
FIG. 4 shows fat deposition in wild-type and p62-null mice.

FIG. 3 shows photographs of representative wild-type and p62-null mice. p62-null mice are obese. FIG. 4 shows the amount of fat deposition in wild-type and p62-null mice.

Figure 5:
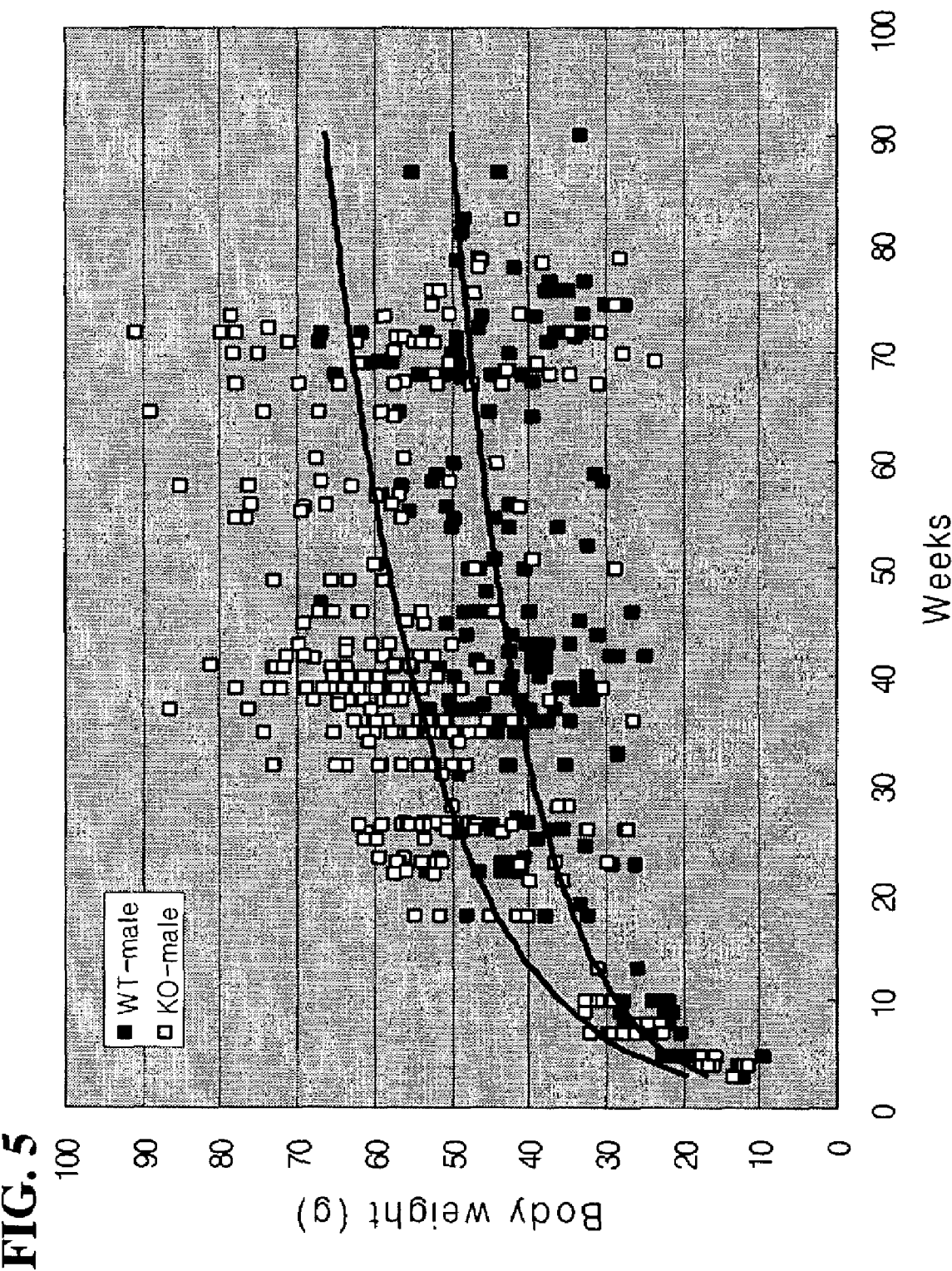
FIG. 5 shows population study—body weight of wild-type (filled square) and p62-null (open square) male mice at various ages.
Figure 6:
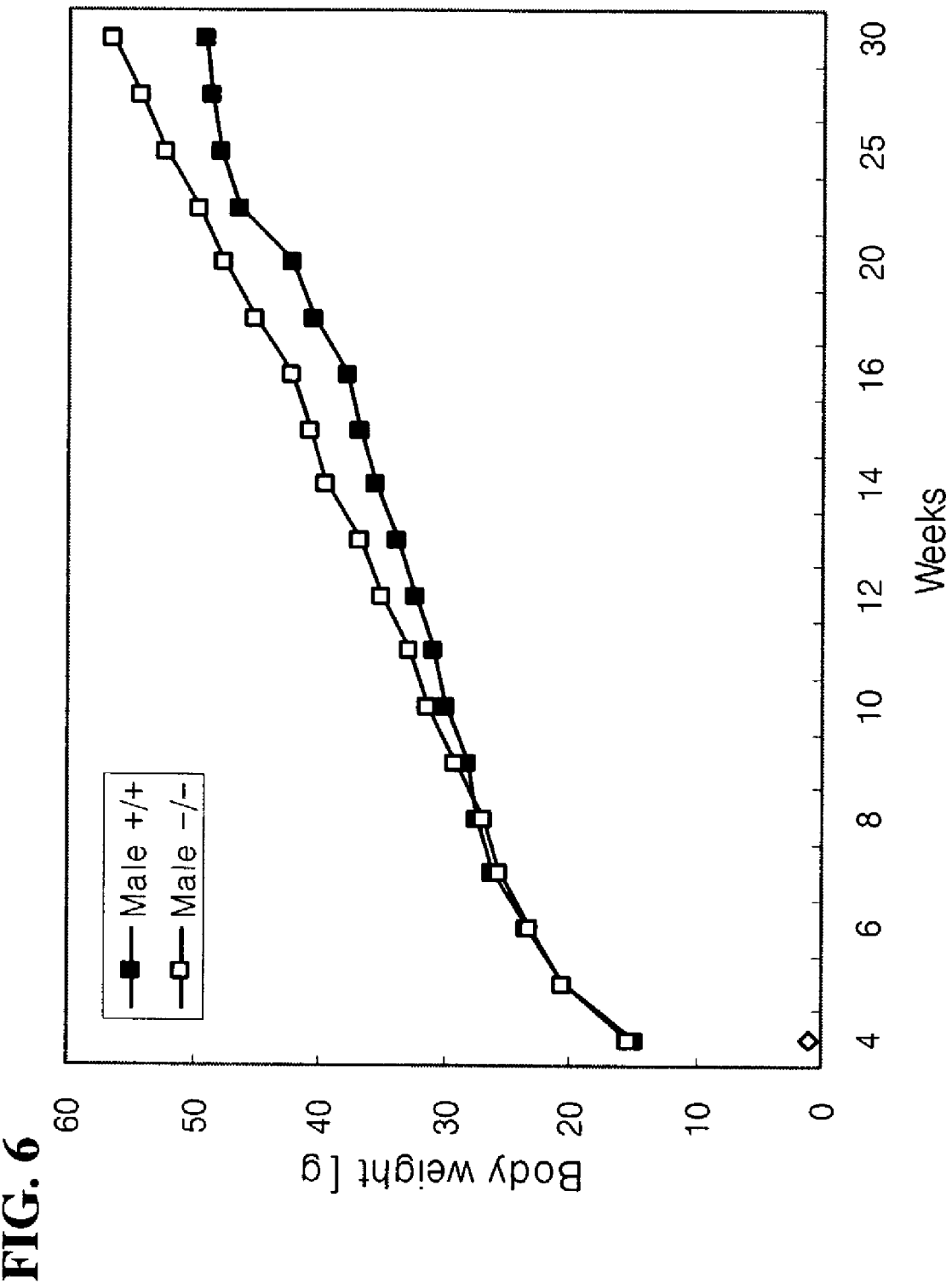
FIG. 6 shows cohort study—growth curves of wild-type and p62-null male mice from weaning (4 weeks) until 30 weeks of age.

FIG. 5 shows population study in terms of the body weight of wild-type (filled square) and p62-null (open square) male mice at various ages. This again indicates that p62-null mice are generally more obese than wild-type mice. In another aspect, FIG. 6 shows a cohort study in which growth of wild-type and p62-null male mice from weaning (4 weeks) until 30 weeks of age are measured. A curve is generated indicating the p62-null mice grow to greater body weight over a span of 30 weeks from birth.

Figure 7:
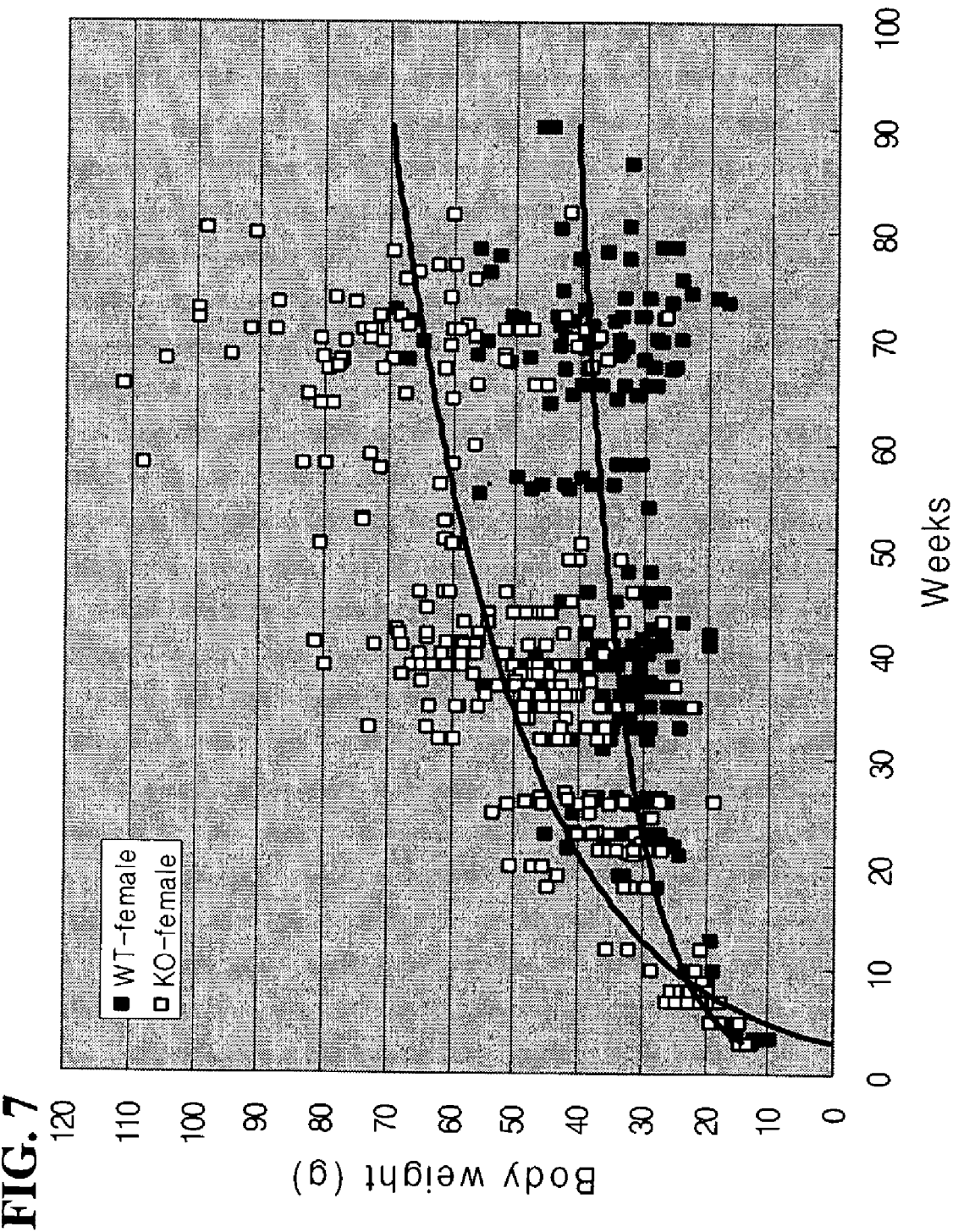
FIG. 7 shows population study—body weight of wild-type (filled square) and p62-null (open square) female mice at various ages.
Figure 8:
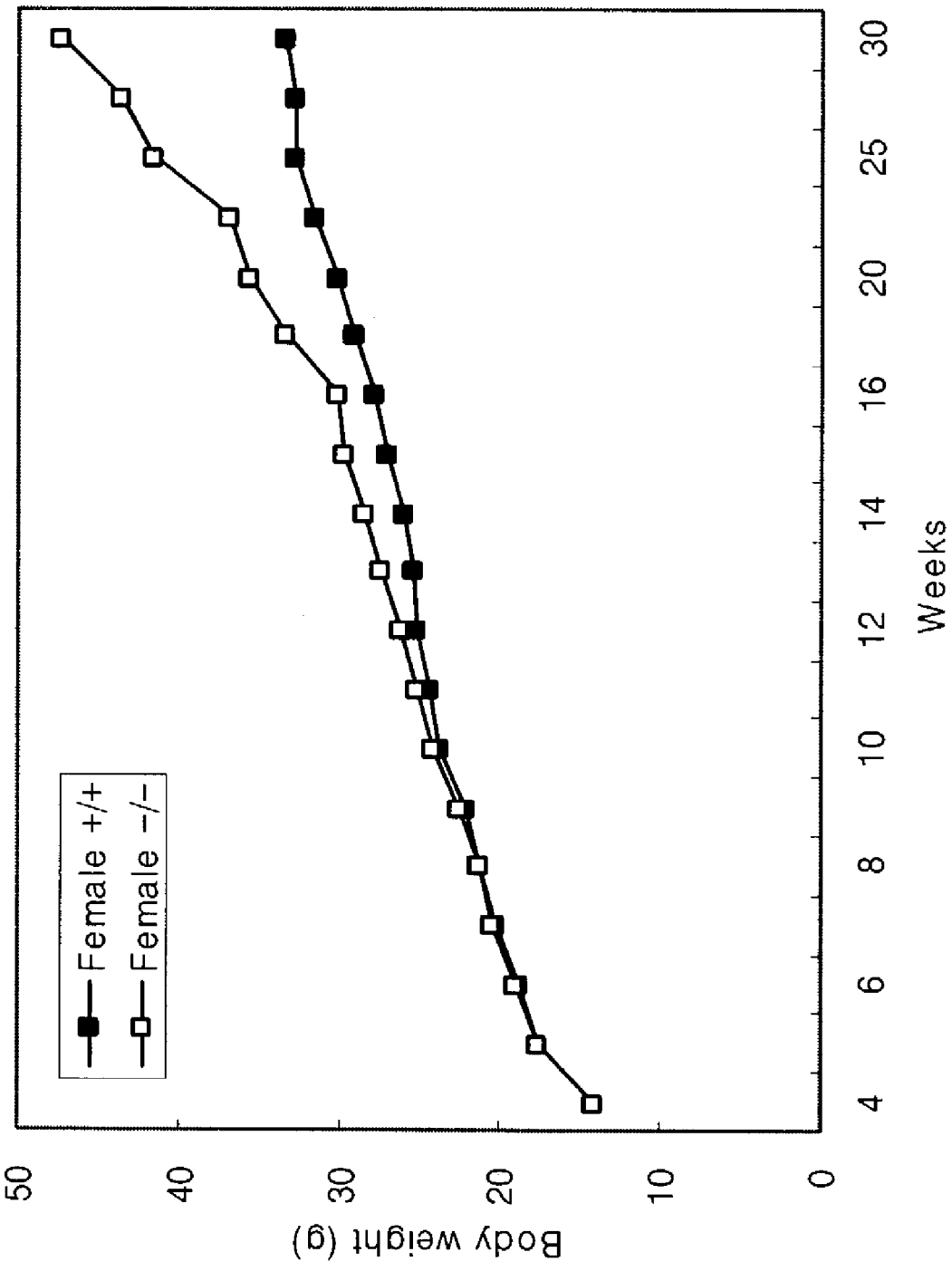
FIG. 8 shows cohort study—growth curves of wild-type and p62-null female mice from weaning (4 weeks) until 30 weeks of age.
Figure 9:
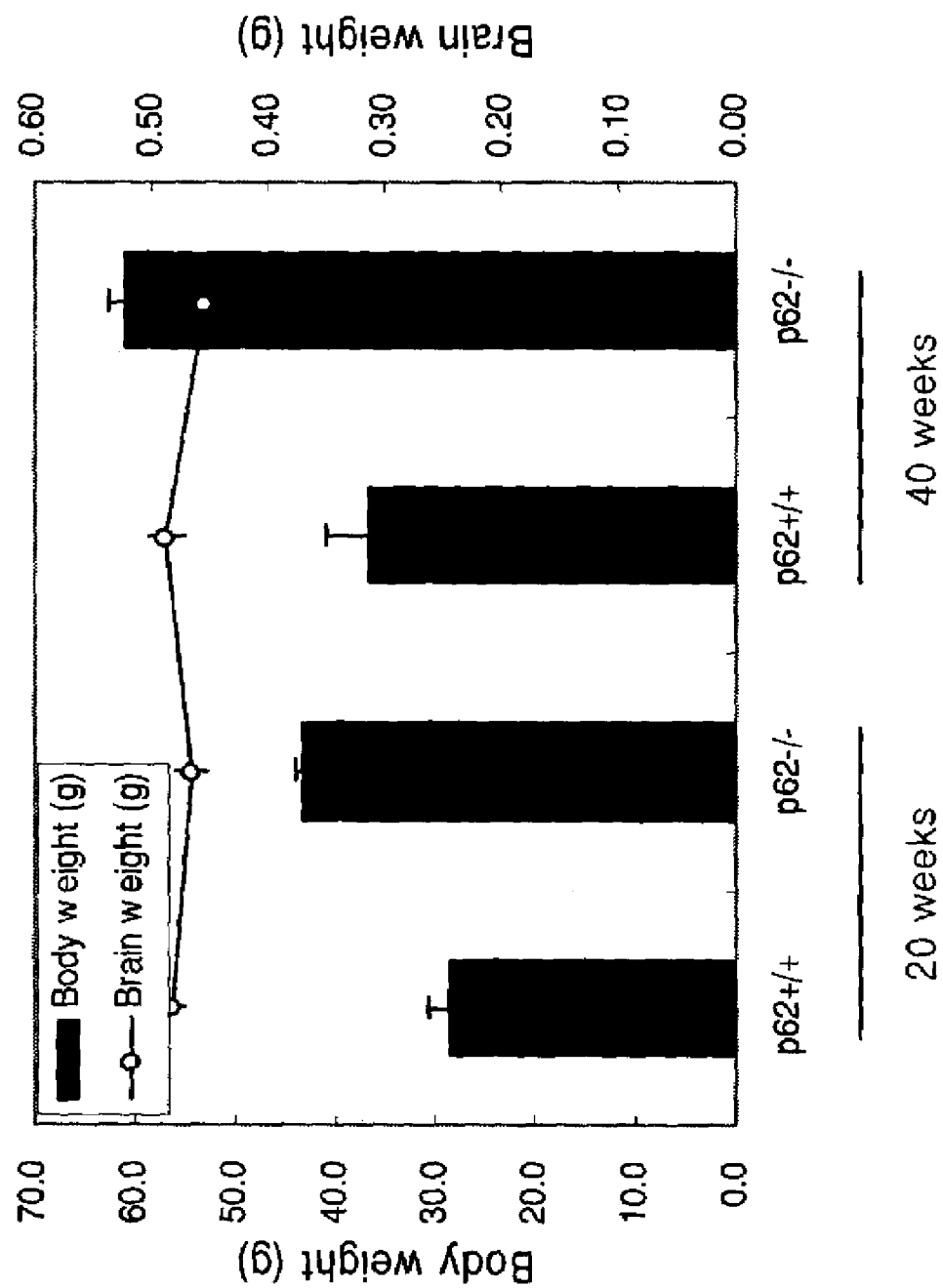
FIG. 9 shows body weight gain in 20-week and 40-week old wild-type and p62-null female mice. Brain-to-Body weight ratio is same in wild-type and p62-null mice.

Female mice were also studied for body weight and growth. FIG. 7 shows a population study in term of the body weight of wild-type (filled square) and p62-null (open square) female mice at various ages. This indicates that female p62-null mice are also generally more obese than wild-type female mice. FIG. 8 shows cohort study in which growth of wild-type and p62-null female mice from weaning (4 weeks) until 30 weeks of age are measured. In addition, FIG. 9 shows body weight gain in 20-week and 40-week old wild-type and p62-null female mice. Brain-to-Body weight ratio is same in wild-type and p62-null mice.

Figure 11:
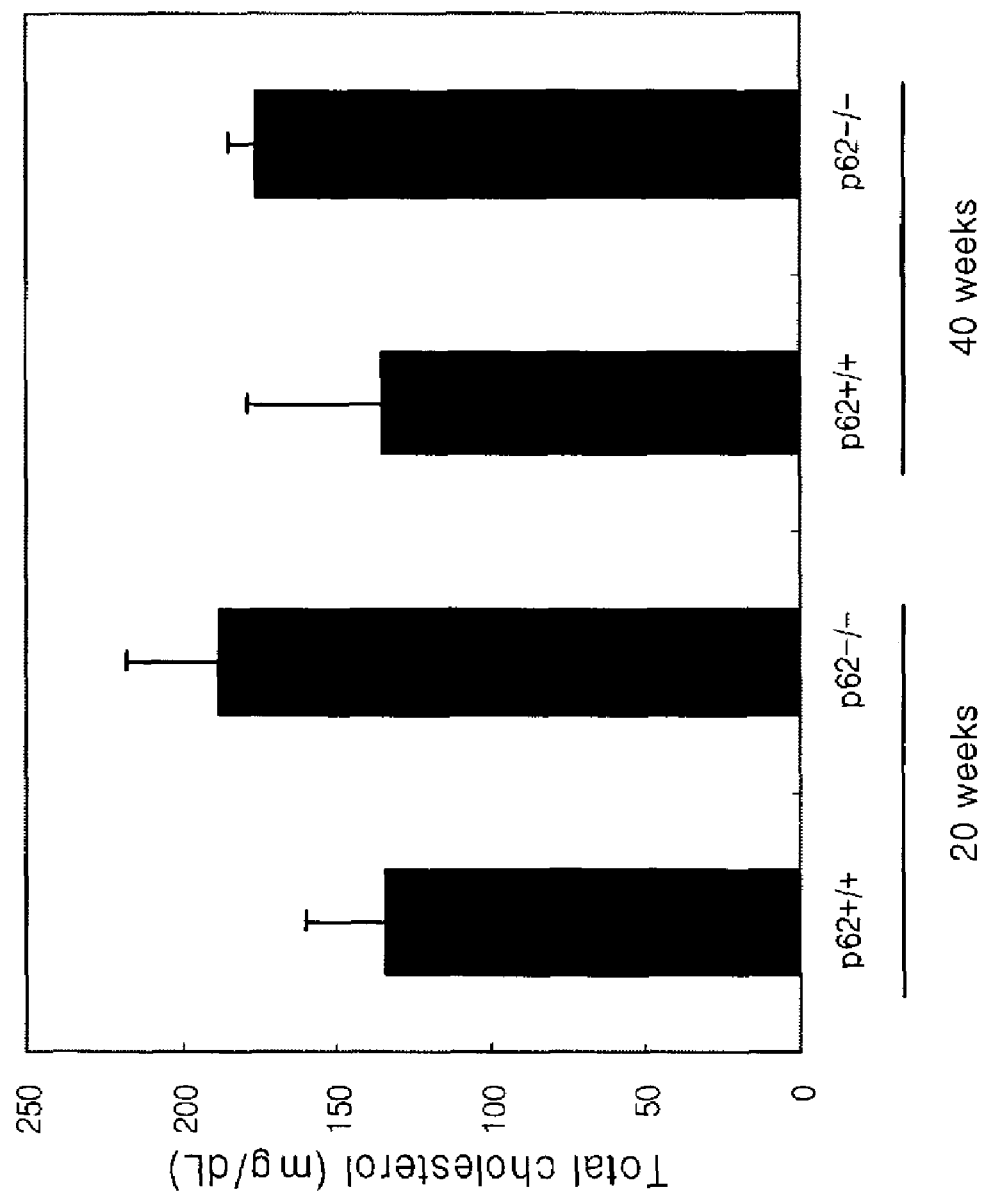
FIG. 11 shows blood total cholesterol levels after 12 h fasting in 20-week and 40-week old wild-type and p62-null female mice. Blood total cholesterol level is 134±23 mg/dl and 187±33 mg/dl in 20-week old wild-type and p62-null mice, respectively. In 40-week old wild type and p62-null mice blood total cholesterol level is 135±31 mg/dl and 175±11 mg/dl respectively.

The level of total cholesterol in the blood was also measured. FIG. 11 shows blood total cholesterol levels after 12 h fasting in 20-week and 40-week old wild-type and p62-null female mice. Blood total cholesterol level is 134±23 mg/dl and 187±33 mg/dl in 20-week old wild-type and p62-null mice, respectively. In 40-week old wild type and p62-null mice blood total cholesterol level is 135±31 mg/dl and 175±11 mg/dl respectively.

Figure 12:
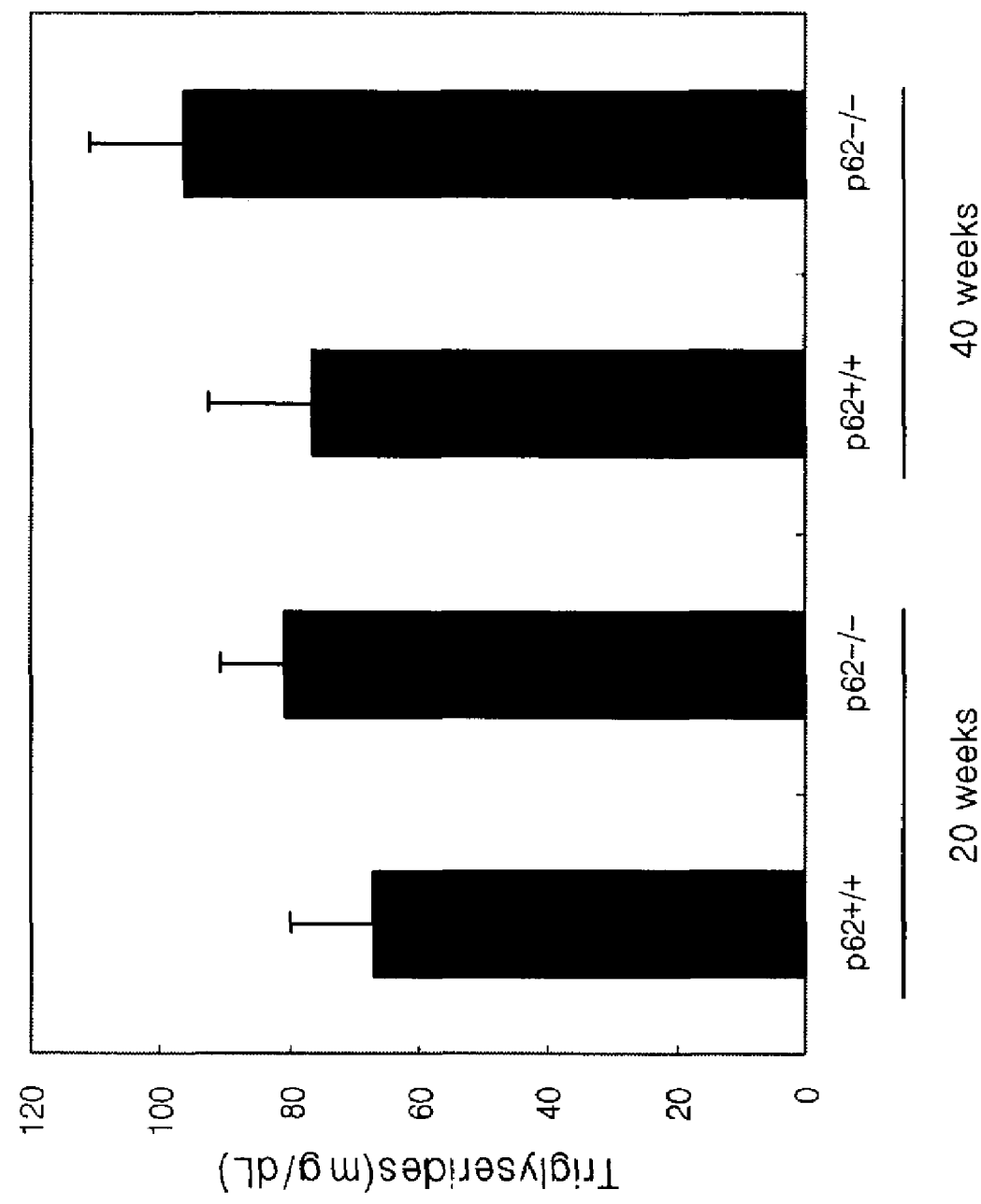
FIG. 12 shows blood triglyceride levels after 12 h fasting in 20-week and 40-week old wild-type and p62-null female mice. Blood triglyceride level is 67±13 mg/dl and 81±10 mg/dl in 20-week old wild-type and p62-null mice, respectively. In 40-week old wild-type and p62-null mice, blood triglyceride level is 76±17 mg/dl and 96±16 mg/dl, respectively.

The level of triglyceride in the blood was measured. FIG. 12 shows blood triglyceride levels after 12 h fasting in 20-week and 40-week old wild-type and p62-null female mice. Blood triglyceride level is 67±13 mg/dl and 81±10 mg/dl in 20-week old wild-type and p62-null mice, respectively. In 40-week old wild-type and p62-null mice, blood triglyceride level is 76±17 mg/dl and 96±16 mg/dl, respectively.

Figure 13:
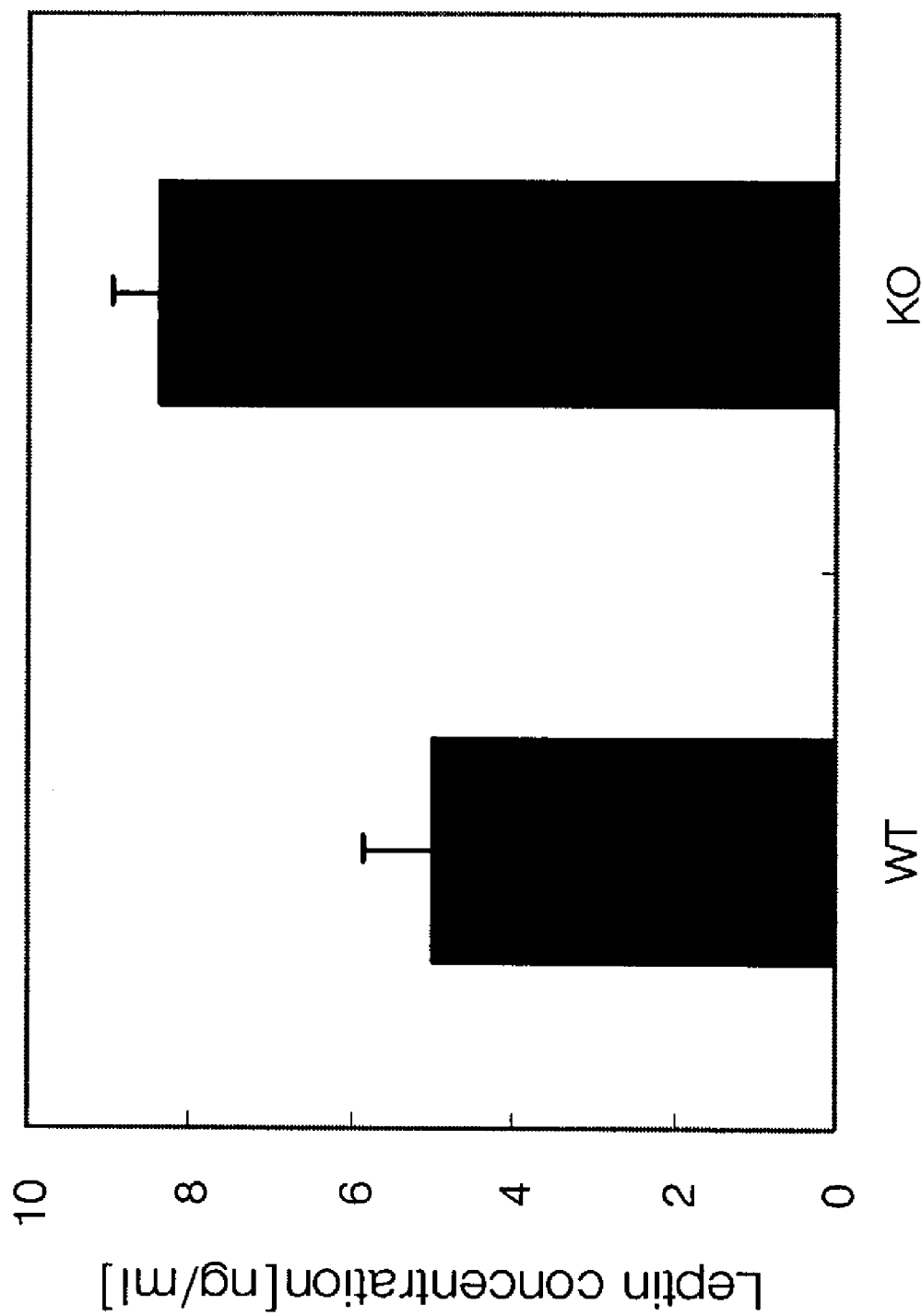
FIG. 13 shows serum leptin levels after 12 h fasting in wild-type and p62-null female mice. Serum leptin level is 5.00±0.84 ng/ml in wild-type mice and 8.37±0.84 ng/ml in p62-null mice.

Finally, serum leptin levels were measured. FIG. 13 shows serum leptin levels after 12 h fasting in wild-type and p62-null female mice. Serum leptin level is 5.00±0.84 ng/ml in wild-type mice and 8.37±0.84 ng/ml in p62-null mice. Thus, the p62-null mice show the indications of obesity.

All p62−/− pups showed a similar appearance. At birth, p$^{62}$−/− mice appeared to be indistinguishable from their littermates. A difference in size and appearance of p62−/− mice was seen during the first few weeks of life.

(ii) Diabetes

Figure 10:
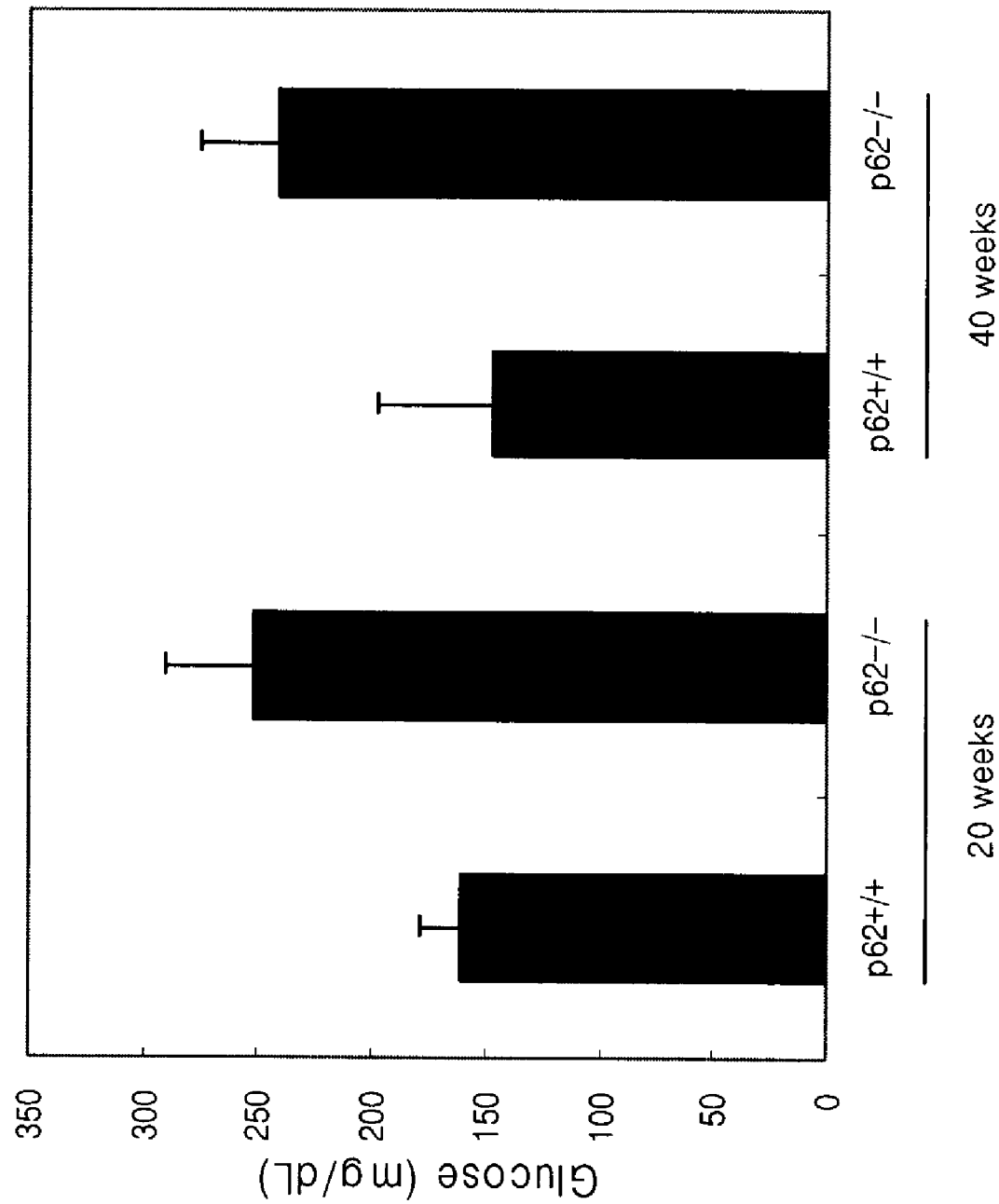
FIG. 10 shows blood glucose levels after 12 h fasting in 20-week and 40-week old wild-type and p62-null female mice. Blood glucose level is 160±19 mg/dl and 240±30 mg/dl in 20-week old wild-type and p62-null mice, respectively. In 40-week old wild-type and p62-null mice blood glucose level is 147±49 mg/dl and 241±33 mg/dl, respectively.

The level of glucose in the blood was measured. FIG. 10 shows blood glucose levels after 12 h fasting in 20-week and 40-week old wild-type and p62-null female mice. Blood glucose level is 160±19 mg/dl and 240±30 mg/dl in 20-week old wild-type and p62-null mice, respectively. In 40-week old wild-type and p62-null mice blood glucose level is 147±49 mg/dl and 241±33 mg/dl, respectively.

Figure 14:
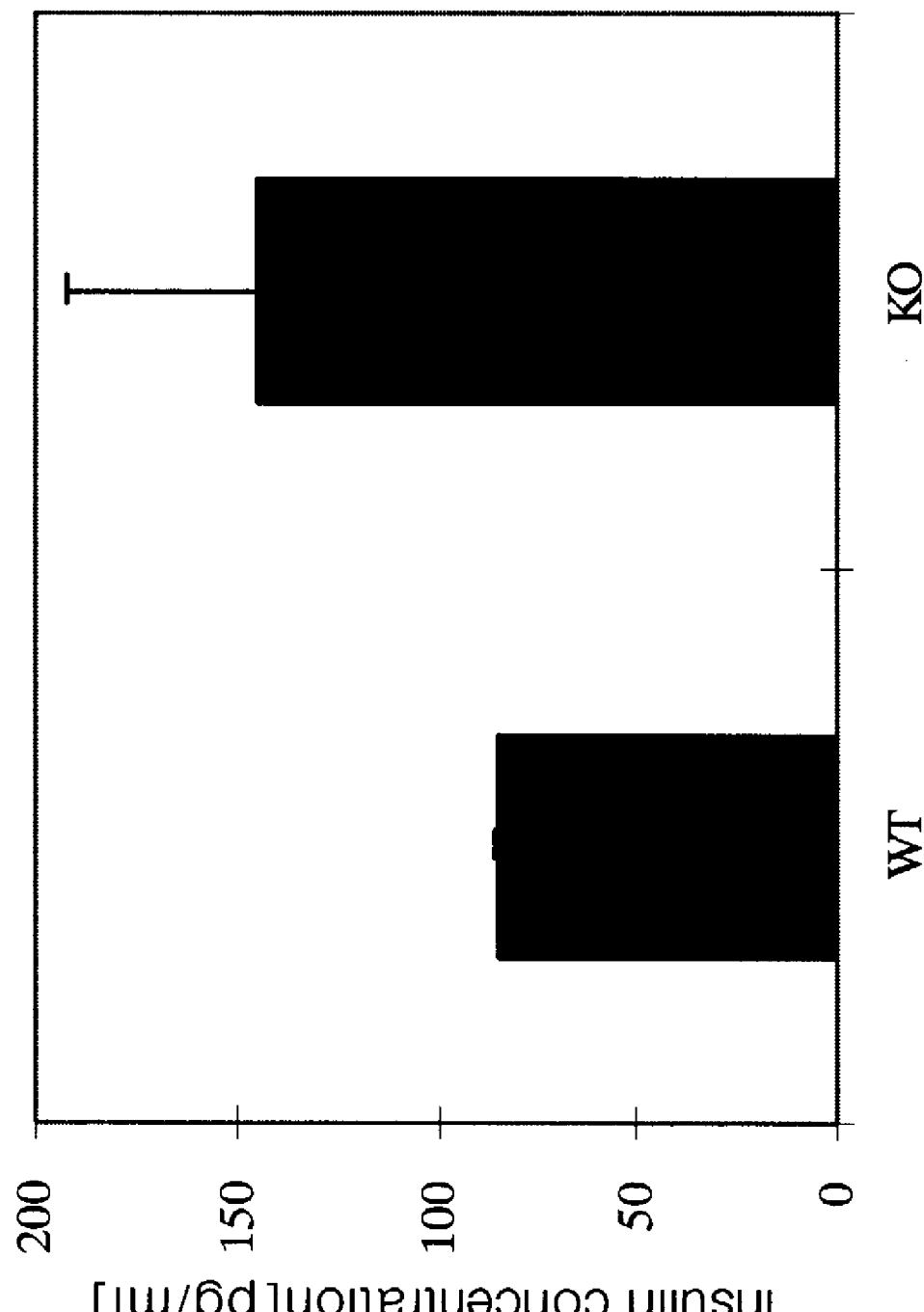
FIG. 14 shows serum insulin levels after 12 h fasting in wild-type and p62-null female mice. Serum insulin level is 84.60±0.70 pg/ml in wild-type mice and 144.30±47.30 ng/ml in p62-null mice.
Figure 15:
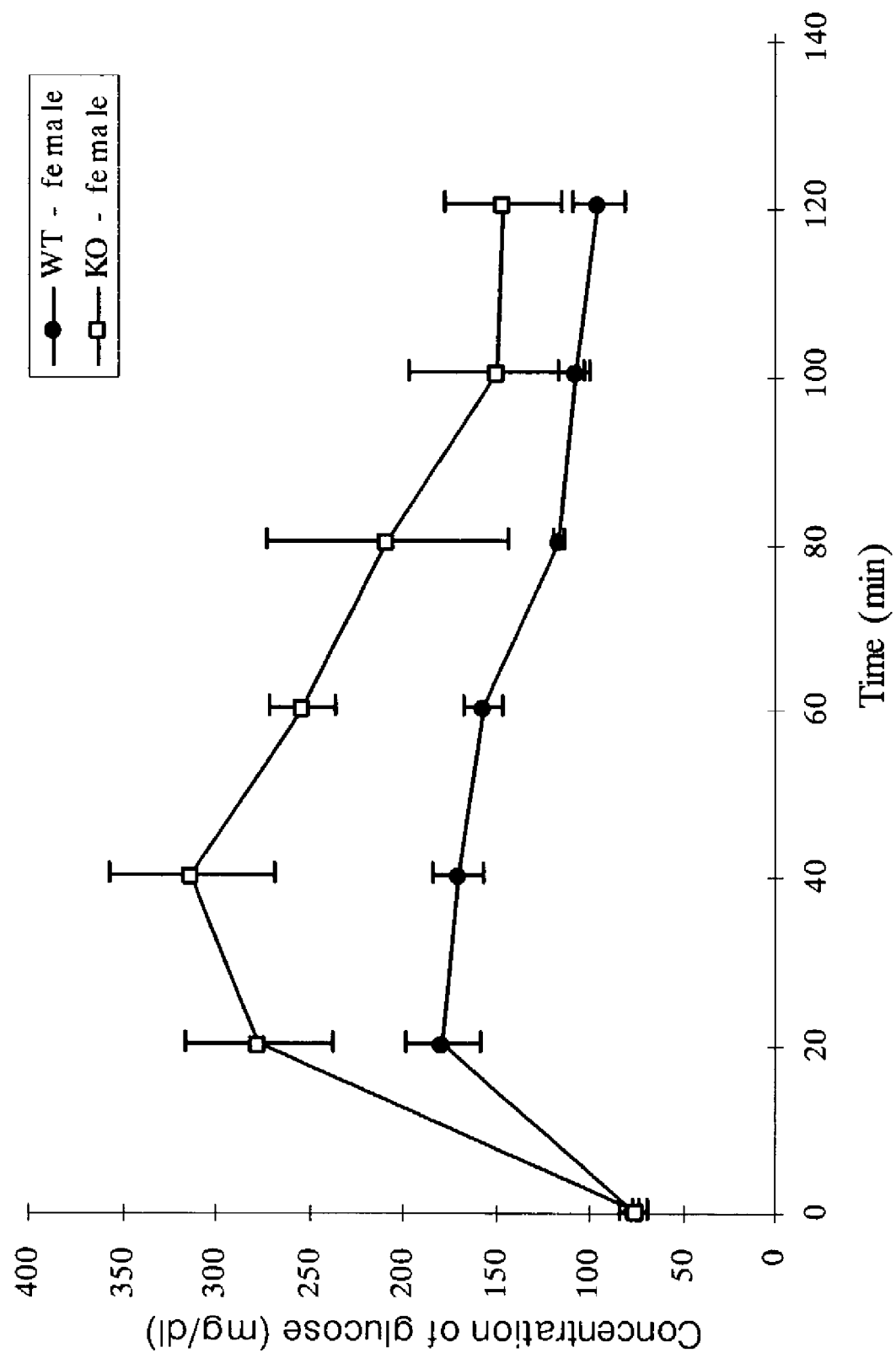
FIG. 15 shows glucose levels during glucose tolerance test in 28-week old wild-type and p62-null female mice.
Figure 16:
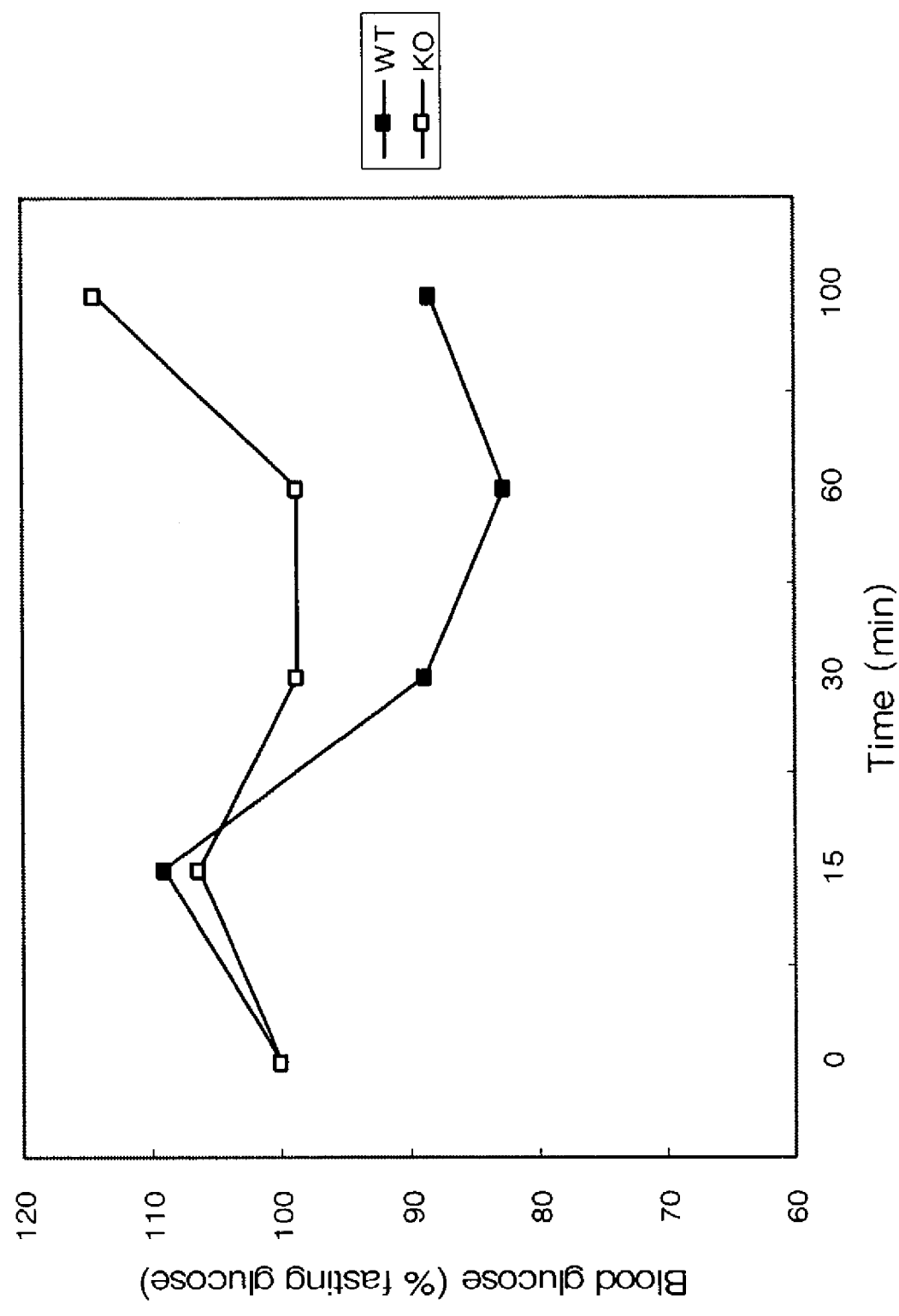
FIG. 16 shows glucose levels during insulin tolerance test in 20-week old wild-type and p62-null male mice.

The mice were measured for signs of diabetes. FIG. 14 shows serum insulin levels after 12 h fasting in wild-type and p62-null female mice. Serum insulin level is 84.60±0.70 pg/ml in wild-type mice and 144.30±47.30 ng/ml in p62-null mice, which is significantly more in p62-null female. Further, FIG. 15 shows glucose levels during glucose tolerance test in 28-week old wild-type and p62-null female mice, and show that the knock-out female mice exhibit greater concentration of glucose in the blood after two hours, indicating that glucose is not easily processed in the p62-null mice. FIG. 16 shows glucose levels rising in an insulin tolerance test in 20-week old p62-null male mice, compared with wild-type mice.

Figure 17:
FIGS. 17A-17B show pancreatic islet size and morphology in (A) 20-week old wild-type and (B) p62-null female mice.
Figure 17:
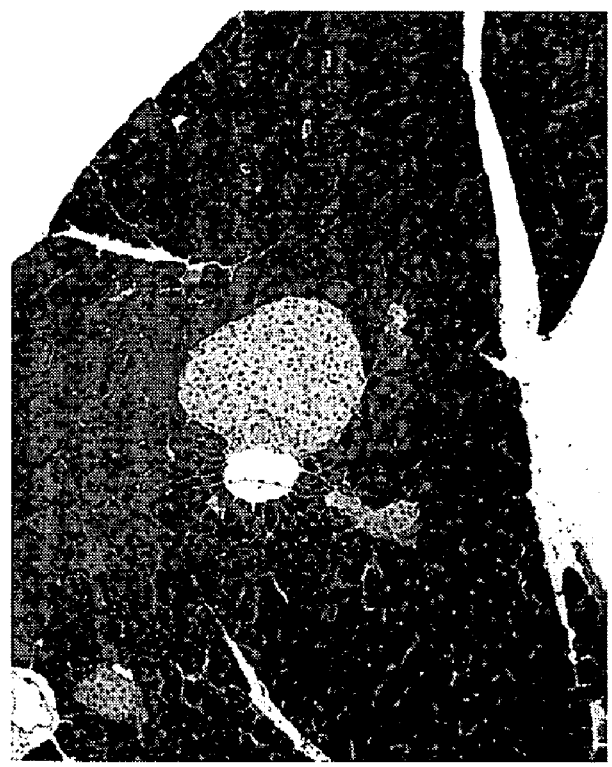
Figure 18:
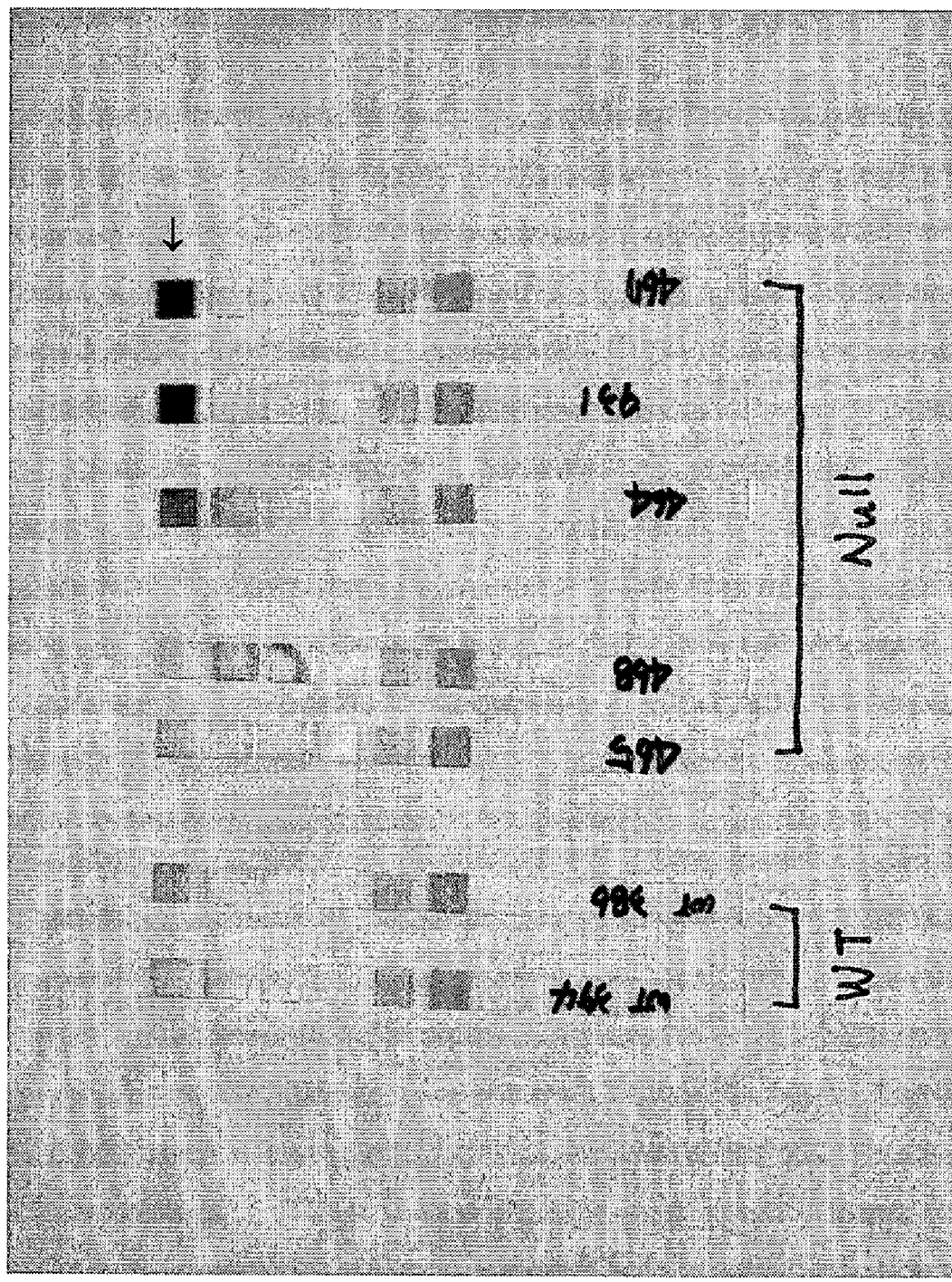
FIG. 18 shows urine glucose test in wild-type and p62-null mice. Glucose test patch is indicated by arrow and changed to green color in p62-null mice.

An examination of the pancreatic islet size and morphology in 20-week old wild-type and p62-null female mice indicates that the p62-null female mice have larger size pancreatic islet. FIGS. 17A-17B show pictures of the pancreatic islets. Further, FIG. 18 shows urine glucose test in wild-type and p62-null mice. Glucose test patch is indicated by arrow and changed to green color in p62-null mice. p62-null mice exhibited greater amount of glucose that is expelled in the urine. All of these phenotypes are typical in development of human or mouse type-2 diabetes.

Figure 19:
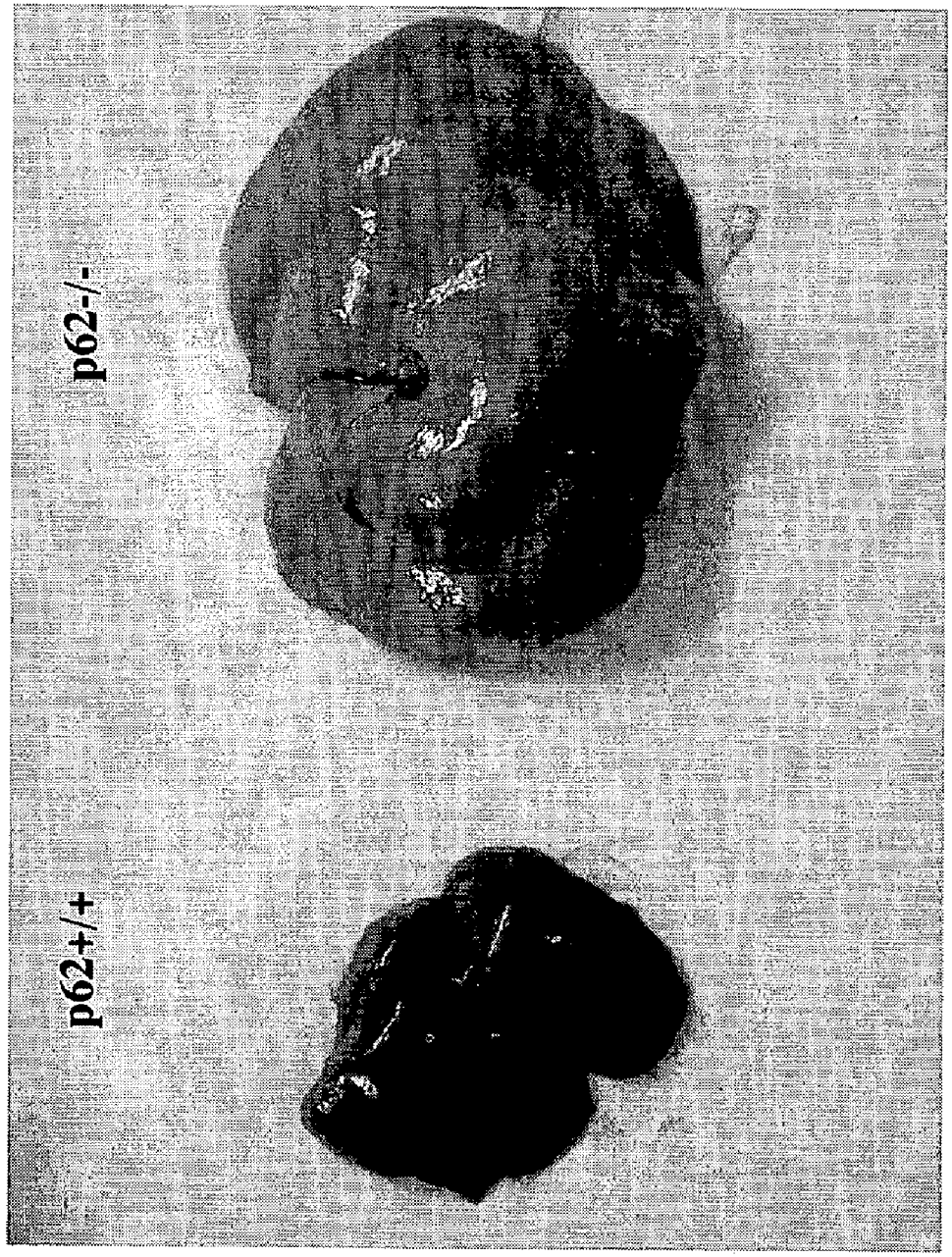
FIG. 19 shows hepatomegaly and steatosis in p62-null mice.
Figure 20:
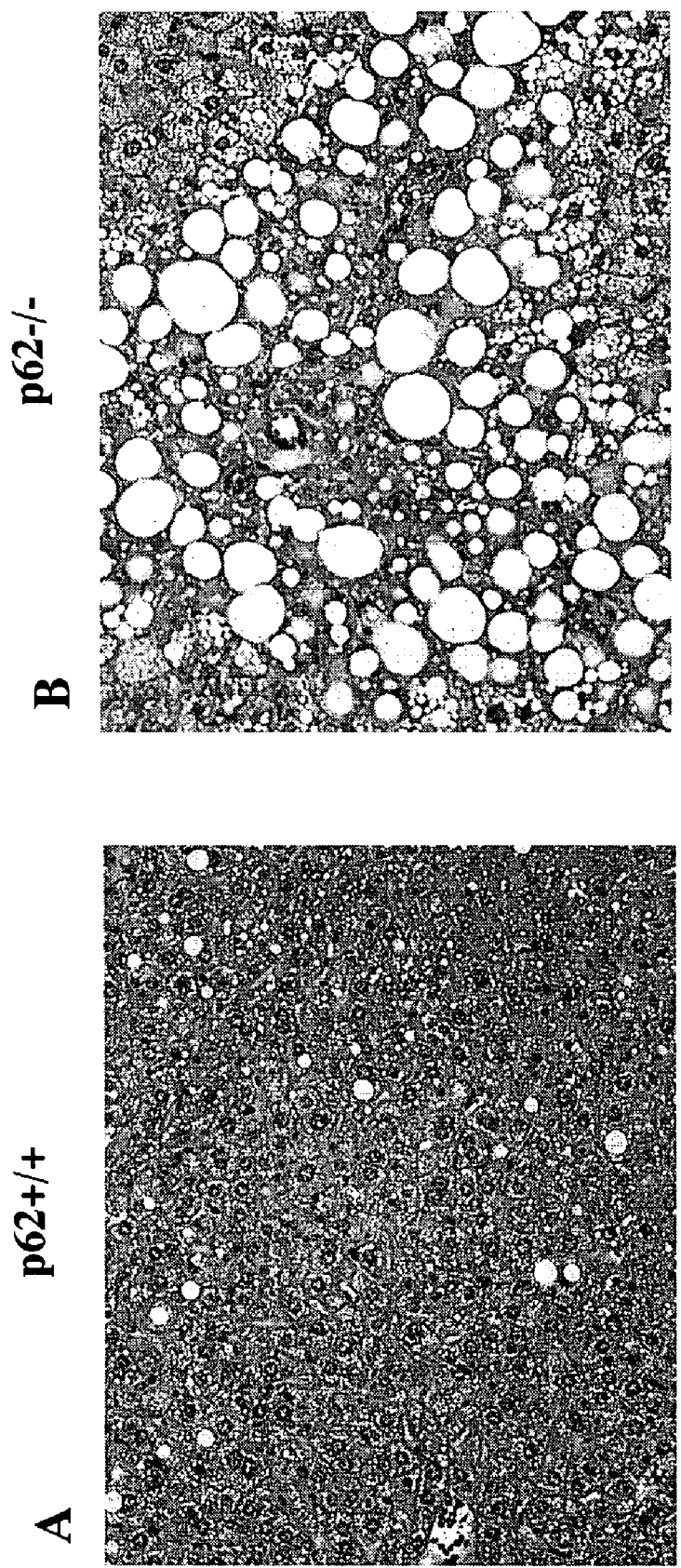
FIGS. 20A-20B show steatosis in p62-null mice. Liver samples were obtained from (A) wild-type and (B) p62-null mice. Tissue sections were stained with H&E.
Figure 21:
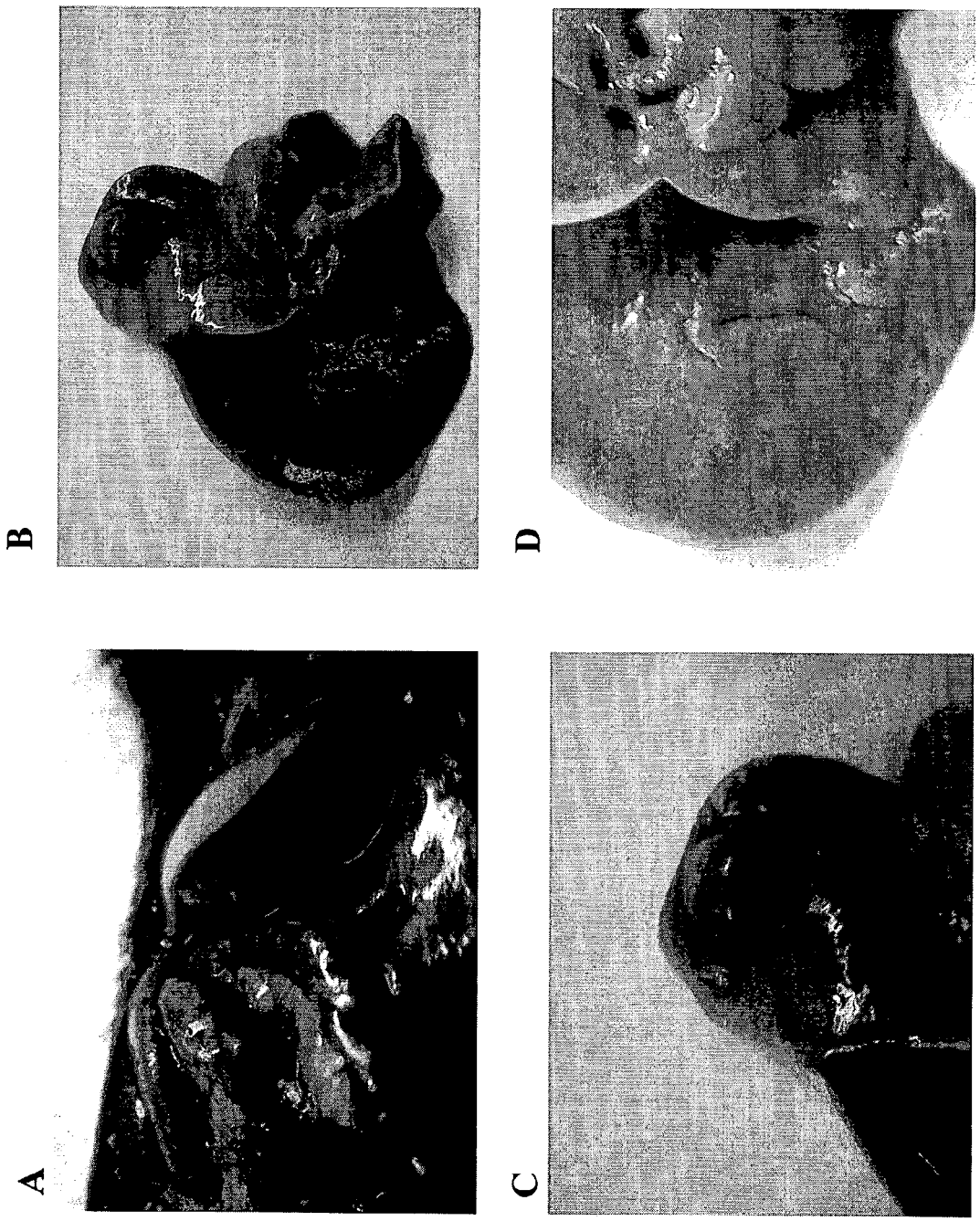
FIGS. 21A-21D show hepatocellular carcinoma in 67-week old p62-null male mice.

(iii) Fatty Liver p62-null mice exhibit fatty liver phenotype. FIG. 19 shows hepatomegaly and steatosis in p62-null mice. Further, FIGS. 20A-20B show steatosis in p62-null mice. Tissue sections were stained with H&E.

(iv) Liver Cancer

Figure 22:
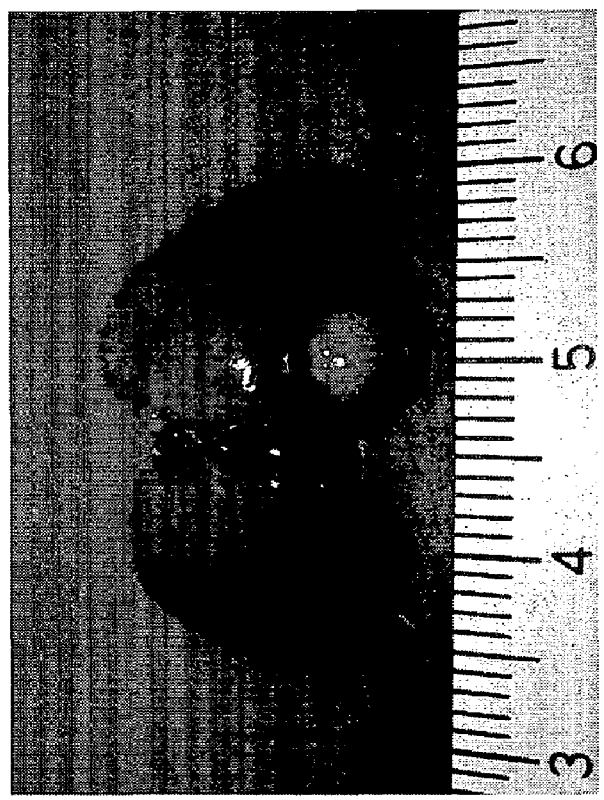
FIGS. 22A-22B show hepatocellular carcinoma in 36-week old p62-null male mice.
Figure 22:
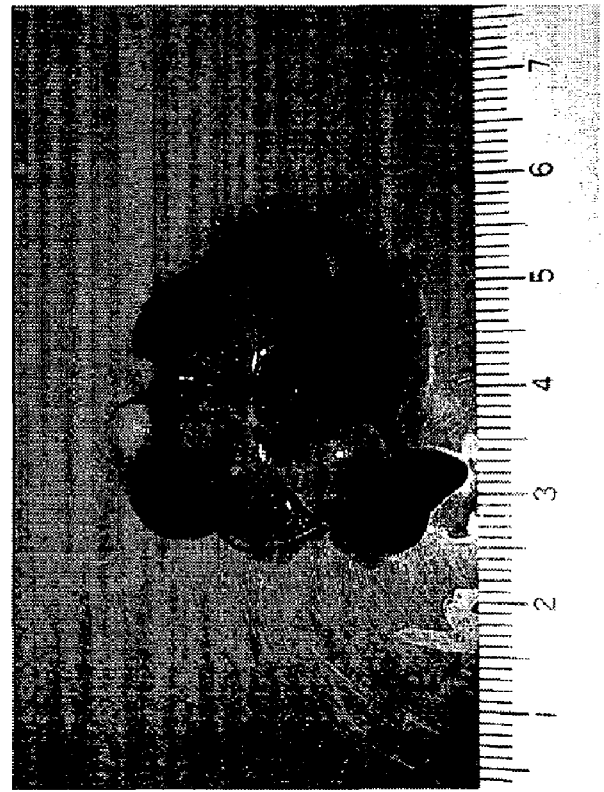
Figure 23:
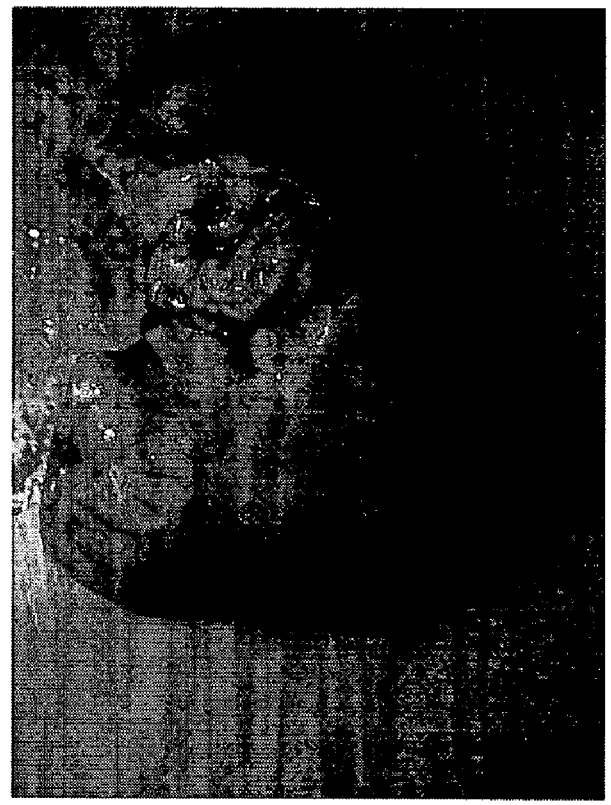
FIGS. 23A-23B show hepatocellular carcinoma in 59-week old p62-null male mice.
Figure 23:

In addition to the above, an examination of the mice indicates that p62-null mice suffer from liver cancer. FIGS. 21A-21D show hepatocellular carcinoma in 67-week old p62-null male mice. FIGS. 22A-22B show hepatocellular carcinoma in 36-week old p62-null male mice. And FIGS. 23A-23B show hepatocellular carcinoma in 59-week old p62-null male mice.

(v) Early Male Mortality

Figure 24:
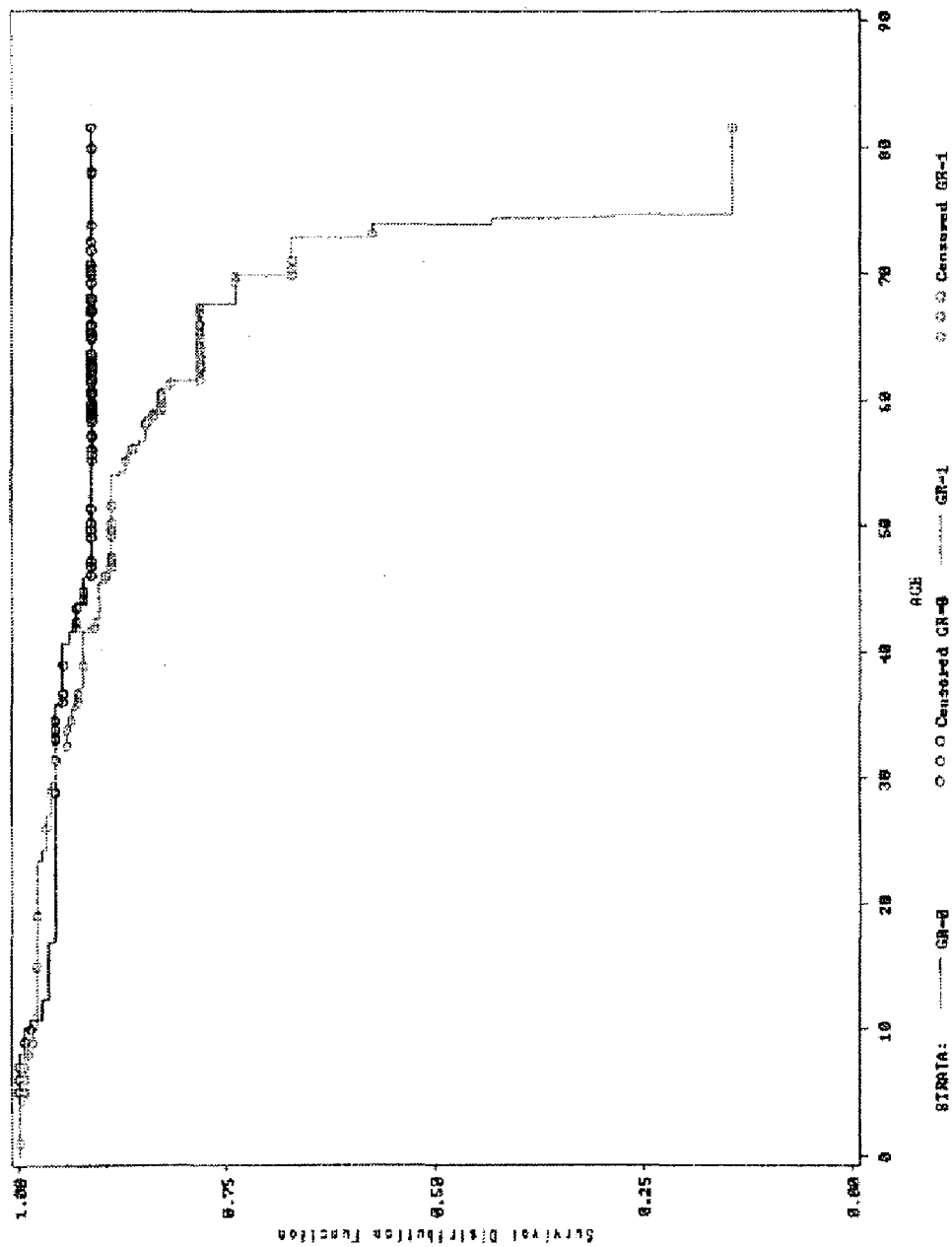
FIG. 24 shows Kaplan-Meier survival curves for male mice in wild-type group (black) and in p62 knockout group (red).
Figure 25:
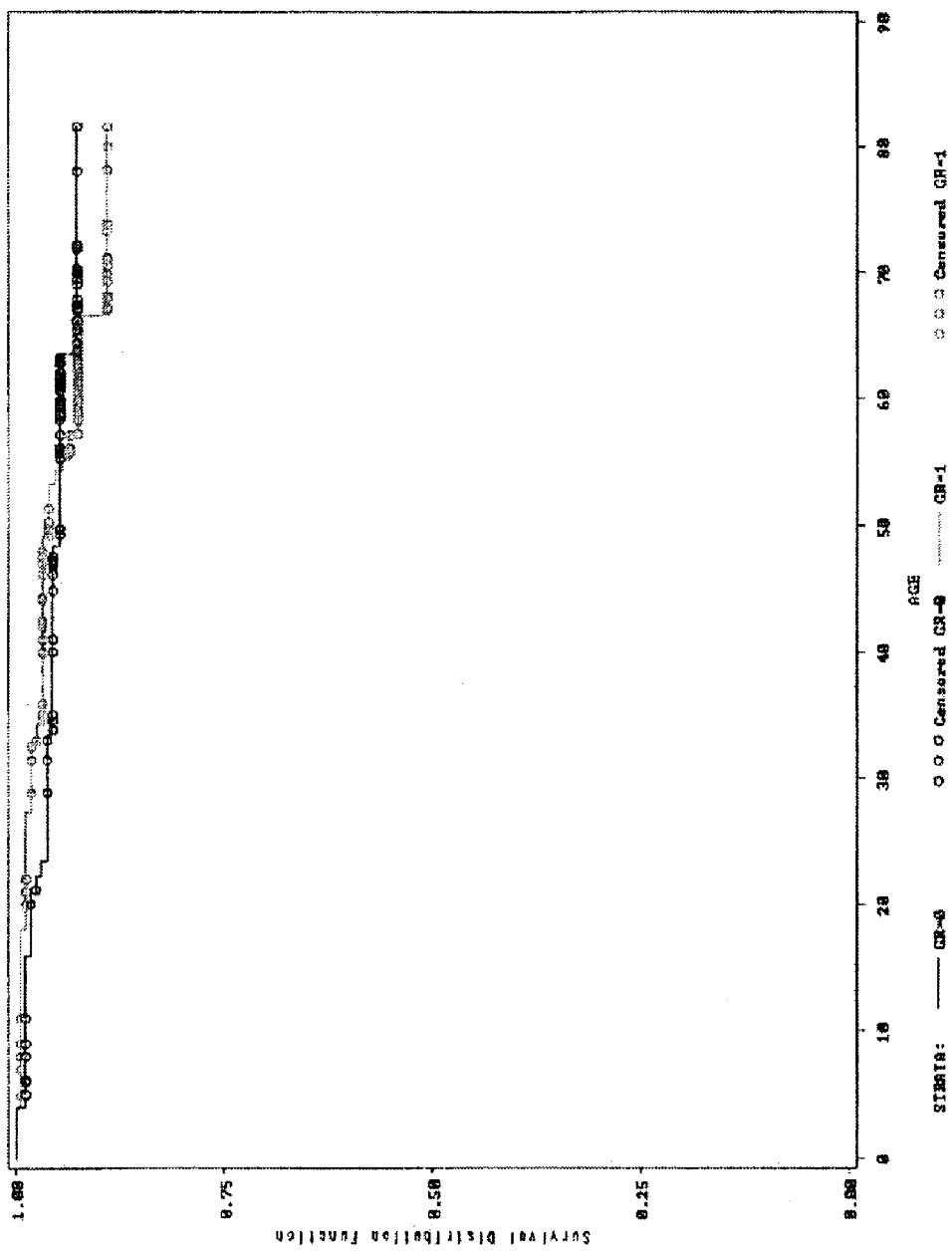
FIG. 25 shows Kaplan-Meier survival curves for female mice in wild-type group (black) and in p62 knockout group (red).

An interesting phenotype associated with p62-null mice is that they exhibit early male mortality. FIG. 24 shows Kaplan-Meier survival curves for male mice in wild-type group (black) and in p62 knockout group (red). Male p62-null mice have a much shorter life span than male wild-type mice. FIG. 25 shows Kaplan-Meier survival curves for female mice in wild-type group (black) and in p62 knockout group (red). The curves show that p62-null female mice life span are about the same.

(vi) Formation of Intracellular Inclusion

Figure 26:
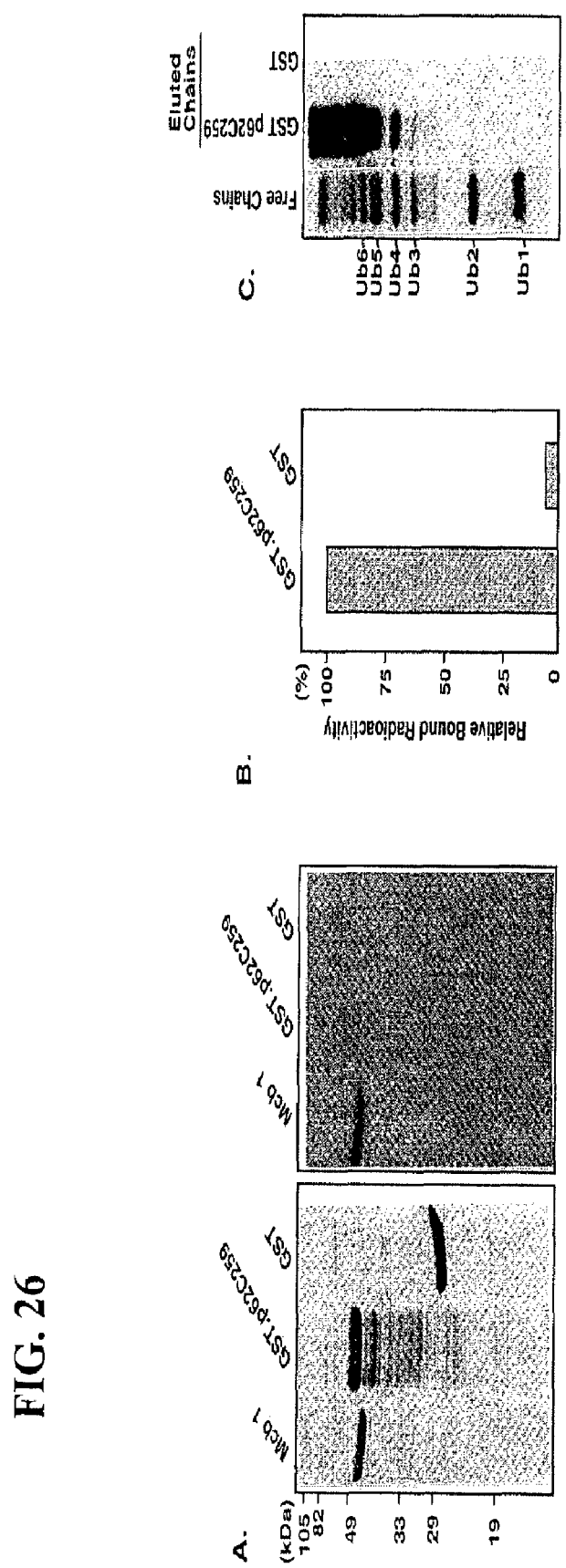
FIGS. 26A-26C show multiubiquitin chain binding to p62 and Mcb1. (A) Purified recombinant arabidopsis Mcb1 (Mcb1), GST fused p62 ubiquitin binding region (GST. P62C259), and GST were subjected to SDS-PAGE and transferred to nitrocellulose. The membrane was either stained with Ponceau S (left panel) or incubated with $^{125}$I-labeled multiubiquitin chains, washed, and subjected to autoradiography (right panel). (B) GST or GST.p62C259 was incubated with $^{125}$I-labeled multiubiquitin chains in solution, the bound chains were precipitated using glutathione coupled agarose beads, and the amount of bound chains measured by γ-counting. (C) $^{125}$I-labeled multiubiquitin chains precipitated in (B) were eluted from the beads by heating in SDS-containing buffer; the eluent was separated by SDS PAGE and the profile of multiubiquitin chains analyzed by autoradiography. The mixtures of $^{125}$I-labeled multiubiquitin chains are included for comparison (free chains)
Figure 27:
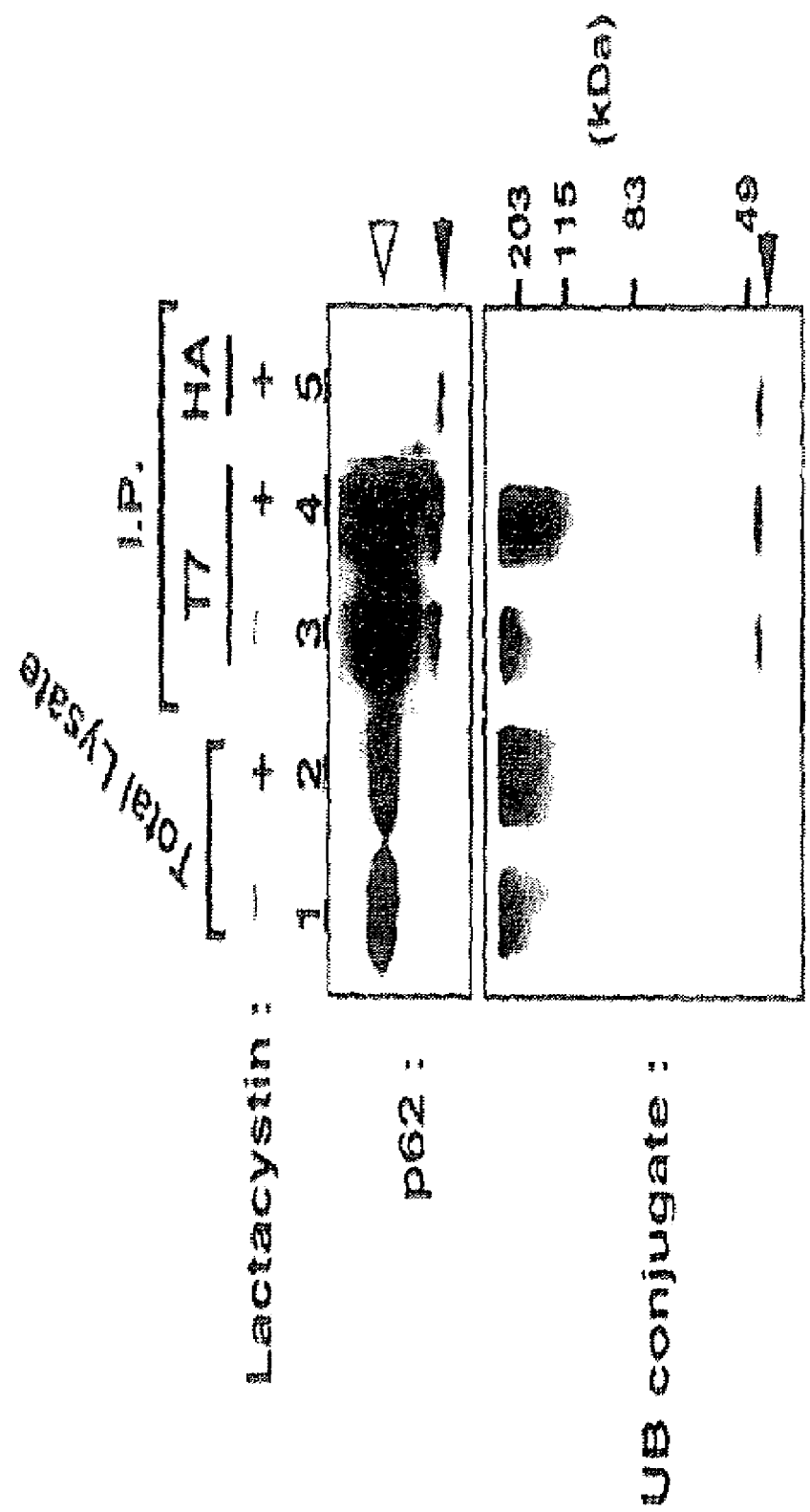
FIG. 27 shows interaction of p62 with ubiquitin-protein conjugates endogenous to HeLa cells. HeLa cells expressing p62.T7 were incubated in the presence or absence of lactacystin and lysed. p62.T7 was immunoprecipitated from the lysates using anti-T7 monoclonal antibody, and the coprecipitated p62 and ubiquitin-protein conjugates, and then detected by immunoblot using polyclonal anti-p62 and ubiquitin-conjugate antisera.

Multiubiquitin binds to p62. FIGS. 26A-26C show multiubiquitin chain binding to p62 and Mcb1. (A) Purified recombinant arabidopsis Mcb1 (Mcb1), GST fused p62 ubiquitin binding region (GST. P62C259), and GST were subjected to SDS-PAGE and transferred to nitrocellulose. The membrane was either stained with Ponceau S (left panel) or incubated with $^{125}$I-labeled multiubiquitin chains, washed, and subjected to autoradiography (right panel). (B) GST or GST.p62C259 was incubated with $^{125}$I-labeled multiubiquitin chains in solution, the bound chains were precipitated using glutathione coupled agarose beads, and the amount of bound chains measured by γ-counting. (C) $^{125}$I-labeled multiubiquitin chains precipitated in (B) were eluted from the beads by heating in SDS-containing buffer; the eluent was separated by SDS PAGE and the profile of multiubiquitin chains analyzed by autoradiography. The mixtures of $^{125}$I-labeled multiubiquitin chains are included for comparison (free chains)

p62 interacts with ubiquitin-protein conjugates endogenous to HeLa cells. FIG. 27 shows interaction of p62 with ubiquitin-protein conjugates endogenous to HeLa cells. HeLa cells expressing p62.T7 were incubated in the presence or absence of lactacystin and lysed. p62.T7 was immunoprecipitated from the lysates using anti-T7 monoclonal antibody, and the coprecipitated p62 and ubiquitin-protein conjugates, and then detected by immunoblot using polyclonal anti-p62 and ubiquitin-conjugate antisera.

Figure 28:
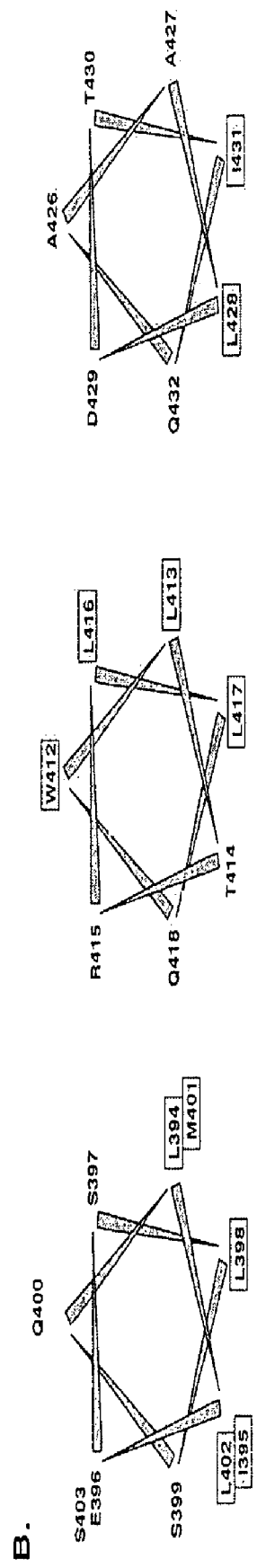
FIGS. 28A-28B show (A) amino acid sequence of the ubiquitin binding domain of p62. A neural network method was used to predict the secondary structure of the ubiquitin binding domain of p62. Predicted α-helical regions are underlined. (B) The predicted α-helical regions are drawn on helical wheels. Hydrophobic residues are boxed.

Ubiquitin binding domain of p62 is elucidated by the neural network method. FIGS. 28A and B show (A) amino acid sequence of the ubiquitin binding domain of p62 (SEQ ID NO: 1). A neural network method was used to predict the secondary structure of the ubiquitin binding domain of p62. Predicted α-helical regions are underlined. (B) The predicted α-helical regions are drawn on helical wheels. Hydrophobic residues are boxed.

Some of these mutant p62 proteins were assayed for binding to multiubiquitin chain. TABLE 1 shows multiubiquitin chain binding to mutant p62 proteins (p62 proteins were tested as GST fusions bound to G-beads). Purified recombinant GST fused p62 ubiquitin binding region (GST.P62C259), GST and various p62 mutant proteins were incubated with $^{125}$I-labeled multiubiquitin chains in solution, the bound chains were precipitated using glutathione coupled agarose beads, and the amount of bound chains measured by γ-counting. Results show that hydrophobic residues in the uniquitin chain binding region is important in binding with ubiquitin chains.

TABLE 1

| Mutant | Multiubiquitin Chain Bound cpm (%) |
|---|---|
| None[a] | 90 (0%) |
| p62 | 5214 (100%) |
| $L_{394}/L_{395}$ → A/A | 877 (17%) |
| $M_{401}/L_{402}$ → A/A | 69 (0%) |
| $W_{412}/L_{413}$ → A/A | 108 (0%) |
| $L_{416}/L_{417}$ → A/A | 63 (0%) |

Figure 29:
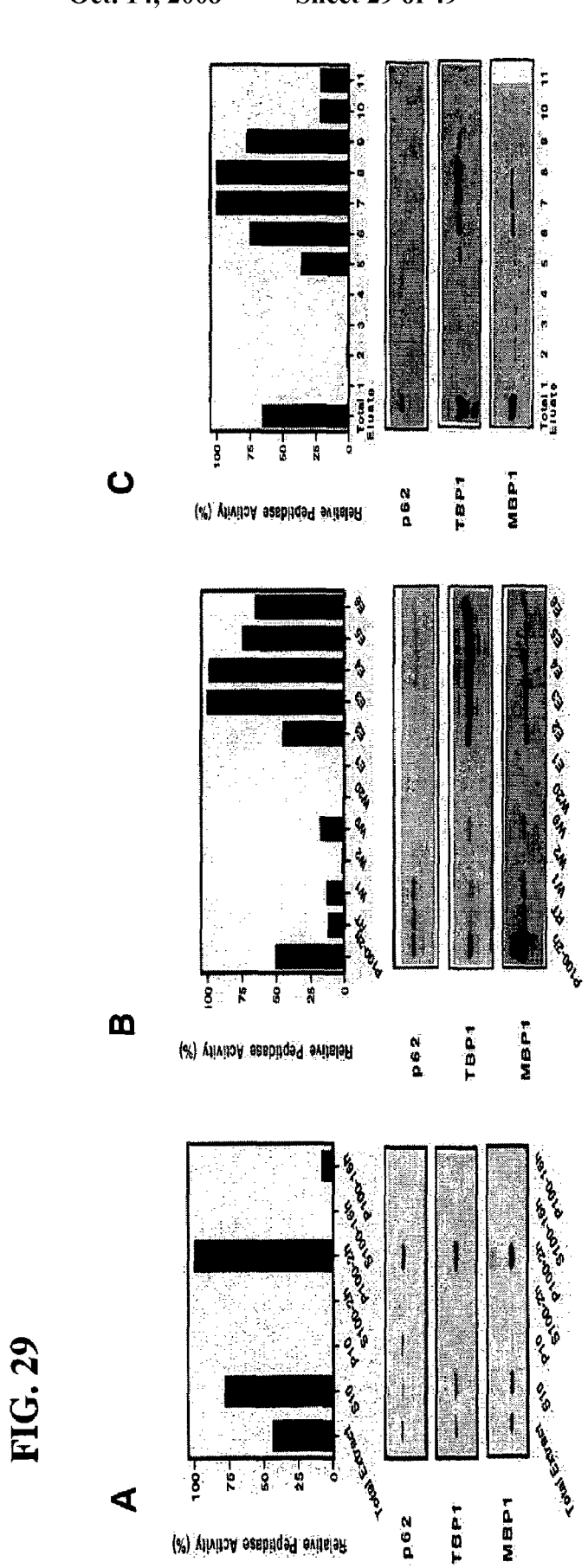
FIGS. 29A-29C show p62 is not associated with the proteasome. (A) 26S proteasome enriched fraction was isolated using differential centrifugation of total lysate from HeLa cells. 5 μg of each fraction was used for peptidase assay and TBP1. (B) 26S proteasome was purified from P100-2 h fraction on a DEAE Affi-gel blue column. 20 μl of each used for peptidase assay and western blot. (C) 26S proteasome was further purified using 15%-40% continuous glycerol gradient. Fractions (500 μl) were collected from the top of the gradient, and 20 μl of each were used for peptidase assay and immunoblot. Other 26S proteasome subunits (ATPases p42, S4. p45 and a 20S core complex subunit p31) were also found in the same fractions as TBP1 by immunoblot analysis (data not shown).
Figure 30:
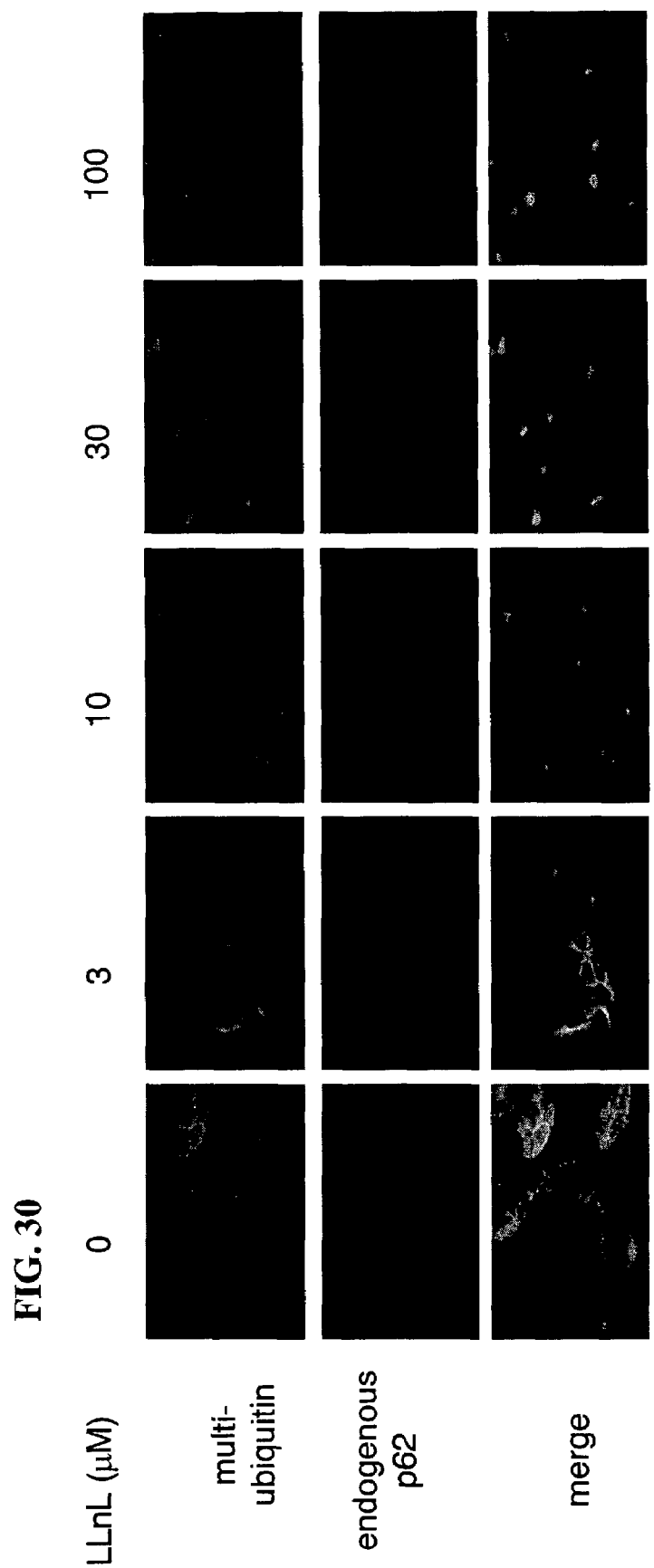
FIG. 30 shows colocalization of p62 with multi-ubiquitin chain after treatment with LLnL in HEK 293 cells. HEK 293 cells were treated with increasing concentrations of LLnL indicated for 16 hours before harvesting. Cells were lysed and immunostained with anti-p62 and anti-ubiquitin antibodies.
Figure 31:
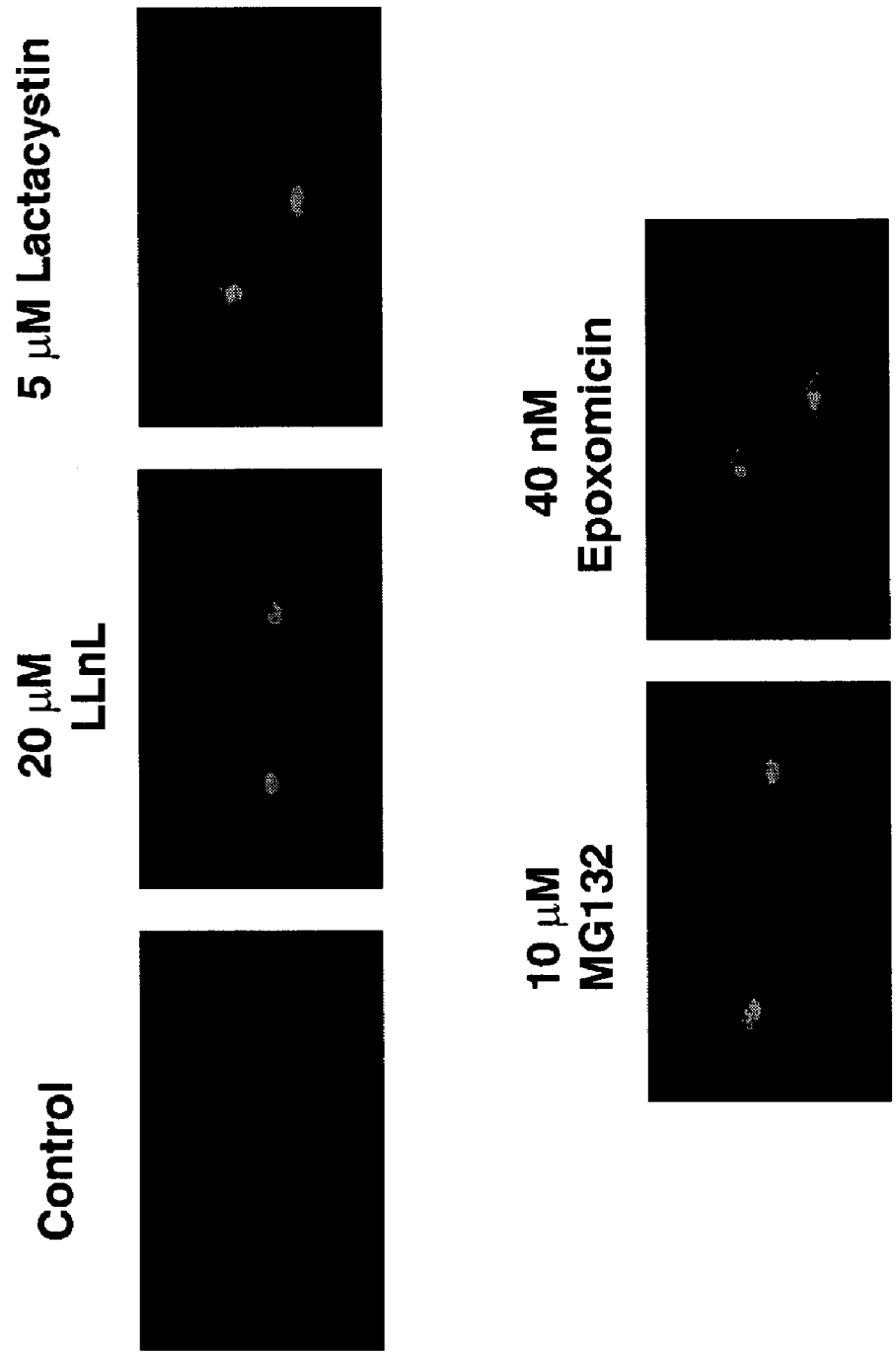
FIG. 31 shows various proteasome inhibitors can induce formation of sequestosome. COS7 cells were treated with several proteasome inhibitors (20 mM ALLN, 5 mM lactacystin, 10 mM MG132 and 50 nM epoxomicin) for 12 hours and immunostained with anti-p62 antibody.
Figure 32:
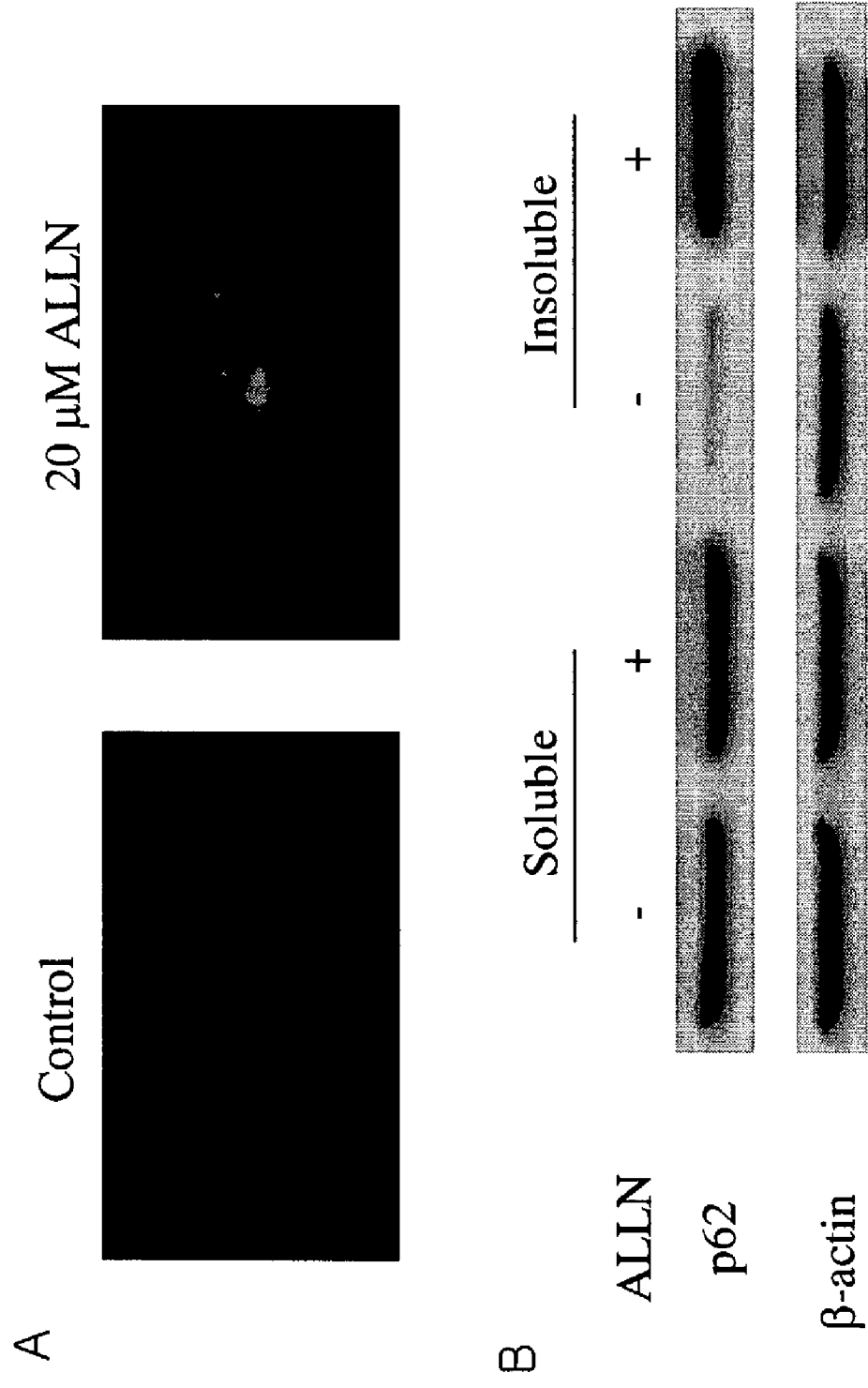
FIGS. 32A-32B show p62 forms cytosolic inclusion structures, named sequestosome, by proteasome inhibitor LLnL. (A) p62 accumulates in sequestosome by treatment with LLnL. COS7 cells were incubated in the presence of 20 mM LLnL for 12 hours and processed for immunofluorescent microscopy with antibodies to p62. (B) The level of p62 is increased in detergent-insoluble fraction by exposure to LLnL. COS7 cells were incubated in the presence of carrier (DMSO) or 20 mM LLnL for 12 hours before harvesting. Cells were lysed and separated into triton X-100 soluble and insoluble fractions. Equivalent loading of samples was confirmed by reprobing the blot with anti-b-actin antibody.

[a]Sample contains G-beads alone.

p62 is not associated with the proteasome. FIGS. 29A-29C show that p62 is not associated with the proteasome. (A) 26S proteasome enriched fraction was isolated using differential centrifugation of total lysate from HeLa cells. 5 μg of each fraction was used for peptidase assay and TBP1. (B) 26S proteasome was purified from P100-2 h fraction on a DEAE Affi-gel blue column. 20 μl of each used for peptidase assay and western blot. (C) 26S proteasome was further purified using 15%-40% continuous glycerol gradient. Fractions (500 μl) were collected from the top of the gradient, and 20 μl of each were used for peptidase assay and immunoblot. Other 26S proteasome subunits (ATPases p42, S4. p45 and a 20S core complex subunit p31) were also found in the same fractions as TBP1 by immunoblot analysis (data not shown).

p62 is colocalized with multi-ubiquitin chain after treatment with proteasome inhibitor. FIG. 30 shows colocalization of p62 with multi-ubiquitin chain after treatment with LLnL in HEK 293 cells. HEK 293 cells were treated with increasing concentrations of LLnL indicated for 16 hours before harvesting. Cells were lysed and immunostained with anti-p62 and anti-ubiquitin antibodies. FIG. 31 shows that various proteasome inhibitors can induce formation of sequestosome. COS7 cells were treated with several proteasome inhibitors (20 mM ALLN, 5 mM lactacystin, 10 mM MG 132 and 50 nM epoxomicin) for 12 hours and immunostained with anti-p62 antibody. Further, FIGS. 32A-32B show that p62 forms cytosolic inclusion structures, named sequestosome, by proteasome inhibitor LLnL. (A) p62 accumulates in sequestosome by treatment with LLnL. COS7 cells were incubated in the presence of 20 mM LLnL for 12 hours and processed for immunofluorescent microscopy with antibodies to p62. (B) The level of p62 is increased in detergent-insoluble fraction by exposure to LLnL. COS7 cells were incubated in the presence of carrier (DMSO) or 20 mM LLnL for 12 hours before harvesting. Cells were lysed and separated into triton X-100 soluble and insoluble fractions. Equivalent loading of samples was confirmed by reprobing the blot with anti-b-actin antibody.

Figure 33:
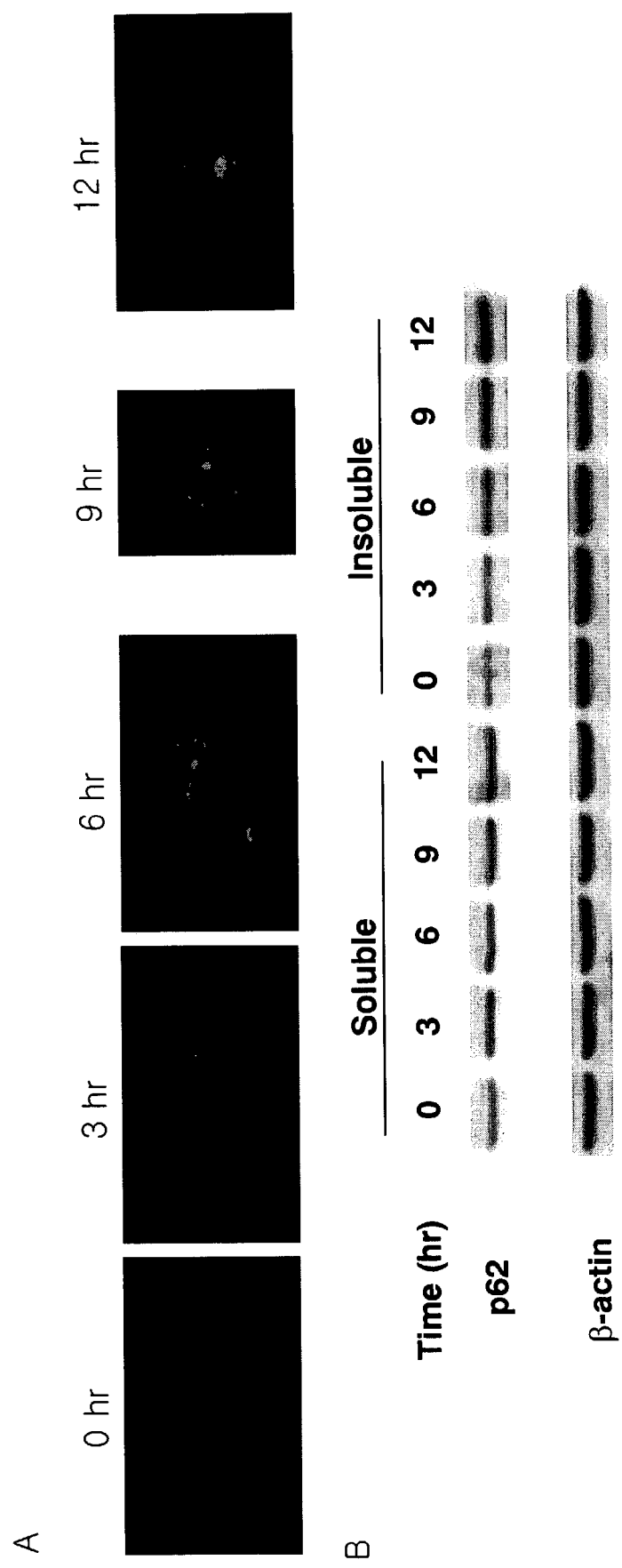
FIGS. 33A-33B show time-dependent p62-sequestosome formation. (A) COS7 cells were incubated in the presence of 20 mM LLnL for times indicated and was immunostained with antibodies to p62. (B) Time course of p62 elevation in detergent-insoluble fraction. After treatment with 20 mM LLnL for the times indicated, COS7 cells were harvested, lysed and separated into detergent-soluble and -insoluble fractions. Equivalent loading of samples was confirmed by reprobing the blot with anti-b-actin antibody.

Further, FIGS. 33A-33B show time-dependent p62-sequestosome formation. (A) COS7 cells were incubated in the presence of 20 mM LLnL for times indicated and was immunostained with antibodies to p62. (B) Time course of p62 elevation in detergent-insoluble fraction. After treatment with 20 mM LLnL for the times indicated, COS7 cells were harvested, lysed and separated into detergent-soluble and -insoluble fractions. Equivalent loading of samples was confirmed by reprobing the blot with anti-b-actin antibody.

Figure 34:
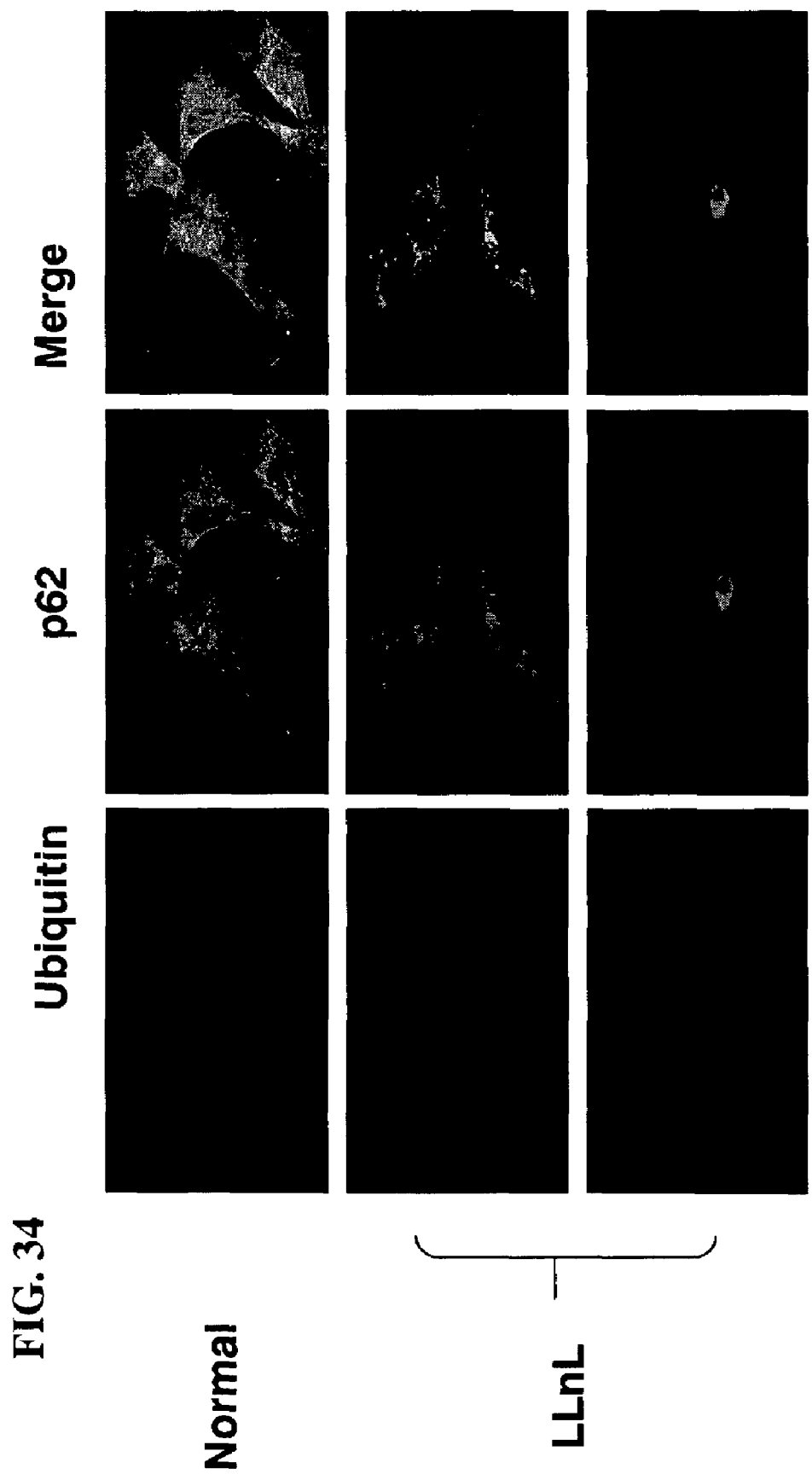
FIG. 34 shows ubiquitin positive p62 inclusion formation in mouse embryonic fibroblasts (MEFs). MEF cells were incubated in the presence of 20 mM LLnL for 12 hours and were immunostained with anti-p62 and ubiquitin antibodies.
Figure 35:
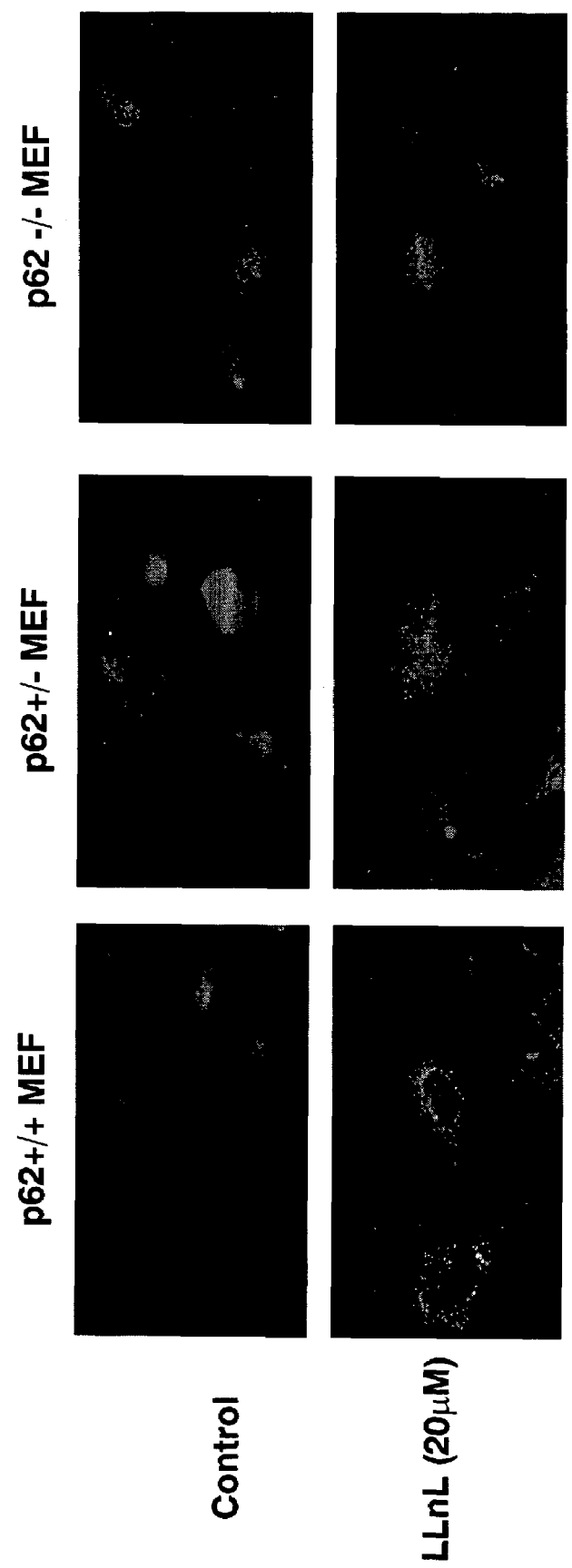
FIG. 35 shows p62 gene dosage-dependent UB-inclusion formation. MEFs from p62 wild, heterozygous or null embryos were incubated in the presence or absence of LLnL (20mM) for 12 hours and immunostained with anti-ubiquitin antibodies.
Figure 36:
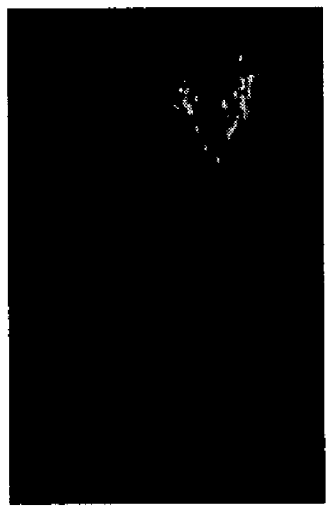
FIG. 36 shows p62 overexpression in p62 −/− MEF rescue ubiquitin inclusion formation by proteasome inhibitor. MEFs from p62 null embryos were transfected with a p62 expression vector. After 24 hours, these cells were incubated in the presence of LLnL (20 mM) for 12 hours and immunostained with anti-p62 and anti-ubiquitin antibodies.
Figure 36:
Figure 36:
Figure 36:
Figure 36:
Figure 36:
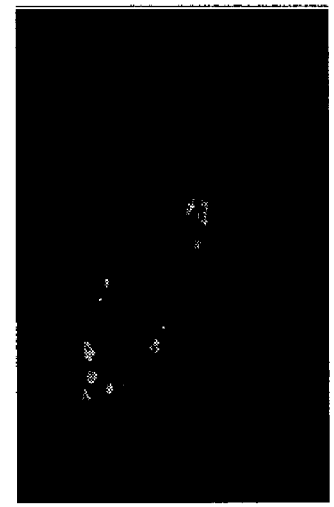

Ubiquitin-p62 inclusion is formed in mouse embryonic fibroblasts. FIG. 34 shows ubiquitin positive p62 inclusion formation in mouse embryonic fibroblasts (MEFs). MEF cells were incubated in the presence of 20 mM LLnL for 12 hours and were immunostained with anti-p62 and ubiquitin antibodies. Furthermore, FIG. 35 shows p62 gene dosage-dependent UB-inclusion formation. MEFs from p62 wild, heterozygous or null embryos were incubated in the presence or absence of LLnL (20 mM) for 12 hours and immunostained with anti-ubiquitin antibodies. p62 wild type MEF formed ubiquitin-positive inclusions well while p62-null MEF cannot form the inclusion at all and p62-heterozygote can form the inclusion but less efficiently. FIG. 36 shows that p62 overexpression in p62 −/− MEF rescues ubiquitin inclusion formation by proteasome inhibitor. MEFs from p62 null embryos were transfected with a p62 expression vector. After 24 hours, these cells were incubated in the presence of LLnL (20 mM) for 12 hours and immunostained with anti-p62 and anti-ubiquitin antibodies.

Figure 37:
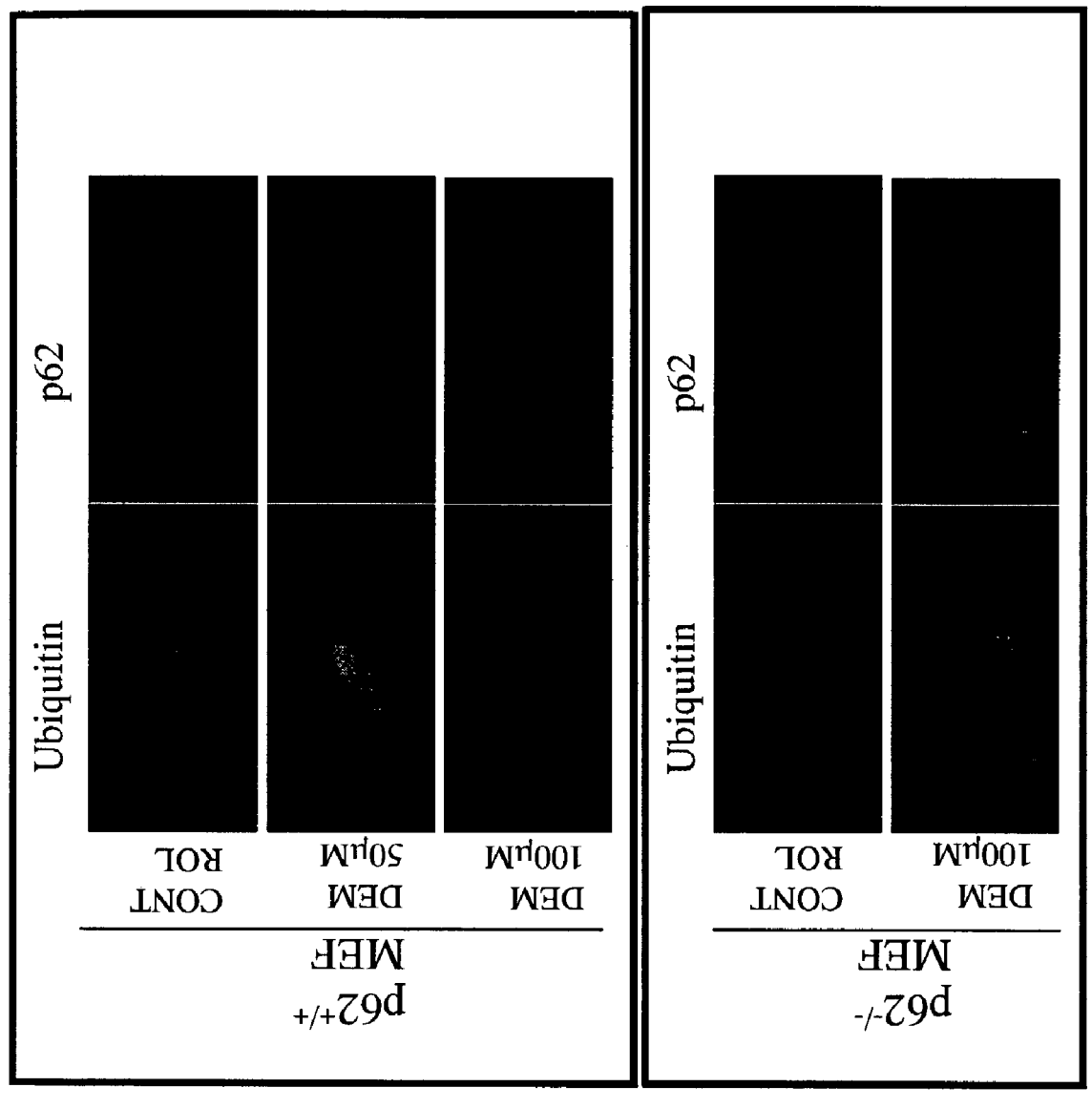
FIGS. 37A-37B show p62 aggregates formed in MEF in the presence of GSH-depletor. MEFs were incubated with or without DEM for 12 h. p62 wt (A) and p62 null (B) MEFs were immunolabeled with antibodies against p62 and Ubiquitin. Bar=10 µm.

Further, p62-positive intracellular inclusion are also formed by oxidative stress. For instance, FIGS. 37A-37B show the formation of p62- or ubiquitin-positive aggregates in MEF in the presence of glutathione (GSH) depletory, diethylmaleate (DEM). MEFs were incubated with or without DEM for 12 h. p62 wt (A) and p62 null (B) MEFs were immunolabeled with antibodies against p62 and ubiquitin. DEM can induce the ubiquitin-positive inclusions only in the p62-wild type MEF but not in p62-null MEF. Thus, p62 has a function to collect misfolded and/or ubiquitinated intracellular proteins and make intracellular inclusions.

Figure 38:
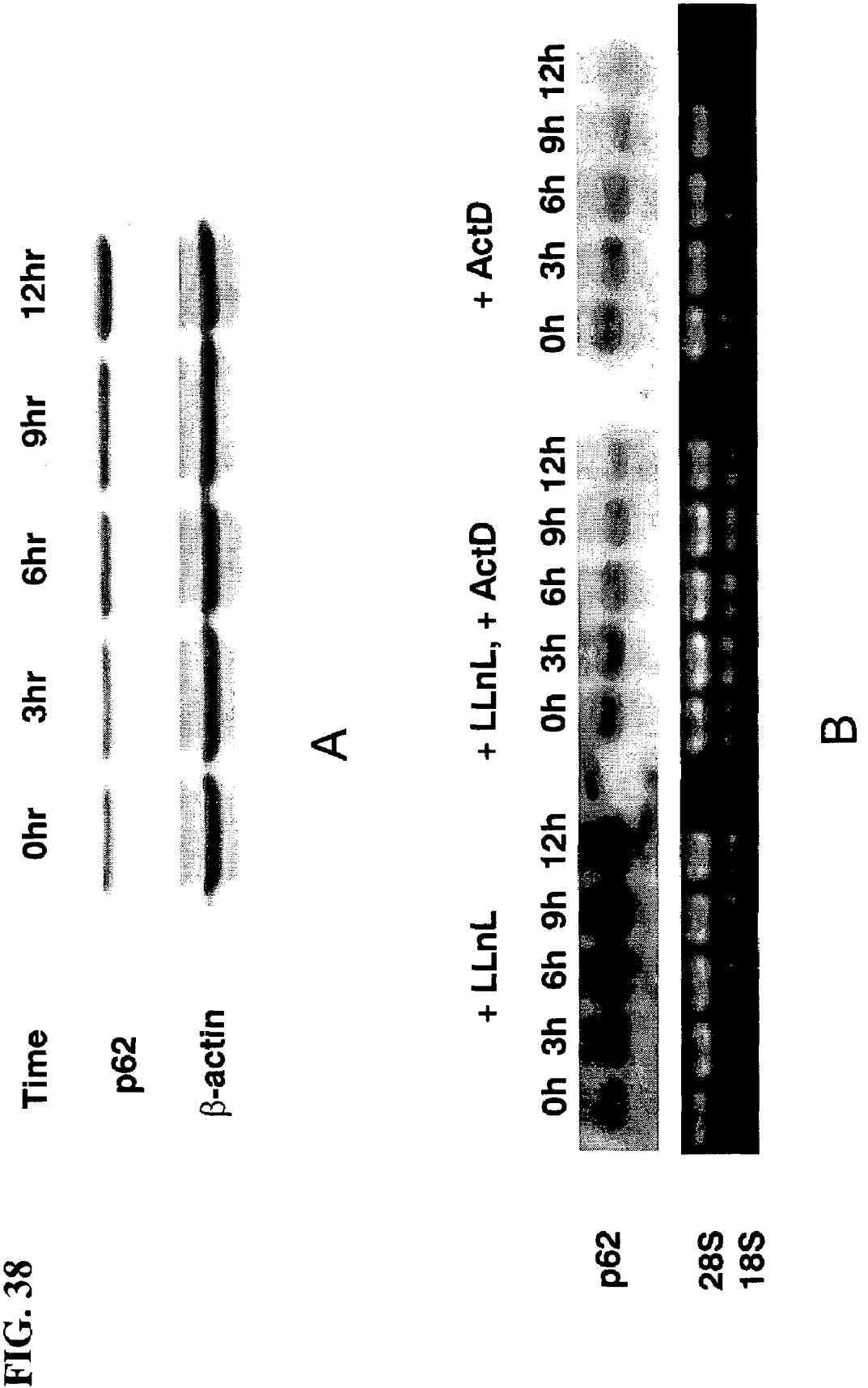
FIGS. 38A-38B show activation of the p62 gene in response to proteasome inhibitor LLnL. (A) COS7 cells were treated with 20 mM LLnL for the indicated time periods and cell lysates were analyzed by immunoblotting using anti-p62 antibodies. Equivalent loading was confirmed by anti-beta-actin immunoblotting. (B) COS7 cells were treated with 20 mM LLnL in the absence (left upper panel) or presence (middle and right upper panels) of actinomycin D. Total RNA was extracted from the untreated and treated cells and equal amounts (10 mg) of RNA were analyzed. Equivalent loading of RNA was confirmed by staining 28S and 18S ribosomal RNA with ethidium bromide (lower panel).

FIGS. 38A-38B show activation of the p62 gene in response to proteasome inhibitor LLnL. (A) COS7 cells were treated with 20 mM LLnL for the indicated time periods and cell lysates were analyzed by immunoblotting using anti-p62 antibodies. Equivalent loading was confirmed by anti-beta-actin immunoblotting. (B) COS7 cells were treated with 20 mM LLnL in the absence (left upper panel) or presence (middle and right upper panels) of actinomycin D. Total RNA was extracted from the untreated and treated cells and equal amounts (10 mg) of RNA were analyzed. Equivalent loading of RNA was confirmed by staining 28S and 18S ribosomal RNA with ethidium bromide (lower panel). As decay rates for the p62 mRNA with or without actinomycin in the presence of LLnL are the same, the increase of p62 level by proteasomal inhibition is due to activation of the p62 gene.

Figure 39:
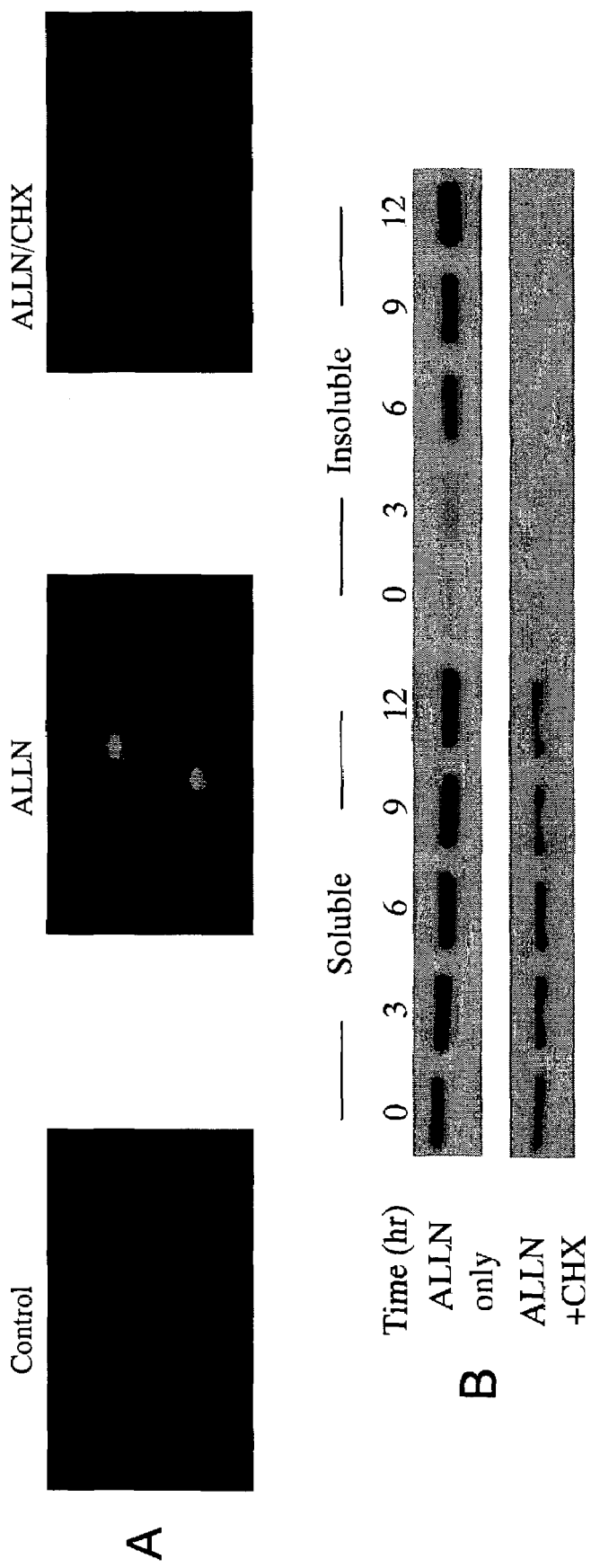
FIGS. 39A-39B show that sequestosome formation requires p62 gene activation. (A) COS7 cells were treated with 20 mM LLnL in the presence or absence of cycloheximide for 12 hours and immunostained with antibodies to p62. (B) COS7 cells were exposed to 20 mM LLnL in the presence (top panel) or absence (lower panel) of cycloheximide for the times indicated. The treated cells were harvested, lysed and separated into 0.5% triton X-100 soluble and insoluble fractions. These lysates were immunoblotted using anti-p62 antibodies.

Sequestosome formation requires p62 gene activation (FIGS. 39A-39B). (A) COS7 cells were treated with 20 mM LLnL in the presence or absence of cycloheximide for 12 hours and immunostained with antibodies to p62. (B) COS7 cells were exposed to 20 mM LLnL in the presence (top panel) or absence (lower panel) of cycloheximide for the times indicated. The treated cells were harvested, lysed and separated into 0.5% triton X-100 soluble and insoluble fractions. These lysates were immunoblotted using anti-p62 antibodies. Cellular inclusion was not formed when cells were treated with proteasomal inhibitor in the presence of translational inhibitor, cycloheximide. Under this condition, p62 cellular level was not increased and, particularly, p62 in the detergent insoluble fraction was almost undetectable. Thus, it is likely that activation of the p62 gene followed by efficient p62 protein synthesis is required for such inclusion formation and that proteins in the inclusion are insoluble to detergent such as Triton X-100.

Figure 40:
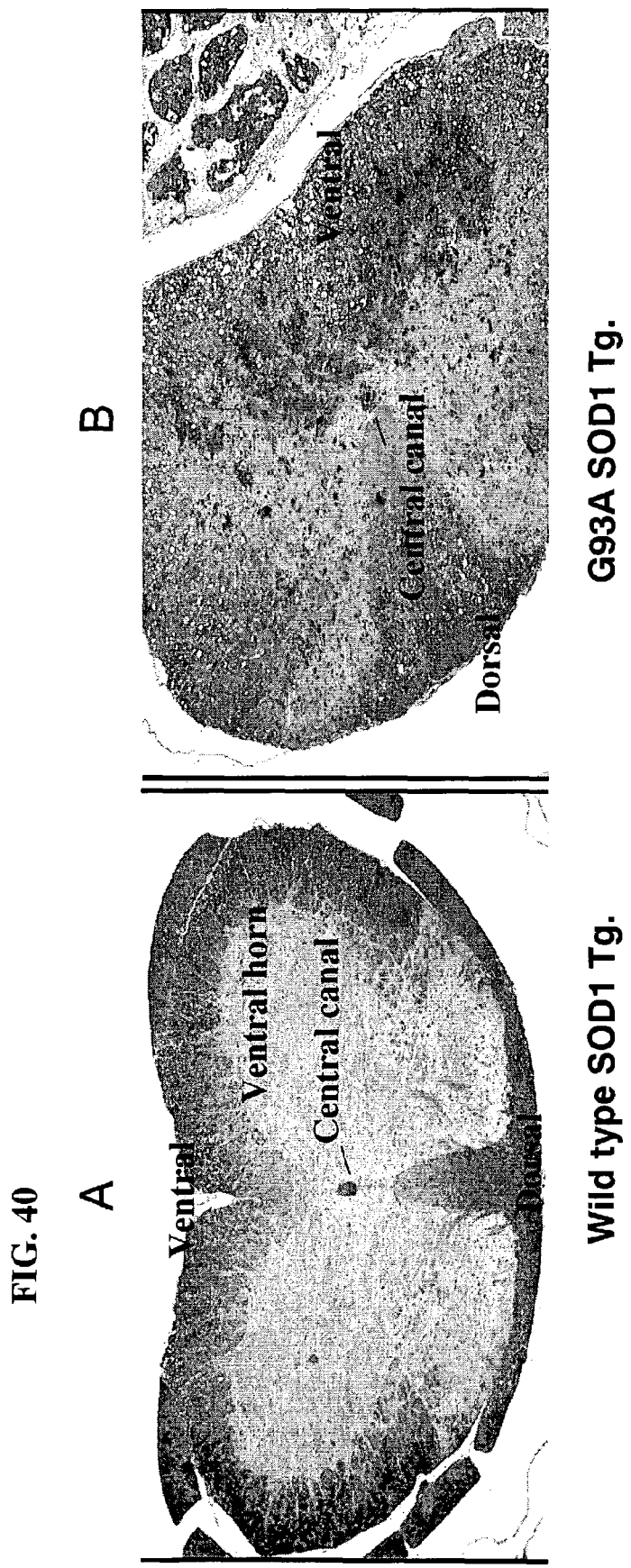
FIGS. 40A-40B show ALS model mice showing p62 inclusion in their lumbar spinal cords. Transgenic mice expressing (A) the wild type human SOD1 or (B) ALS-related mutant human SOD1 (G93A) gene were sacrificed at 16 weeks of age and their lumbar spinal cord region were stained with hematoxylin and anti-p62 antibody. p62 was detected primarily in motor neurons of the ventral horn region of the mutant transgenic mice spinal cord sections. In contrast, little or no staining with the antibody was observed in the ventral horn region of the wild-type transgenic mice sections.
Figure 41:
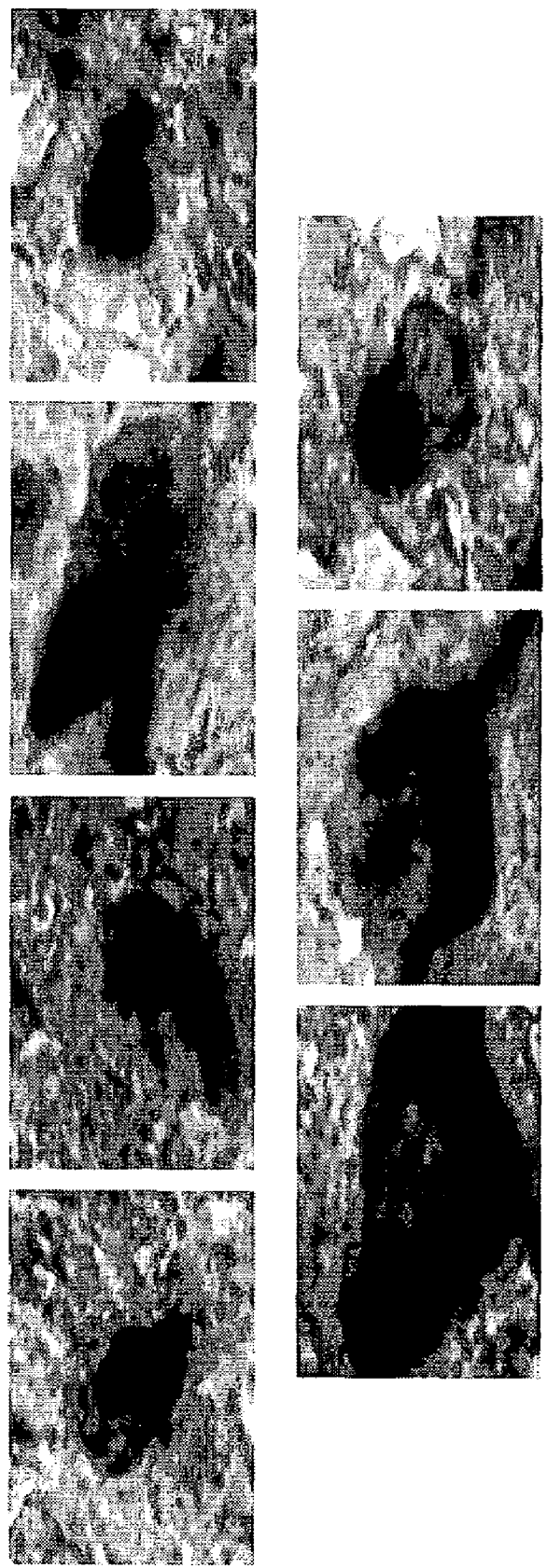
FIG. 41 shows p62 inclusion in lumbar spinal cords of ALS mice. Transgenic mice expressing the wild type human SOD1 or ALS-related mutant human SOD1 (G93A) gene were sacrificed at 16 weeks of age and their lumbar spinal cord region were stained with hematoxylin and anti-p62 antibody. Perinuclear inclusions of p62 were detected using p62 immunostaining.
Figure 42:
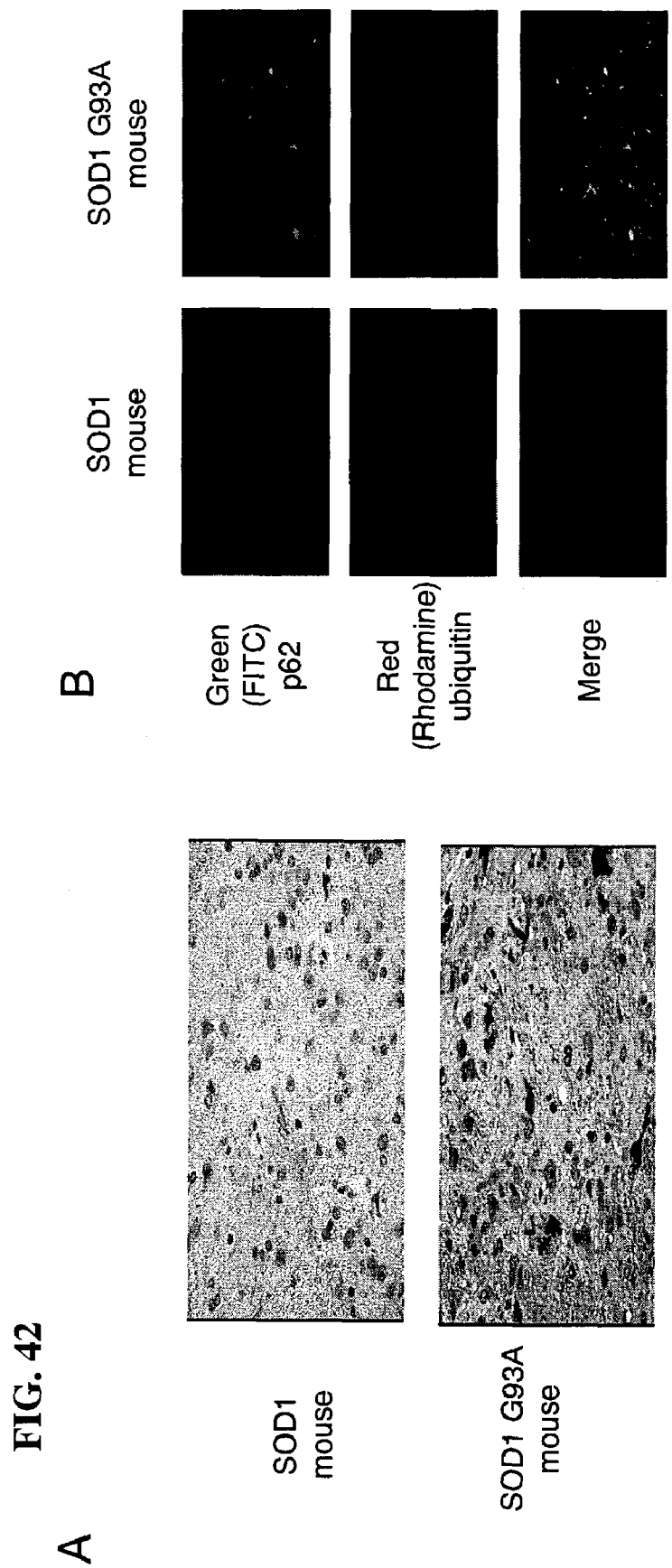
FIGS. 42A-42B show that p62 inclusion in ALS mice are ubiquitin positive. Transgenic mice expressing wild type human SOD1 or ALS-related mutant human SOD1 (G93A) gene were sacrificed at 16 weeks of age and their lumbar spinal cord region were (A) stained with anti-p62 antibody and (B) co-stained with anti-p62 antibody and anti-ubiquitin antibody.
Figure 43:
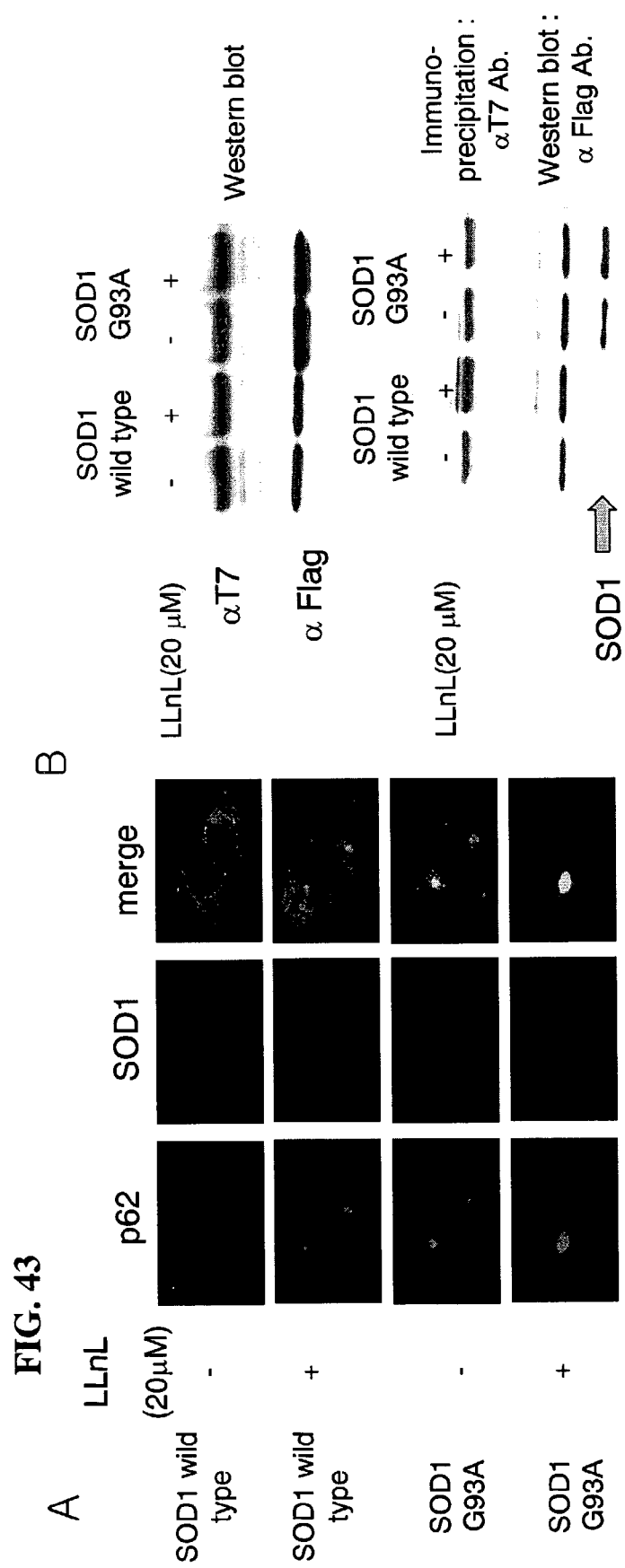
FIGS. 43A-43B show p62 colocalizes and coprecipitates with mutant SOD1(G93A). (A) COS7 cells were transfected with flag tagged SOD1 or SOD1G93A mutant expressing plasmids. After 24 hours, these cells were treated or not treated with 20 uM LLnL for 12 hours and immunostained with anti-flag antibody and anti-p62 antibody. (B) Flag tagged SOD1 or SOD1G93A expressing plasmids were co-transfected with T7 tagged p62 expressing plasmid. These cells were incubated for 12 hours in the presence or absence of proteasome inhibitor LLnL (20mM) and immunoprecipitated with anti-T7 antibody. Precipitated proteins were analyzed by immunoblotting using anti-flag antibody.

(vii) Role of p62 Positive Inclusion in ALS p62 inclusions are found in ALS model mice. FIGS. 40A-40B show ALS model mice showing p62 inclusion in their lumbar spinal cords. Transgenic mice expressing (A) the wild type human SOD1 or (B) ALS-related mutant human SOD1 (G93A) gene were sacrificed at 16 weeks of age and their lumbar spinal cord region were stained with hematoxylin and anti-p62 antibody. p62 was detected primarily in motor neurons of the ventral horn region of the mutant transgenic mice spinal cord sections. In contrast, little or no staining with the antibody was observed in the ventral horn region of the wild-type transgenic mice sections. FIG. 41 shows p62 inclusion in lumbar spinal cords of ALS mice. Transgenic mice expressing the wild type human SOD1 or ALS-related mutant human SOD1 (G93A) gene were sacrificed at 1.6 weeks of age and their lumbar spinal cord region were stained with hematoxylin and anti-p62 antibody. Perinuclear inclusions of p62 were detected using p62 immunostaining. Further, FIGS. 42A-42B show that P62 inclusion in ALS mice is ubiquitin positive. Transgenic mice expressing wild type human SOD1 or ALS-related mutant human SOD1 (G93A) gene were sacrificed at 16 weeks of age and their lumbar spinal cord region were (A) stained with anti-P62 antibody and (B) co-stained with anti-P62 antibody and anti-ubiquitin antibody.

p62 colocalizes and coprecipitates with mutant SOD1 (G93A) (FIGS. 43A-43B). (A) COS7 cells were transfected with flag tagged SOD1 or SOD1G93A mutant expressing plasmids. After 24 hours, these cells were treated or not treated with 20 uM LLnL for 12 hours and immunostained with anti-flag antibody and anti-p62 antibody. (B) Flag tagged SOD1 or SOD1G93A expressing plasmids were co-transfected with T7 tagged p62 expressing plasmid. These cells were incubated for 12 hours in the presence or absence of proteasome inhibitor LLnL (20 mM) and immunoprecipitated with anti-T7 antibody. Precipitated proteins were analyzed by immunoblotting using anti-flag antibody. Results shows that p62 binds directly to the mutant but not to wild type SOD-1 and that p62 and mutant SOD-1G93A colocalizes in the same inclusion. As p62 drives intracellular inclusion formation, inclusions found in various neurodegenerative diseases including ALS are likely formed by p62.

(viii) Redox Biochemistry

Figure 44:
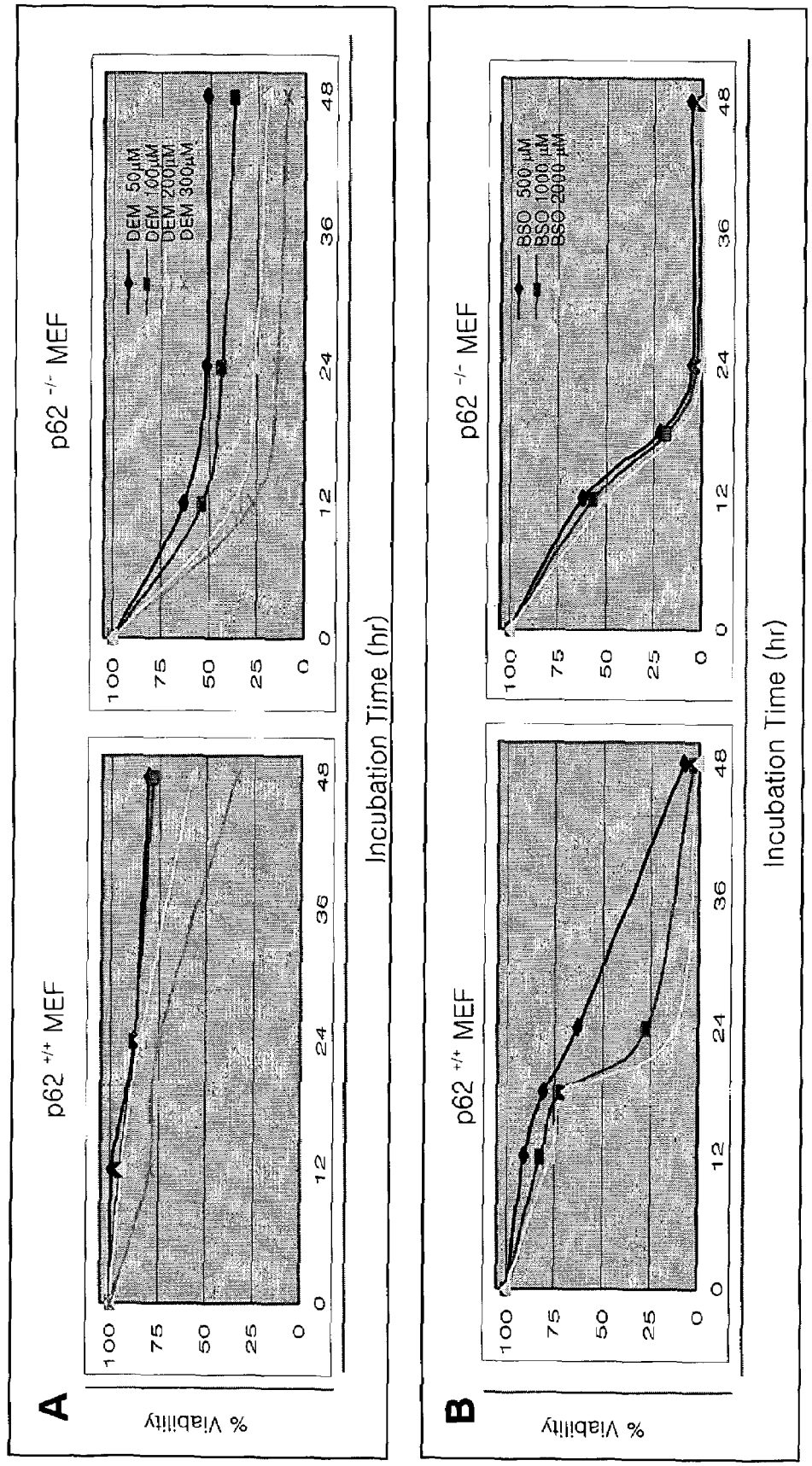
FIGS. 44A-44B show effects of glutathione depletion on cell viability in p62+/+ and p62−/− mouse embryo fibroblast (MEF). Cell viability was assessed with a methylthiazolium (MTT) assay, which measures mitochondrial dehydrogenase activity of viable cells spectrophotometrically. MEF ($3 \times 10^3$ cells/well) in 96-well plates were treated with different concentrations of DEM (A) or BSO (B) washed with PBS and then incubated with 0.5 mg/ml MTT in PBS for 4 h. To solubilize the formazan products, 100 ml DMSO was added. The absorption values at 570 nm were determined.
Figure 48:
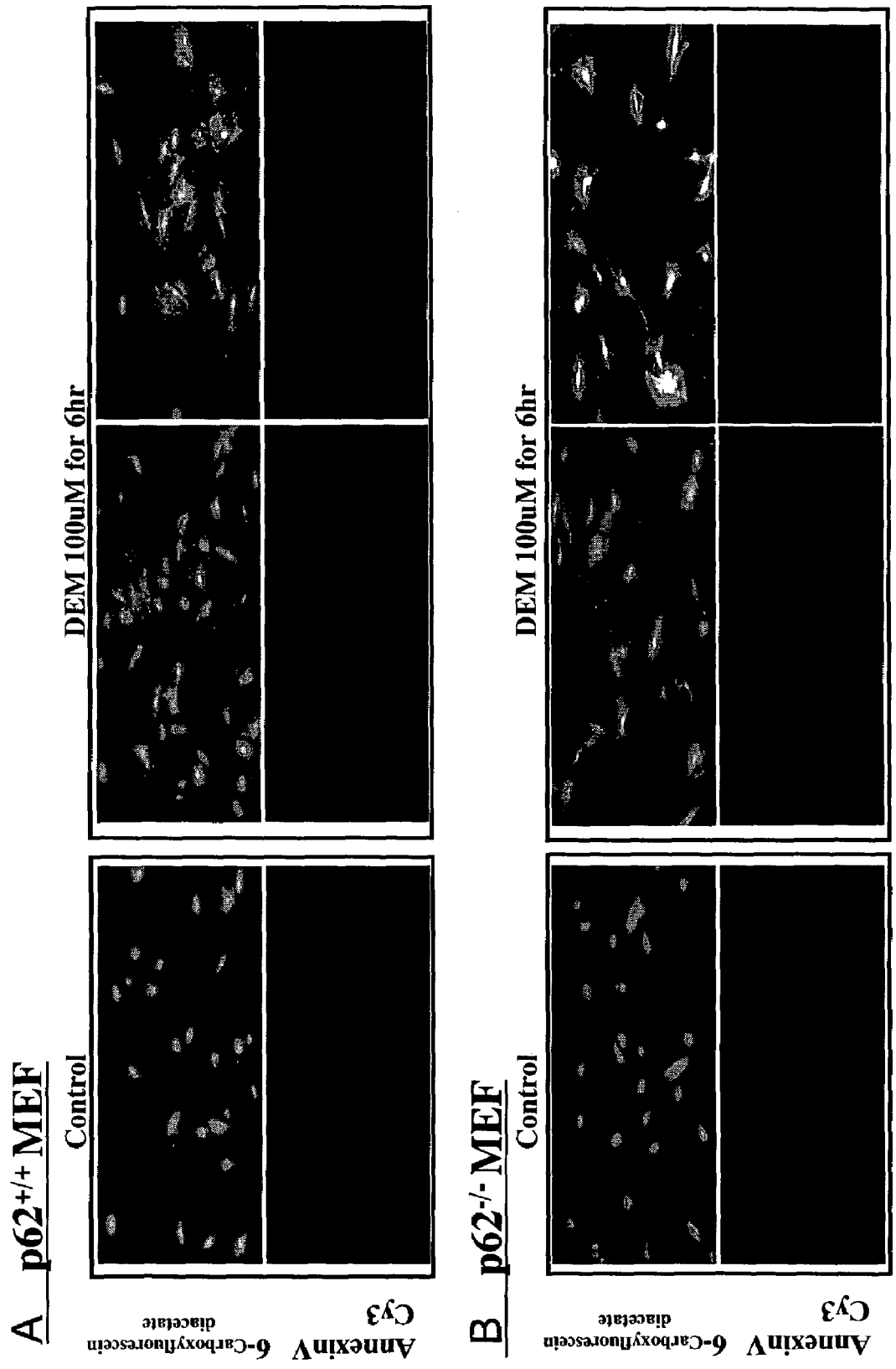
FIGS. 48A-48B show annexin V-binding assay at 6 hr in p62+/+ and p62−/− mouse embryo fibroblast (MEF) after exposure to DEM. Phosphatidylserine membrane translocation was evaluated with annexin V Cy3. To differentiate between apoptotic and necrotic cells that also show translocation of phosphatidylserine, 6-carboxyfluorescein diacetate (6-CFDA) was used in combination with Ann V-Cy3. The nonfluorescent 6-CFDA enters the cell and is converted to the fluorescent compound 6-carboxyfluorescein (6-CF). This conversion is a function of the esterases present only in living cells. Thus, no fluorescence can be produced in necrotic cells. By fluorescence microscopy, 6-CF is observed as green fluorescence and Ann V-Cy3 as red. p62 wt (A) and p62 null (B) MEF were incubated on a poly-L-lysine-coated slide, treated with diethylmaleate (DEM, 50 mM) for 6 hours, and stained with Ann Vcy3/6-CFDA solution in the presence of calcium, and incubated in the dark for 10 minutes. After washing the excess fluorescent compounds, the slide was covered with a coverslip and readily examined by fluorescent microscopy.

In addition to the above, FIGS. 44A-44B show effects of glutathione depletion on cell viability in p62+/+ and p62−/− mouse embryo fibroblast (MEF). Cell viability was assessed with a methylthiazolium (MTT) assay, which measures mitochondrial dehydrogenase activity of viable cells spectrophotometrically. MEF ($3\times10^3$ cells/well) in 96-well plates were treated with different concentrations of DEM (A) or BSO (B) washed with PBS and then incubated with 0.5 mg/ml MTT in PBS for 4 h. To solubilize the formazan products, 100 ml DMSO was added. The absorption values at 570 nm were determined. Results shows that, when glutathione is depleted, p62-null MEFs die more readily compared with wild type MEFs. This death of p62-null MEFs is an apoptotic process (FIG. 48). Thus, p62 appears to have the function of regulating cellular redox status and/or cellular reactive oxygen species (ROS) generation and scavenging systems.

Mode of cell death was measured. FIGS. 48A-48B show annexin V-binding assay at 6 hr in p62+/+ and p62−/− mouse embryo fibroblast (MEF) after exposure to DEM. Phosphatidylserine membrane translocation was evaluated with annexin V Cy3. To differentiate between apoptotic and necrotic cells that also show translocation of phosphatidylserine, 6-carboxyfluorescein diacetate (6-CFDA) was used in combination with Ann V-Cy3. The nonfluorescent 6-CFDA enters the cell and is converted to the fluorescent compound 6-carboxyfluorescein (6-CF). This conversion is a function of the esterases present only in living cells. Thus, no fluorescence can be produced in necrotic cells. By fluorescence microscopy, 6-CF is observed as green fluorescence and Ann V-Cy3 as red. p62 wt (A) and p62 null (B) MEF were incubated on a poly-L-lysine-coated slide, treated with diethylmaleate (DEM, 50 mM) for 6 hours, and stained with Ann Vcy3/6-CFDA solution in the presence of calcium, and incubated in the dark for 10 minutes. After washing the excess fluorescent compounds, the slide was covered with a coverslip and readily examined by fluorescent microscopy. Annexin V positive cells were readily found in the DEM treated p62-null MEFs. Thus, the reduced cell viability of the p62-null MEFs are due to apoptotic cell death.

Figure 45:
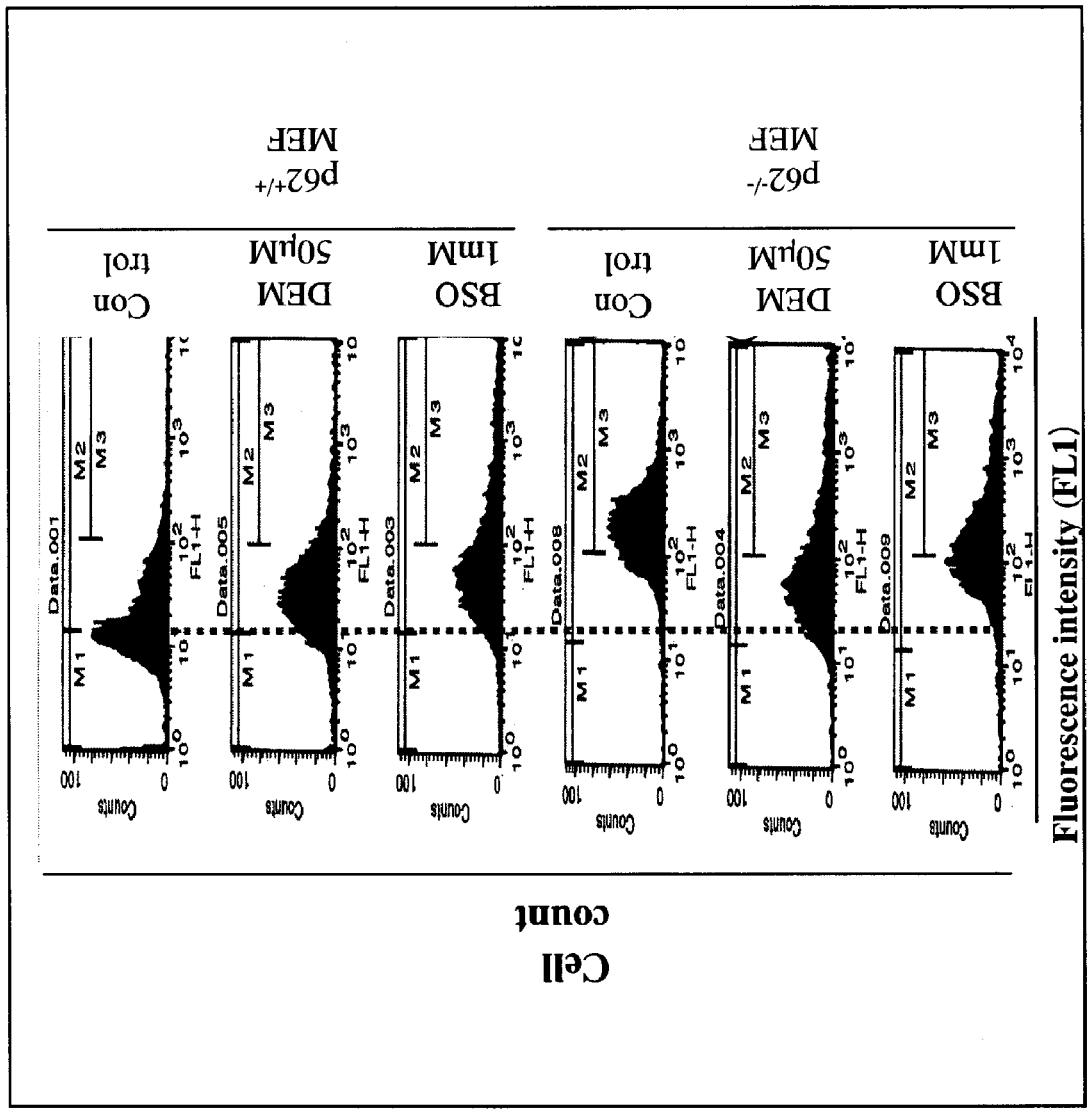
FIG. 45 shows ROS detection in p62+/+ and p62−/− mouse embryo fibroblast (MEF) as measured by DCF fluorescence. Cultures were either treated or not treated with diethylmaleate (DEM, 50 mM) or buthioninesulfoximine (BSO, 1 mM). Cells were harvested 12 hours later, incubated in the presence of 10 mM of the oxidative-sensitive probe DCFH-DA for 30 min at 37° C. and subjected to flow cytometry. Comparative flow cytometry distributions of DCF fluorescence intensity. The histograms represent the number of cells as a function of fluorescence intensity expressed as channel number.

Experiments were carried out to detect reactive oxygen species in p62+/+ and p62−/− mouse embryo fibroblast (MEF) as measured by DCF fluorescence (FIG. 45). Cultures were either treated or not treated with diethylmaleate (DEM, 50 mM) or buthioninesulfoximine (BSO, 1 mM). Cells were harvested 12 hours later, incubated in the presence of 10 mM of the oxidative-sensitive probe DCFH-DA for 30 min at 37° C. and subjected to flow cytometry. Comparative flow cytometry distributions of DCF fluorescence intensity. The histograms represent the number of cells as a function of fluorescence intensity expressed as channel number. Results show that much more ROS accumulated in the p62-null MEFs even without any treatment.

Figure 46:
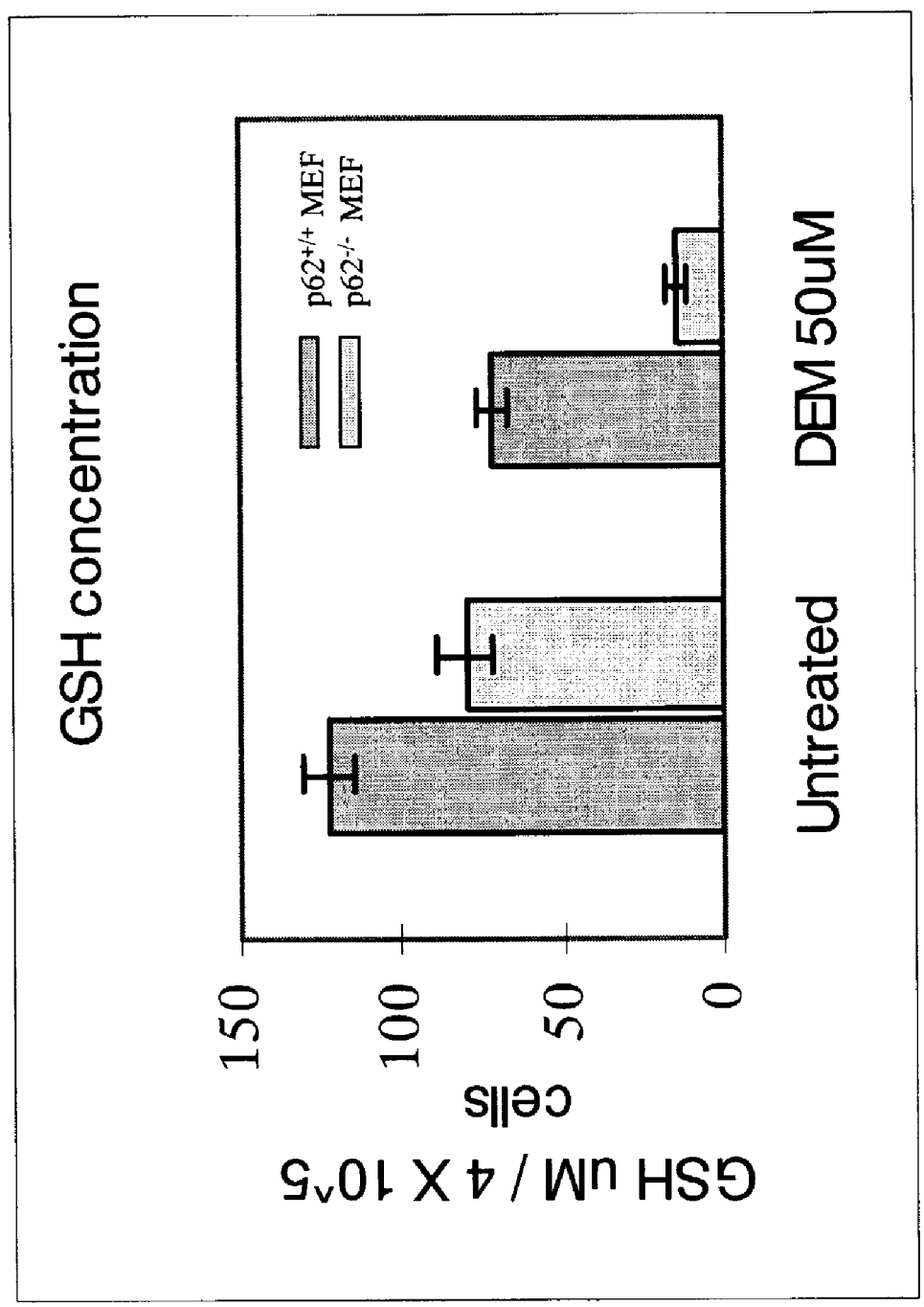
FIG. 46 shows concentrations of total glutathione in the p62+/+ and p62−/− mouse embryo fibroblast (MEF). Cultures were treated or not treated with diethylmaleate (DEM, 50 mM) for 12 hours. The concentration of GSH in MEF ($4 \times 10^5$ cells in 5% metaphosphoric acid) was determined by a colorimetric assay kit according to the manufacturer's instructions. A standard curve was generated using known quantities of GSH.

Total glutathione in MEF was measured. FIG. 46 shows concentrations of total glutathione in the p62+/+ and p62−/− mouse embryo fibroblast (MEF). Cultures were treated or not treated with diethylmaleate (DEM, 50 mM) for 12 hours. The concentration of GSH in MEF ($4\times10^5$ cells in 5% metaphosphoric acid) was determined by a colorimetric assay kit according to the manufacturer's instructions. A standard curve was generated using known quantities of GSH. Results show that only about 60% of glutathione (GSH) is available in the p62-null MEFs compared with the wild type cells and that DEM treatment further sensitively reduced the cellular GSH level in the p62-null MEFs.

Figure 47:
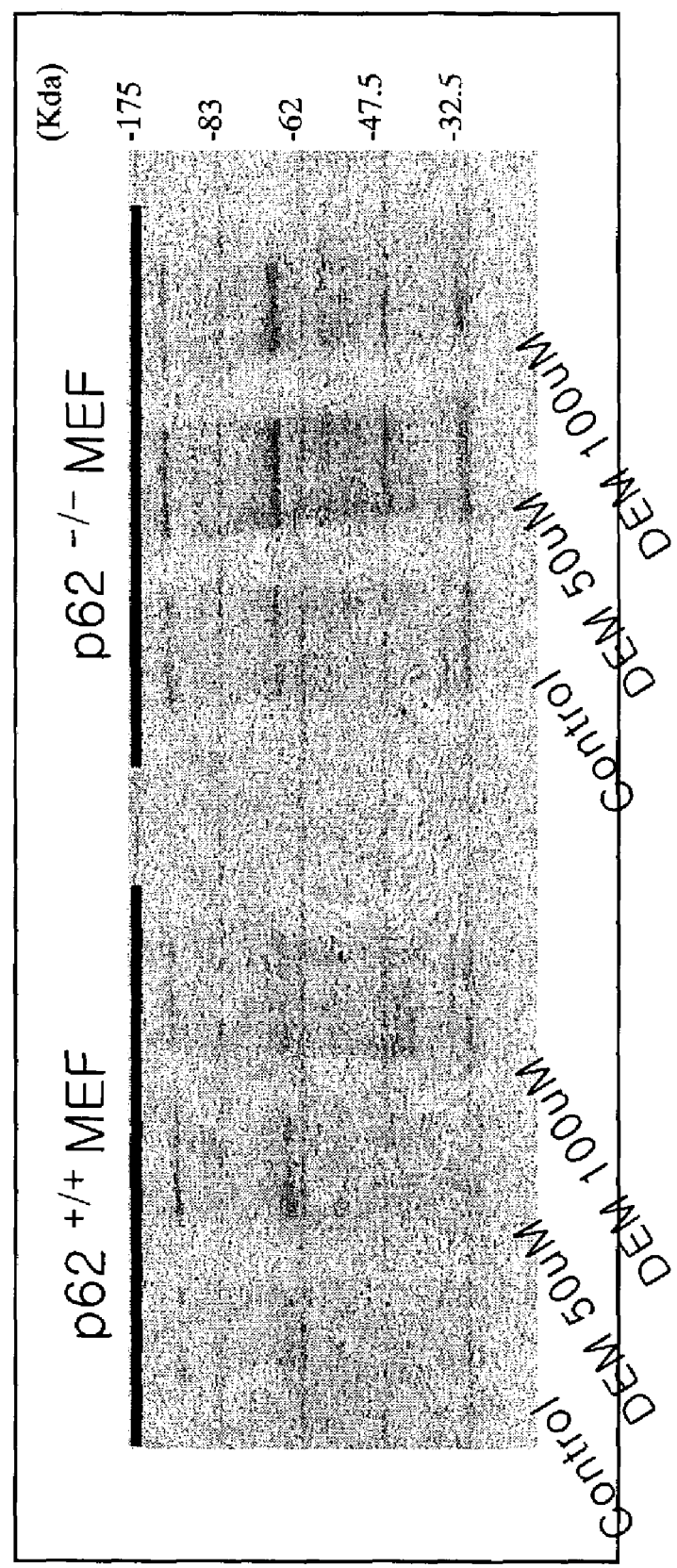
FIG. 47 shows oxidized protein in p62+/+ and p62−/− mouse embryo fibroblast (MEF). Cultures were treated or not treated with diethylmaleate (DEM) for 12 hours. The Oxyblot achieved with 5 mg of cytosolic protein extracts from MEF of p62-wt and p62-null. Extracts were treated with 2,4-dinitrophenylhydrazine, and then submitted to SDS-PAGE on a 10% (w/v) polyacrylamide gel and transferred onto nitrocellulose filter. The blot was processed with anti-DNP antibodies as described by the manufacturer.

Furthermore, FIG. 47 shows oxidized protein in p62+/+ and p62−/− mouse embryo fibroblast (MEF). Cultures were treated or not treated with dietlhylmaleate (DEM) for 12 hours. The Oxyblot achieved with 5 mg of cytosolic protein extracts from MEF of p62-wt and p62-null. Extracts were treated with 2,4-dinitrophenylhydrazine, and then submitted to SDS-PAGE on a 10% (w/v) polyacrylamide gel and transferred onto nitrocellulose filter. The blot was processed with anti-DNP antibodies as described by the manufacturer. As a result of reduced GSH level and increased ROS in the cells, greater amount of oxidized proteins accumulated in the p62-null MEFs.

Figure 49:
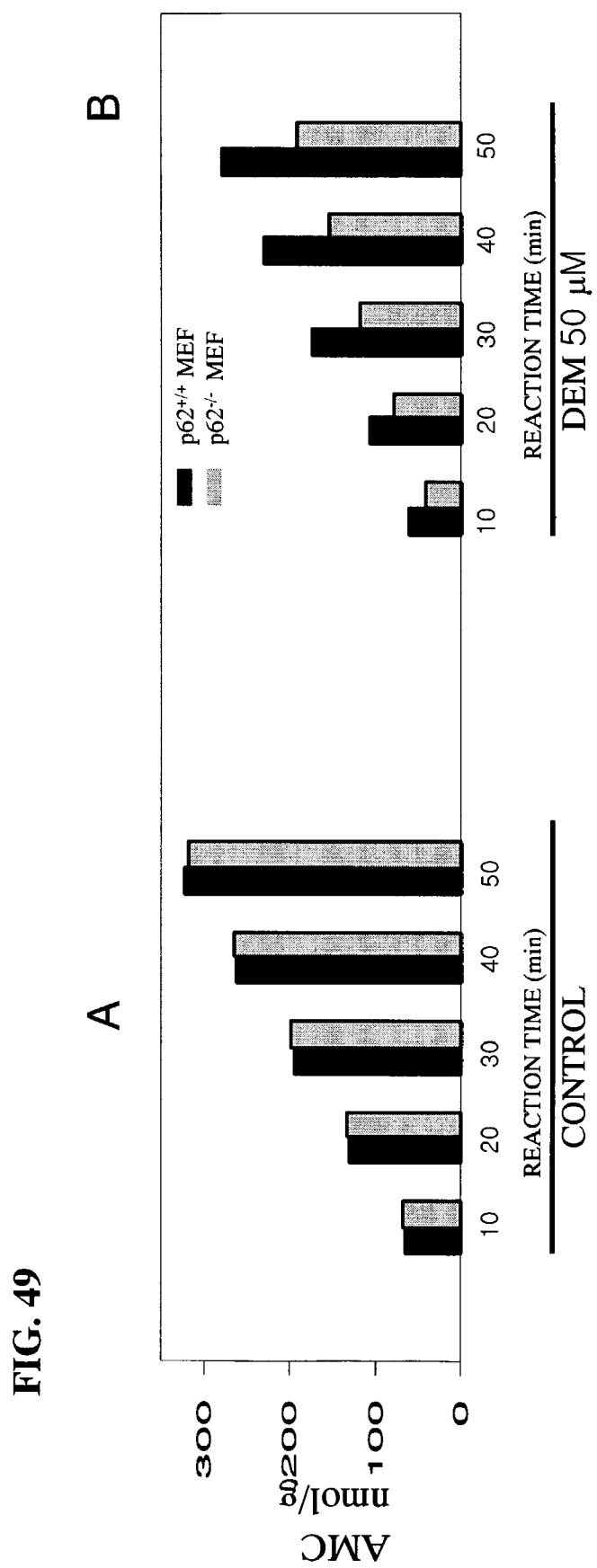
FIGS. 49A-49B show proteasome peptidase activities in p62+/+ and p62−/− mouse embryo fibroblast (MEF). Cultures were treated or not treated with diethylmaleate (DEM, 50 mM) for 12 hours. Cells were harvested and homogenized in extraction buffer. Membranes and cellular debris were eliminated by centrifugation at 10,000 g and soluble extract was recovered. Peptidase activities of the proteasome were assayed by using fluorogenic peptides LLVY-AMC for the chymotrypsin-like activity.

In addition to the above, FIGS. 49A-49B show proteasome peptidase activities in p62+/+ and p62−/− mouse embryo fibroblast (MEF). Cultures were treated or not treated with diethylmaleate (DEM, 50 mM) for 12 hours. Cells were harvested and homogenized in extraction buffer. Membranes and cellular debris were eliminated by centrifugation at 10,000 g and soluble extract was recovered. Peptidase activities of the proteasome were assayed by using fluorogenic peptides LLVY-AMC (SEQ ID NO: 2) for the chymotrypsin-like activity. Oxidative stress induced by treatment of DEM (i.e. glutathione depletion) more sensitively reduced proteasomal activity in the p62-null cells. Taken all together, p62 is a key cellular element in defense against oxidative stress either endogenously generated or exogenously provided. One of the defense mechanisms would be that p62 collects and sequestrate misfolded proteins (oxidized or ubiquitinated) into the intracellular inclusions. On the other hand, accumulation of such misfolded proteins over the cellular capacity would lead to cell death representing the pathologic features of neurodegeneration. In addition, endogenous imbalance of redox system and accumulated ROS by p62 malfunction may be a cause of the various phenotypes observed in the p62 null mice.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A homozygous p62 mutant transgenic mouse, which does not produce p62 protein and exhibits a phenotype which is selected from the group consisting of obesity, diabetes, fatty liver, and early mortality for male, whose somatic and germ cells comprise a functionally disrupted endogenous p62 gene, wherein said disrupted gene is generated in the mouse or an ancestor of the mouse at an embryonic stage by introduction of a targeting vector.

2. A mouse somatic cell having a genome comprising a homozygous functionally disrupted p62 gene, which is isolated from the transgenic mouse of claim 1.

* * * * *